US006843793B2

(12) United States Patent  
Brock et al.

(10) Patent No.: US 6,843,793 B2
(45) Date of Patent: Jan. 18, 2005

(54) SURGICAL INSTRUMENT

(75) Inventors: David L. Brock, Natick, MA (US); Woojin Lee, Hopkinton, MA (US)

(73) Assignee: endoVia Medical, Inc., Norwood, MA (US)

( * ) Notice: Subject to any disclaimer, the term of this patent is extended or adjusted under 35 U.S.C. 154(b) by 66 days.

(21) Appl. No.: 10/008,871

(22) Filed: Nov. 16, 2001

(65) Prior Publication Data

US 2002/0133173 A1 Sep. 19, 2002

Related U.S. Application Data

(63) Continuation-in-part of application No. 09/827,503, filed on Apr. 6, 2001, now Pat. No. 6,432,112, which is a continuation of application No. 09/746,853, filed on Dec. 21, 2000, now Pat. No. 6,692,485, which is a division of application No. 09/375,666, filed on Aug. 17, 1999, now Pat. No. 6,197,017, which is a continuation of application No. 09/028,550, filed on Feb. 24, 1998, now abandoned, application No. 10/008,871, and a continuation-in-part of application No. 09/783,637, filed on Feb. 14, 2001, which is a continuation of application No. PCT/US00/12553, filed on May 9, 2000, application No. 10/008,871, which is a continuation-in-part of application No. PCT/US01/11376, and a continuation-in-part of application No. 09/827,503, and a continuation-in-part of application No. 09/746,853, application No. 10/008,871, and a continuation-in-part of application No. 09/827,503, and a continuation-in-part of application No. 09/746,853, application No. 10/008,871, and a continuation-in-part of application No. 09/827,643, filed on Apr. 6, 2001, now Pat. No. 6,554,844, and a continuation-in-part of application No. PCT/US00/12553.

(60) Provisional application No. 60/133,407, filed on May 10, 1999, provisional application No. 60/257,869, filed on Dec. 21, 2000, provisional application No. 60/195,264, filed on Apr. 7, 2000, provisional application No. 60/293,346, filed on May 24, 2001, provisional application No. 60/279,087, filed on Mar. 27, 2001, provisional application No. 60/313,496, filed on Aug. 21, 2001, provisional application No. 60/313,497, filed on Aug. 21, 2001, provisional application No. 60/313,495, filed on Aug. 21, 2001, provisional application No. 60/269,203, filed on Feb. 15, 2001, provisional application No. 60/269,200, filed on Feb. 15, 2001, provisional application No. 60/276,151, filed on Mar. 15, 2001, provisional application No. 60/276,217, filed on Mar. 15, 2001, provisional application No. 60/276,086, filed on Mar. 15, 2001, provisional application No. 60/276,152, filed on Mar. 15, 2001, provisional application No. 60/257,816, filed on Dec. 21, 2000, provisional application No. 60/257,868, filed on Dec. 21, 2000, provisional application No. 60/257,867, filed on Dec. 21, 2000, and provisional application No. 60/257,869, filed on Dec. 21, 2000.

(51) Int. Cl.$^7$ .............................................. A61B 19/00
(52) U.S. Cl. ....................................... 606/130; 600/424
(58) Field of Search ..................... 606/1, 130; 600/424, 600/102, 104; 128/898; 395/99, 89, 95, 97

(56) References Cited

U.S. PATENT DOCUMENTS 2,978,118 A 4/1961 Goertz et al.

(List continued on next page.)

FOREIGN PATENT DOCUMENTS

EP 0776738 A2 6/1997

(List continued on next page.)

OTHER PUBLICATIONS

Ikuta, et al., "Shape Memory Alloy Servo Actuator System With Electric Resistance Feedback And Application For Active Endoscope", 1988 IEEE, CH2555–1/88/0000/ 0427–430.

(List continued on next page.)

*Primary Examiner*—Pedro Philogene
(74) *Attorney, Agent, or Firm*—Hamilton, Brook, Smith & Reynolds, P.C.

(57) ABSTRACT

A program of instructions for the processor which include: receiving an insertion length of a medical instrument inserted in a patient; and determining a distal end location of the instrument at a target site in the patient from the insertion length. The instrument typically has a straight proximal portion and curved distal portion, lies in a single plane and is a rigid guide member. The instrument is typically inserted and then fixed at a pivot axis outside the patient. The pivot axis is generally aligned with an insertion point at which the instrument is inserted into the patient. The program of instructions may include determining a subsequent location of the distal end associated with pivoting about the pivot axis. The program of instructions may include determining a subsequent location of the distal end associated with axial rotation of the instrument, determining a subsequent location of the distal end associated with linear translation along a length axis of the instrument and/or determining a subsequent movement of the distal end in a single plane about the pivot axis. The pivotal axis is typically a reference point used by the program of instructions in determining subsequent movement of the distal end.

68 Claims, 36 Drawing Sheets

U.S. PATENT DOCUMENTS

| | | | |
|---|---|---|---|
| 3,923,166 | A | 12/1975 | Fletcher et al. |
| 4,604,016 | A | 8/1986 | Joyce |
| 4,750,475 | A | 6/1988 | Yoshihashi |
| 4,853,874 | A | 8/1989 | Iwamoto et al. |
| 5,078,140 | A | 1/1992 | Kwoh |
| 5,184,601 | A | 2/1993 | Putman |
| 5,217,003 | A | 6/1993 | Wilk |
| 5,238,005 | A | 8/1993 | Imran |
| 5,339,799 | A | 8/1994 | Kami et al. |
| 5,350,355 | A | 9/1994 | Sklar |
| 5,368,015 | A | 11/1994 | Wilk |
| 5,397,323 | A | 3/1995 | Taylor et al. |
| 5,410,638 | A | 4/1995 | Colgate et al. |
| 5,441,505 | A | 8/1995 | Nakamura |
| 5,515,478 | A | 5/1996 | Wang |
| 5,524,180 | A | 6/1996 | Wang et al. |
| 5,572,999 | A | 11/1996 | Funda et al. |
| 5,618,294 | A | 4/1997 | Aust et al. |
| 5,624,398 | A | 4/1997 | Smith et al. |
| 5,626,595 | A | 5/1997 | Sklar et al. |
| 5,631,973 | A | 5/1997 | Green |
| 5,632,758 | A | 5/1997 | Sklar |
| 5,649,956 | A | 7/1997 | Jensen et al. |
| 5,762,458 | A | 6/1998 | Wang et al. |
| 5,784,542 | A | 7/1998 | Ohm et al. |
| 5,792,135 | A | 8/1998 | Madhani et al. |
| 5,800,423 | A | 9/1998 | Jensen |
| 5,807,377 | A | 9/1998 | Madhani et al. |
| 5,807,378 | A | 9/1998 | Jensen et al. |
| 5,808,665 | A | 9/1998 | Green |
| 5,810,880 | A | 9/1998 | Jensen et al. |
| 5,814,038 | A | 9/1998 | Jensen et al. |
| 5,815,640 | A | 9/1998 | Wang et al. |
| 5,817,084 | A | 10/1998 | Jensen |
| 5,855,583 | A | 1/1999 | Wang et al. |
| 5,876,325 | A * | 3/1999 | Mizuno et al. ............. 600/102 |
| 5,878,193 | A | 3/1999 | Wang et al. |
| 5,907,664 | A | 5/1999 | Wang et al. |
| 5,931,832 | A | 8/1999 | Jensen |
| 5,954,692 | A | 9/1999 | Smith et al. |
| 5,976,122 | A | 11/1999 | Madhani et al. |
| 6,001,108 | A | 12/1999 | Wang et al. |
| 6,007,550 | A * | 12/1999 | Wang et al. ................. 606/139 |
| 6,024,695 | A | 2/2000 | Taylor et al. |
| 6,063,095 | A | 5/2000 | Wang et al. |
| 6,080,181 | A | 6/2000 | Jensen et al. |
| 6,102,850 | A | 8/2000 | Wang et al. |
| 6,106,511 | A * | 8/2000 | Jensen ........................... 606/1 |
| 6,120,433 | A | 9/2000 | Mizuno et al. |
| 6,132,368 | A | 10/2000 | Cooper |
| 6,197,017 | B1 | 3/2001 | Brock et al. |
| 6,223,100 | B1 | 4/2001 | Green |
| 6,246,200 | B1 | 6/2001 | Blumenkranz et al. |
| 6,301,526 | B1 | 10/2001 | Kim et al. |
| 6,341,231 | B1 * | 1/2002 | Ferre et al. ................. 600/424 |
| 6,364,888 | B1 | 4/2002 | Niemeyer et al. |
| 6,490,490 | B1 | 12/2002 | Uchikubo et al. |

FOREIGN PATENT DOCUMENTS

| | | |
|---|---|---|
| JP | 114000 | 7/1994 |
| WO | WO98/25666 | 6/1998 |
| WO | WO00/60521 | 10/2000 |
| WO | WO 00/67640 | 11/2000 |

OTHER PUBLICATIONS

M.W. Thring, "Robots And Telechirs: Manipulators With Memory; Remote Manipulators; Machine Limbs For the Handicapped", First published in 1983 by Ellis Horwood Limited.

Davies, BL, et al., "A Surgeon Robot for Prostatectomies," Center for Robotics, Imperial College of Science, *IEEE* (*1991*).

Kwoh, Y.S., et al., "A Robot with Improved Absolute Positioning Accuracy for CT Guided Stereotactic Brain Surgery," *IEEE Transactions on Biomedical Engineering*, 35 (2) (1998).

Dohi, T., "Medical Application of Robotics Mechatronics," *International Biomedical Engineering Days*, (1992).

Sabatini, A.M., et al., "Force Feedback–Based Telemicromanipulation for Robot Surgery on Soft Tissue," *IEEE Engineering in Medicine & Biology Society*, (1989).

* cited by examiner

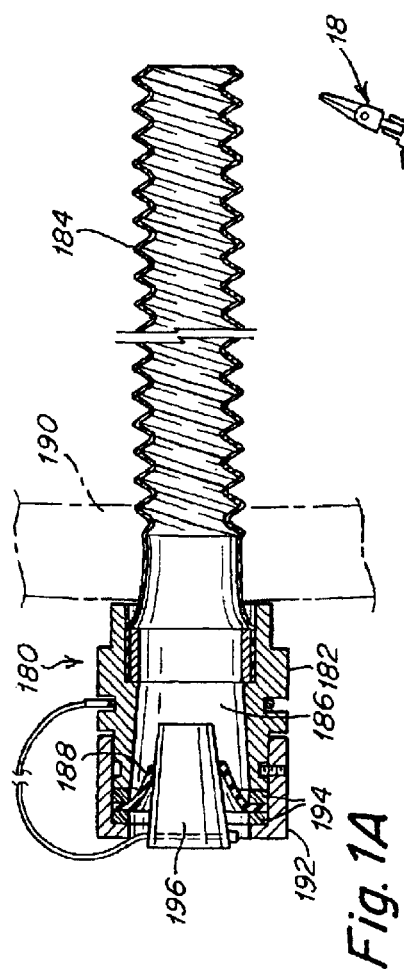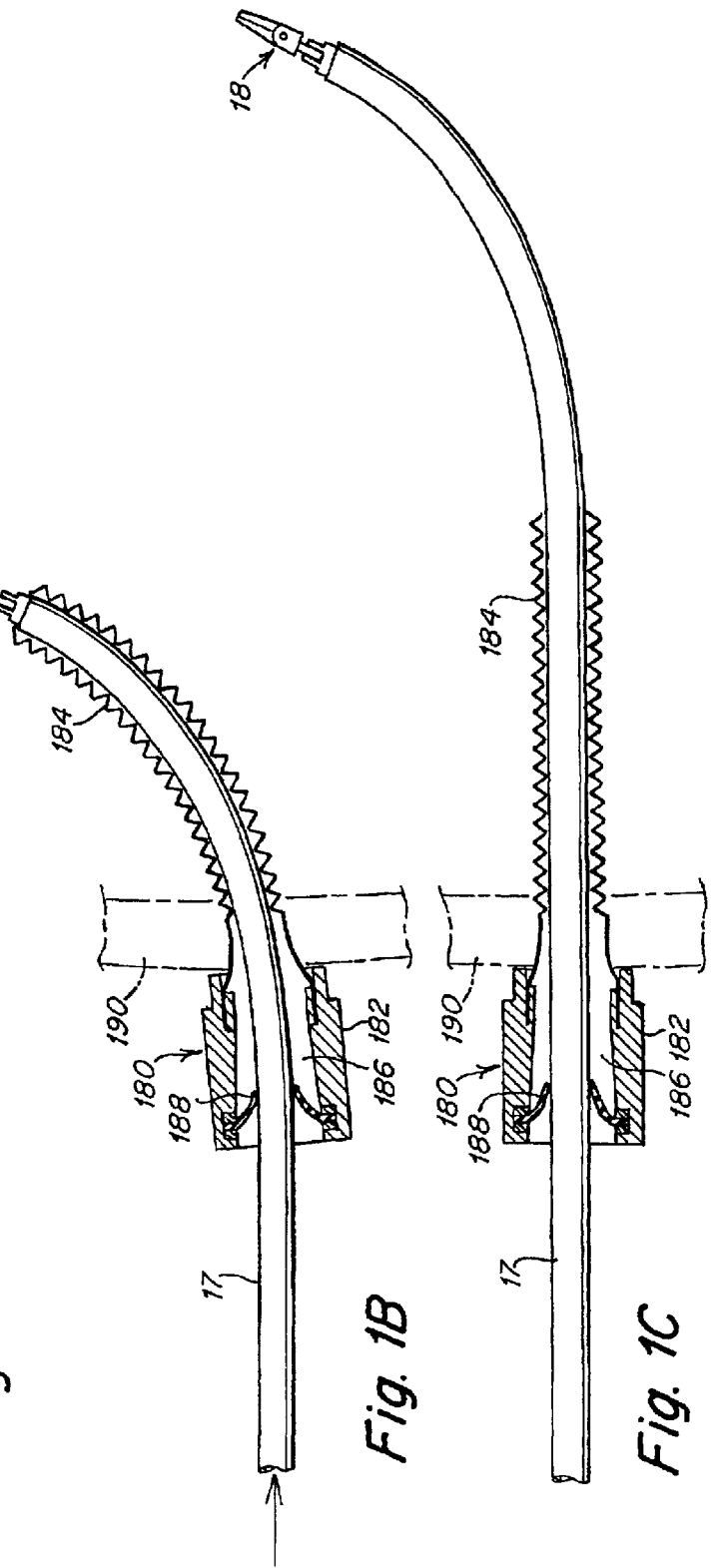

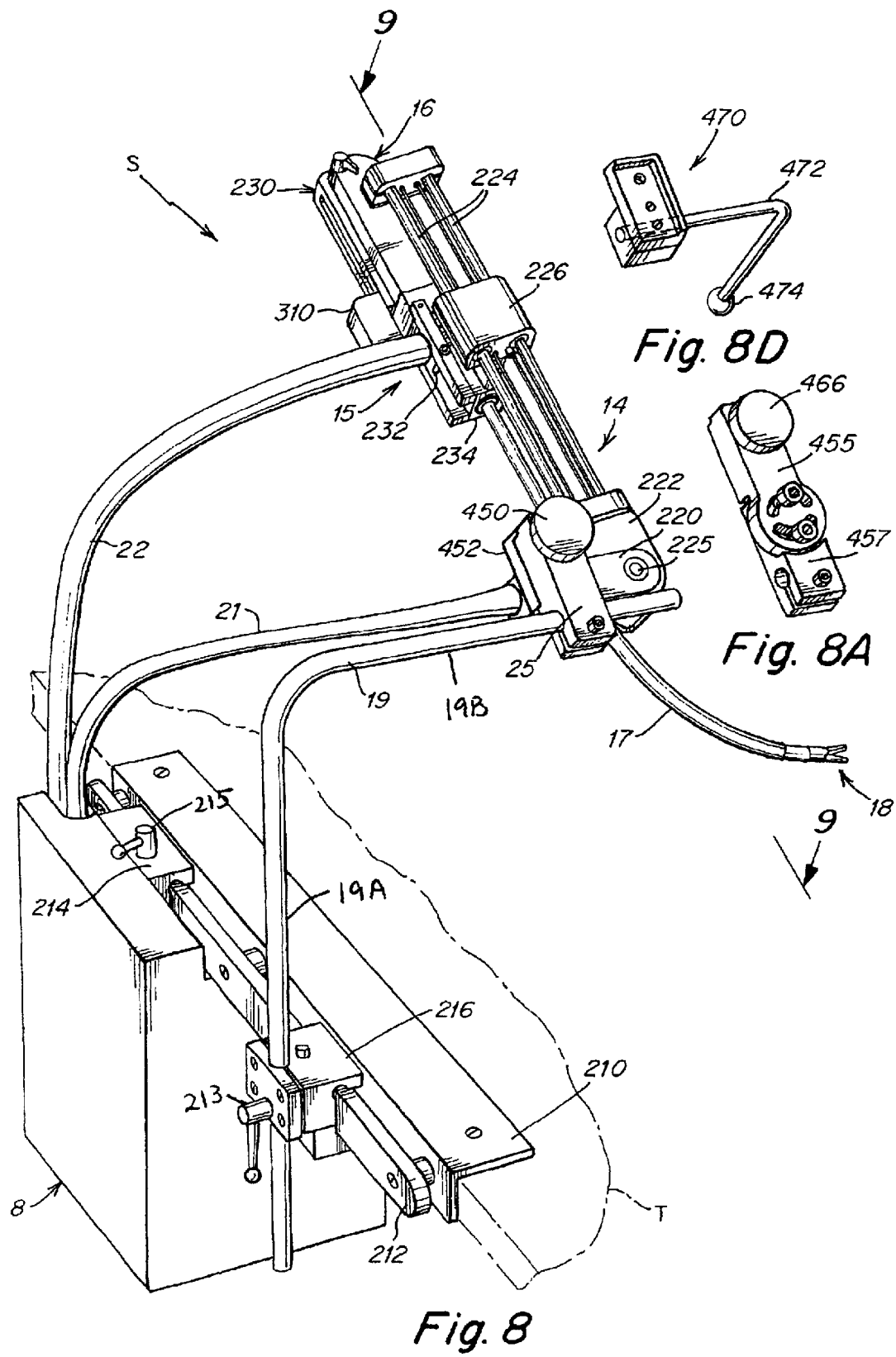

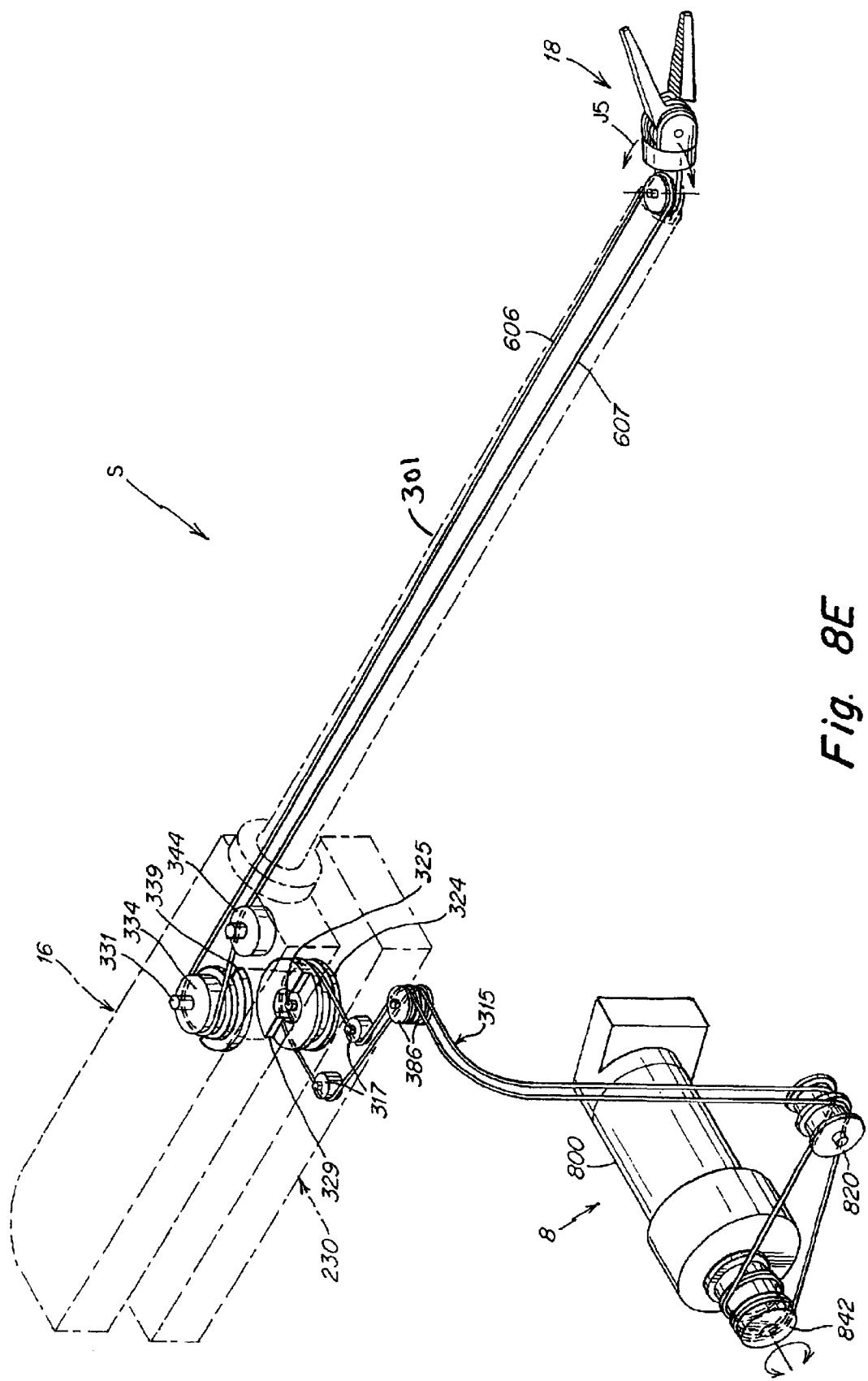

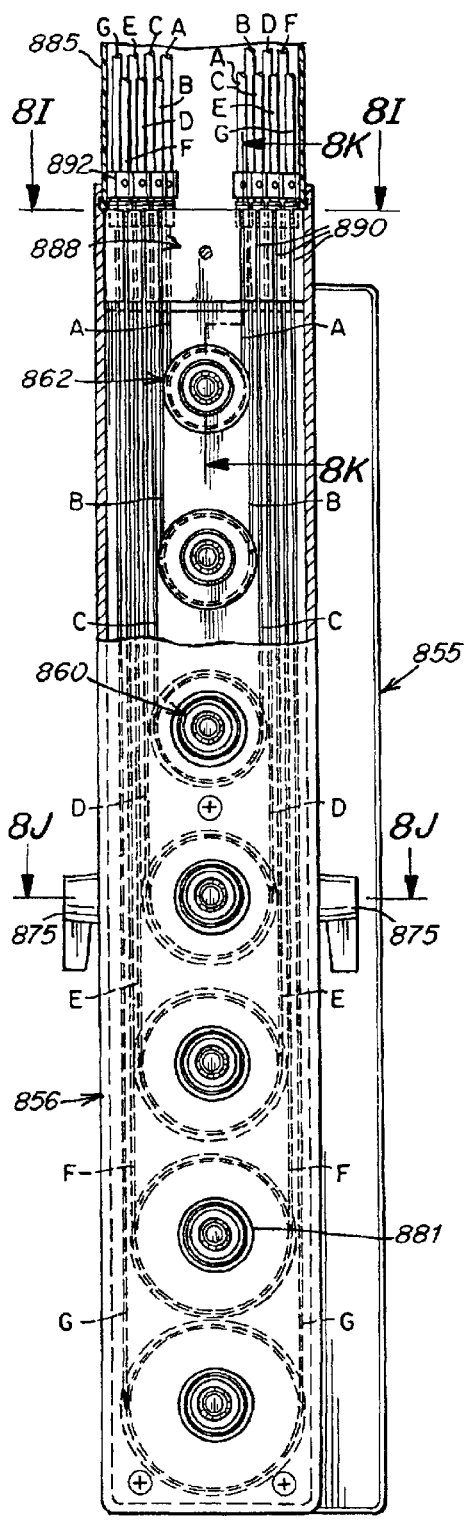
Fig. 8H
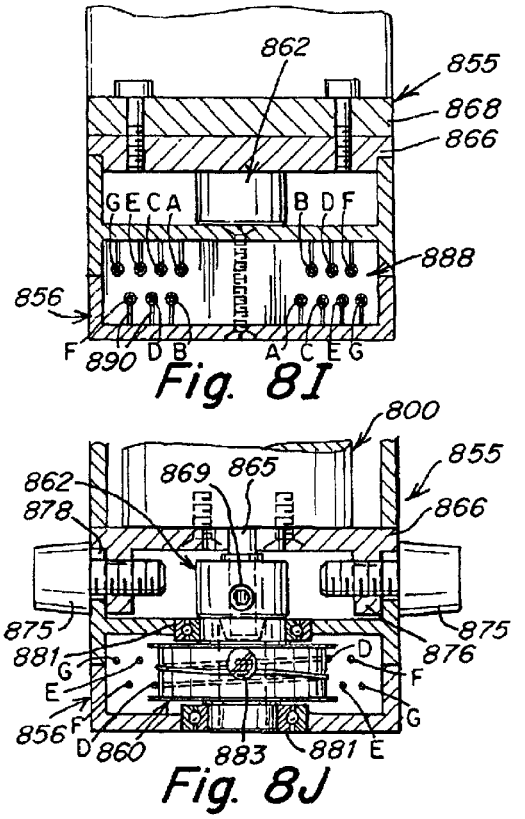
Fig. 8I
Fig. 8J
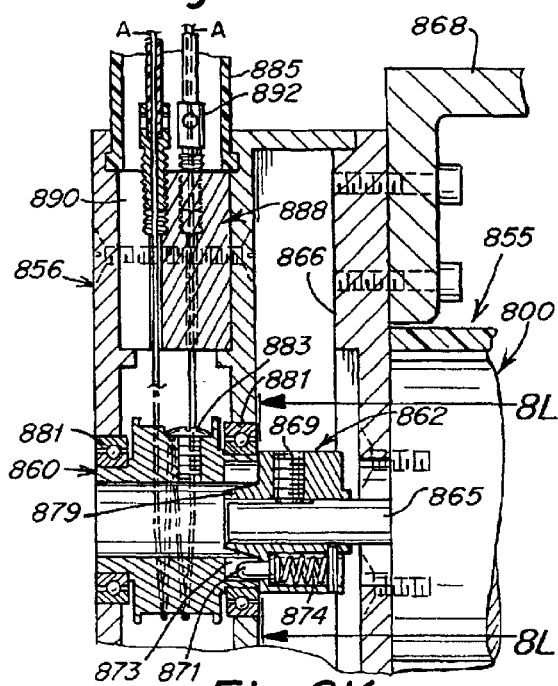
Fig. 8K

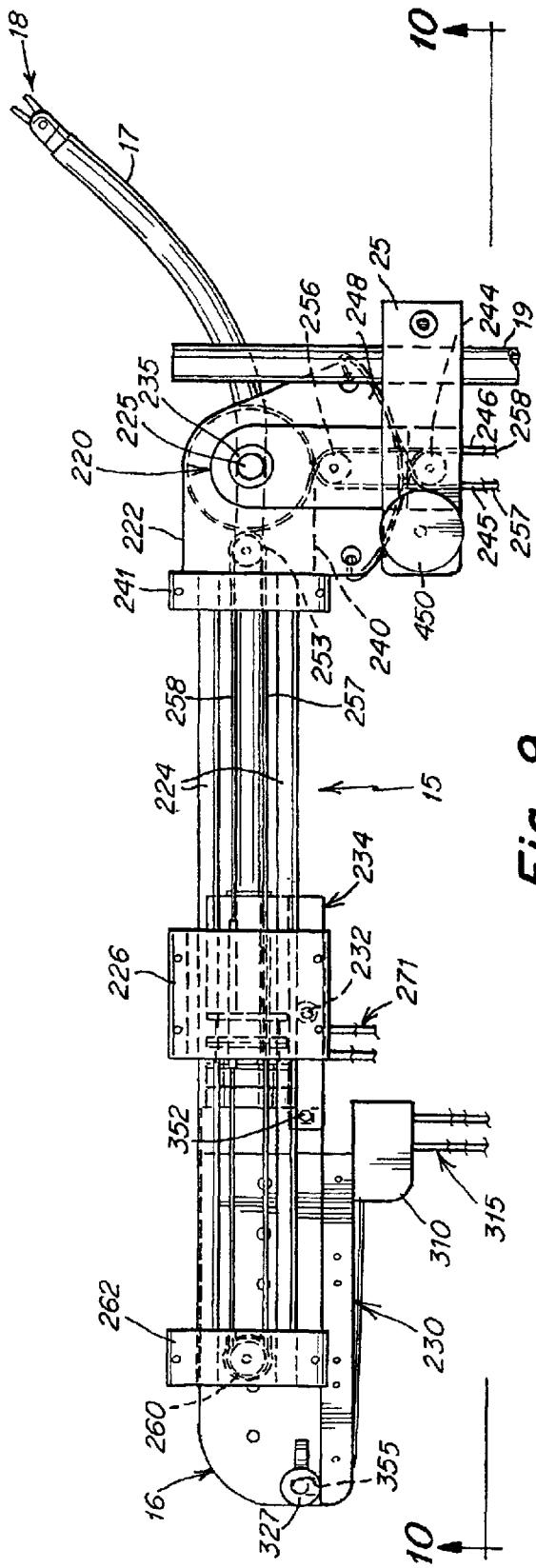
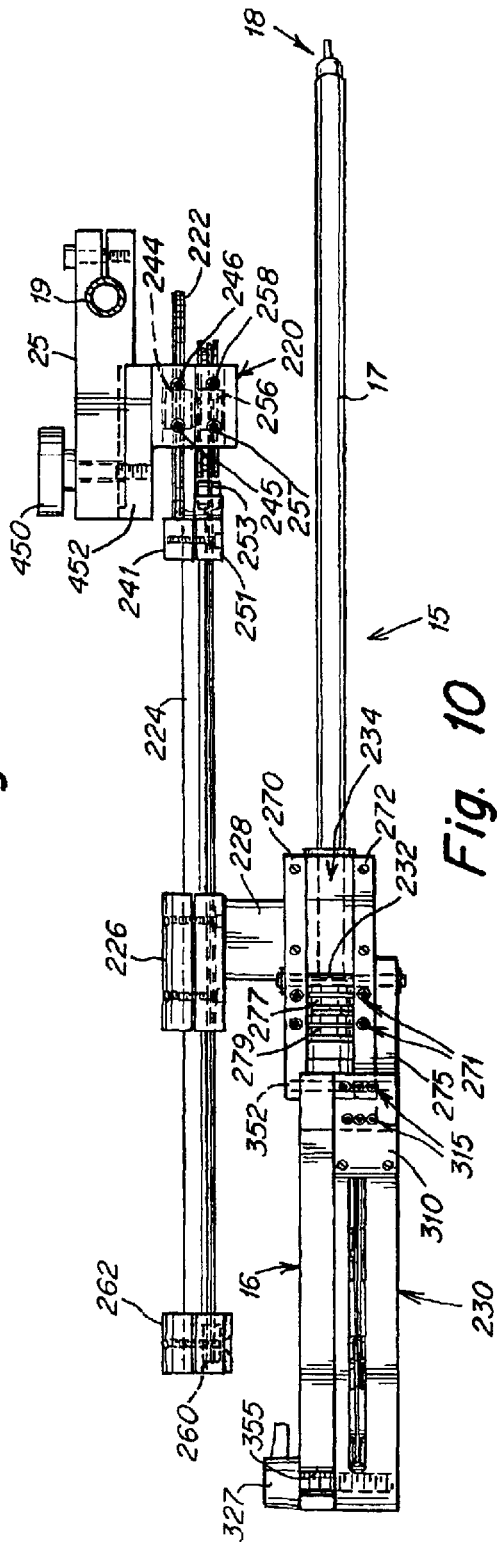

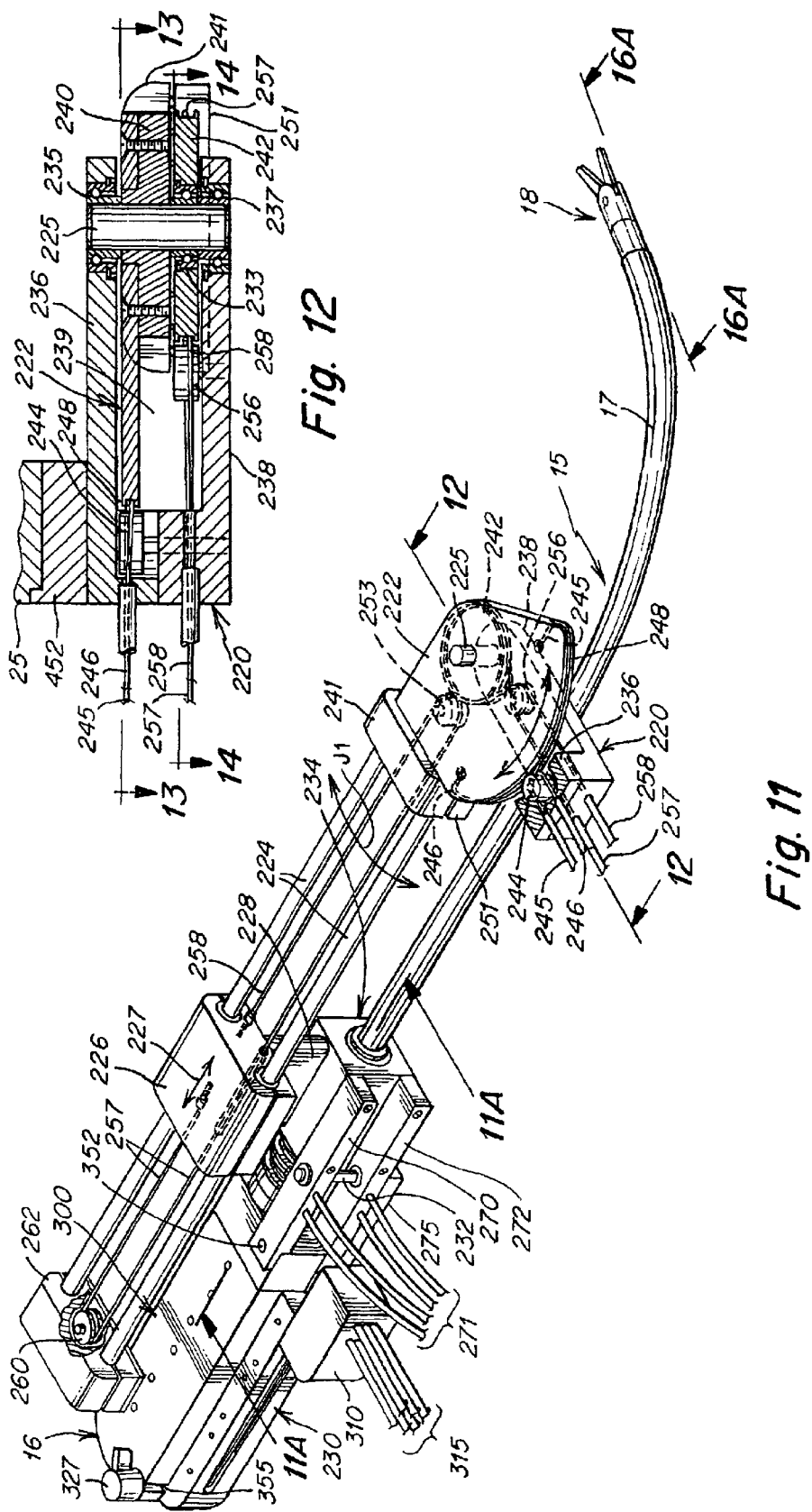

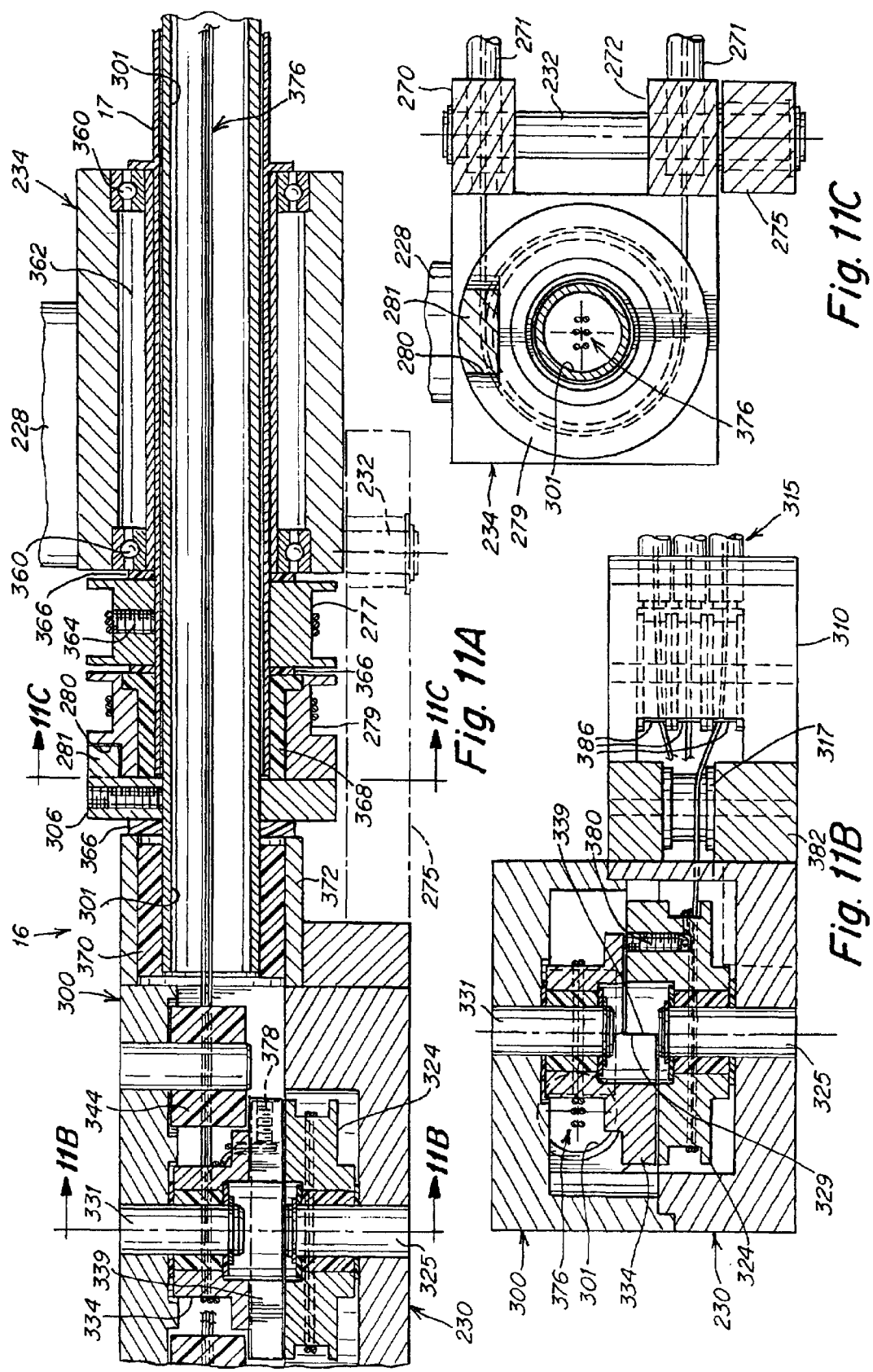

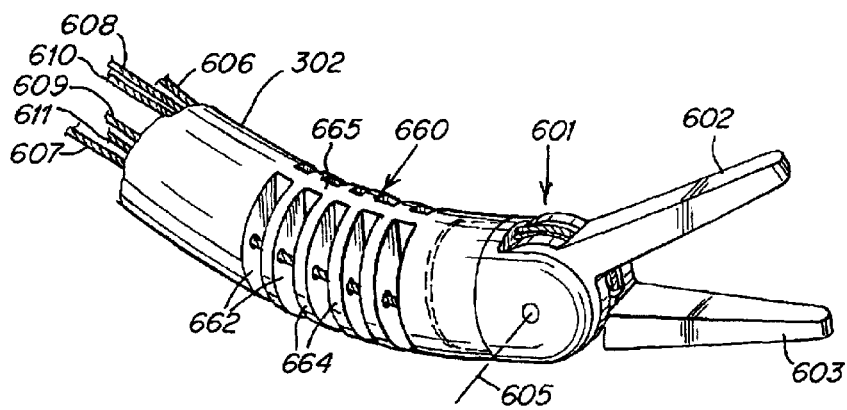
Fig. 16E
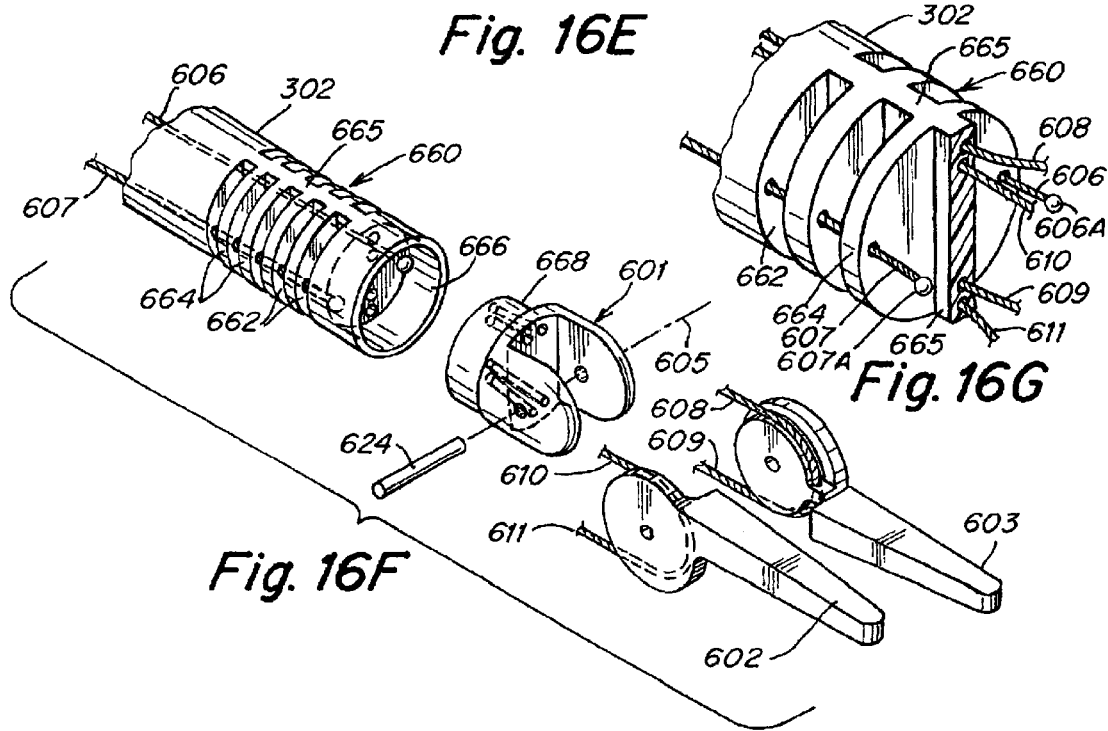
Fig. 16F
Fig. 16G
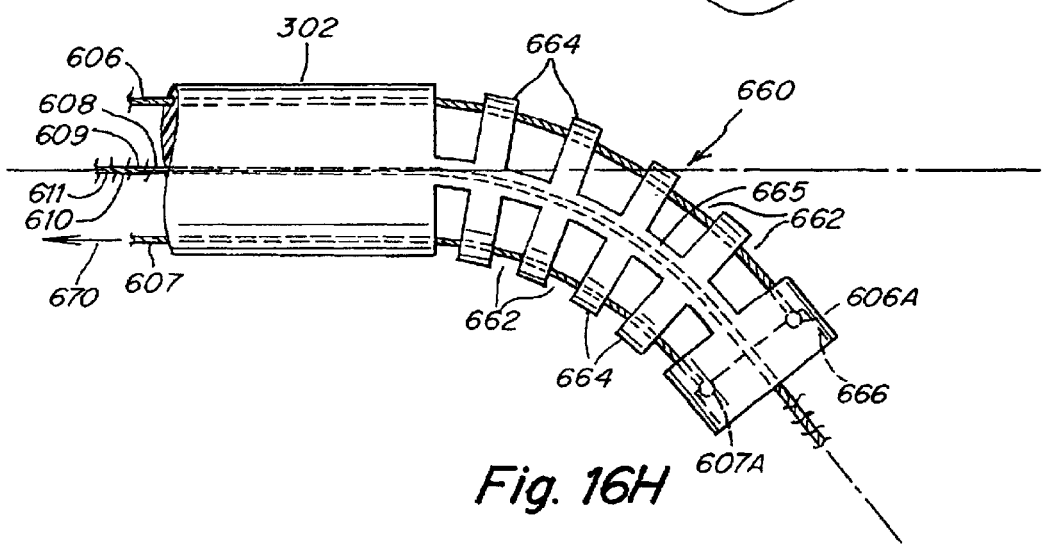
Fig. 16H

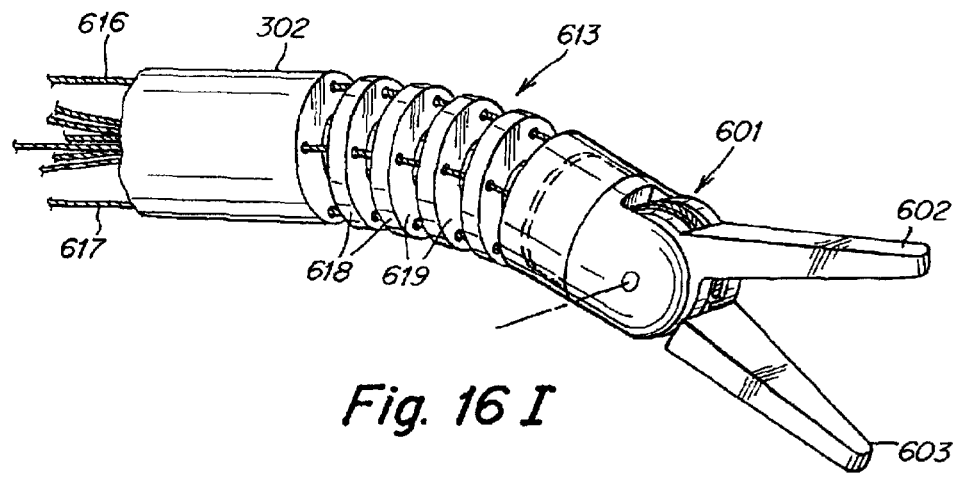
Fig. 16 I
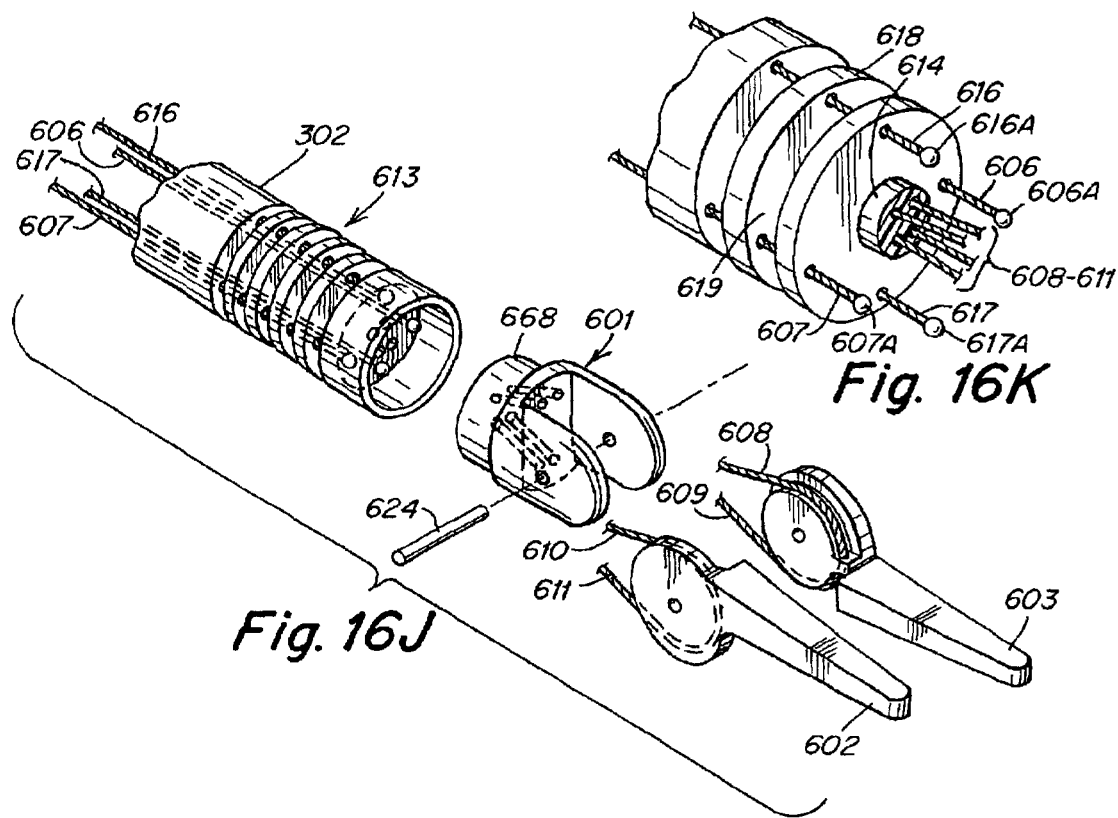
Fig. 16J
Fig. 16K

SURGICAL INSTRUMENT

CROSS REFERENCE TO RELATED APPLICATION

This application is a continuation-in-part of and claims the benefit of priority from U.S. application Ser. No. 09/827,503, filed Apr. 6, 2001, now U.S. Pat. No. 6,432,112 which is a continuation of U.S. applifcation Ser. No. 09/746,853, filed Dec. 21, 2000, now U.S. Pat. No. 6,692,485 which is a divisional of U.S. application Ser. No. 09/375,666, now U.S. Pat No. 6,197,017, filed Aug. 17, 1999, which is a continuation of U.S. application Ser. No. 09/028,550 filed Feb. 24, 1998, now abandoned. This application is also a continuation-in-part of and claims the benefit of priority from U.S. application Ser. No. 09/783,637, filed Feb. 14, 2001, which is a continuation of PCT/US00/12553 filed May 9, 2000, which claims the benefit of priority of U.S. provisional patent application Ser. No. 60/133,407, filed May 10, 1999, now abandoned. This application is also a continuation-in-part of and claims the benefit of priority from PCT/US01/11376 filed Apr. 6, 2001 which claims priority to U.S. application Ser. Nos. 09/746,853 filed Dec. 21, 2000 now U.S. Pat. No. 6,692,485 and 09/827,503 filed Apr. 6, 2001 now U.S. Pat. No. 6,432,112. This application is also a continuation-in-part of and claims the benefit of priority from U.S. application Ser. Nos. 09/746,853 filed Dec. 21, 2000 now U.S. Pat. No. 6,692,485 and 09/827,503 filed Apr. 6, 2001 now U.S. Pat. No. 6,432,112. This application is also a continuation-in-part of and claims the benefit of priority from U.S. application Ser. No. 09/827,643 filed Apr. 6, 2001 now U.S. Pat. No. 6,554,844 which claims priority to, inter alia, U.S. provisional application Ser. No. 60/257,869 filed Dec. 21, 2000 and U.S. provisional application Ser. No. 60/195,264 filed Apr. 7, 2000 and is also a continuation-in-part of PCT/US00/12553 filed May 9, 2000 from which U.S. application Ser No. 09/783,637 filed Feb. 14, 2001 claims priority.

This application also claims the benefit of priority under 35 U.S.C. §§119 and 120 to U.S. Provisional Application Ser. No. 60/293,346 filed May 24, 2001, U.S. Provisional Application Ser. No. 60/297,087, filed Mar. 27, 2001, U.S. Provisional Application Ser. No. 60/313,496 filed Aug. 21, 2001, U.S. Provisional Application Ser. No. 60/313,497 filed Aug. 21, 2001, U.S. Provisional Application Ser. No. 60/313,495 filed Aug. 21, 2001, U.S. Provisional Application Ser. No. 60/269,203 filed Feb. 15, 2001, U.S. Provisional Application Ser. No. 60/269,200 filed Feb. 15, 2001, U.S. Provisional Application Ser. No. 60/276,151 filed Mar. 15, 2001, U.S. Provisional Application Ser. No. 60/276,217 filed Mar. 15, 2001, U.S. Provisional Application Ser. No. 60/276,086 filed Mar. 15, 2001, U.S. Provisional Application Ser. No. 60/6276,152 filed Mar. 15, 2001, U.S. Provisional Application Ser. No. 60/257,816 filed Dec. 21, 2000, U.S. Provisional Application Ser. No. 60/257,868 filed Dec. 21, 2000, U.S. Provisional Application Ser. No. 60/257,867 filed Dec. 21, 2000, U.S. Provisional Application Ser. No. 60/257,869 filed Dec. 21, 2000.

The disclosures of all of the foregoing applications and U.S. Pat. No. 6,197,017 are all incorporated herein by reference in their entirety.

This application further incorporates by reference in its entirety the disclosures of the following U.S. patent applications which are being filed concurrently on the same date herewith, having the following titles and Ser. Nos.: 10/014,145—Surgical Instrument; 10/012,845—Surgical Instrument; 10/008,964—Surgical Instrument; 10/013,046—Surgical Instrument; 10/011,450—Surgical Instrument; 10/008,457—Surgical Instrument; 10/008,871—Surgical Instrument; 10/023,024—Flexible Instrument; 10/011,371—Flexible Instrument; 10/011,449—Flexible Instrument; 10/010,150—Flexible Instrument; 10/022,038—Flexible Instrument; and 10/012,586—Flexible Instruments.

BACKGROUND OF THE INVENTION

The present invention relates to surgical instruments and more particularly to surgical instruments which are remotely controlled by electronic control signals generated by a user which are sent to a drive unit which drives mechanically drivable components of a mechanical apparatus which support a surgical instrument.

SUMMARY OF THE INVENTION

Instrument Support and Mounting

One aspect of the present invention relates to a support member for holding a medical procedure instrument holder in a fixed position relative to a patient.

In one embodiment, a medical procedure instrument is provided, including an instrument holder, an instrument insert, and a support. The instrument holder includes an elongated guide member for receiving the instrument insert. The insert carries on its distal end a medical tool for executing the medical procedure. The instrument holder is manually insertable into a patient so as to dispose a distal end of the guide member into a target site in which the procedure is to be executed. The support holds the instrument holder fixed in position relative to the patient. The instrument holder is held in fixed position in an incision in the patient between changes of instrument inserts during the course of a procedure such that trauma or damage which can result from withdrawal and re-insertion of another or the same instrument is minimized or eliminated. The distal end of the elongated guide member is preferably curved and at least the distal end of the instrument insert is flexible to enable the insert to slide through the curved distal end of the guide member.

The instrument insert typically includes an elongated shaft having a proximal end, a distal end and a selected length between the two ends. One or more portions of the elongated shaft along its length, and most typically a distal end portion, may comprise a mechanically and controllably deformable material such that the portion of the selected lengths of the shaft which are deformable are controllably bendable or flexible in any one or more of an X, Y and Z axis direction relative to the axis of the shaft thus providing an additional three degrees of freedom of movement control. Flexible cables, rods or the like which are connected at one end to a deformable or flexible portion of a shaft and are drivably intercoupled to a controllably drivable drive unit are typically included for effecting control of the bending or flexing.

In one embodiment, the support includes a bracket that holds an instrument holder to the support at a fixed reference point. The instrument holder is then pivotally supported at this reference point from the bracket.

In various embodiments, the instrument insert is manually engageable and disengageable with the instrument holder. Generally, the instrument holder is inserted into the patient first, and then the insert is engaged to the holder, such that the medical tool at the distal end of the insert extends beyond the distal end of the guide member at the target site. One advantage is to maintain the guide member with its distal end at the target site upon withdrawal of the instrument insert. This enables exchange of instrument inserts during the procedure and facilitates ease of placement of the next instrument insert.

The instrument insert preferably includes a mechanically drivable mechanism for operating the medical tool. The instrument holder also includes a mechanical drive mechanism such that the drive and drivable mechanisms are engageable and disengageable with one another, in order to enable engagement and disengagement between the insert and holder. Preferably, a drive unit for controlling the instrument insert and holder is disposed remote from the insert and holder, outside of a sterile field which may be defined by the area above the operating table.

In another embodiment, a medical procedure instrument is provided which includes an instrument holder, an instrument insert, and a support. The instrument holder includes an elongated guide member for receiving the insert, the insert carrying at its distal end a medical tool for executing a medical procedure. The support holds the instrument holder with a distal end of the guide member at a target site internal of the patient. The insert is adapted for ready insertion and withdrawal by way of the guide member, while the guide member is held at the target site. Again, this facilitates ready exchange of instrument inserts during a medical procedure. The instrument inserts are preferably disposable, so they can be discarded after a single insertion and withdrawal from the patient.

In a further embodiment, a remote controlled instrument system is provided which includes a user interface, an instrument, a support, and a controller. The user interface allows an operator to manually control an input device. The instrument has at its distal end a tool for carrying out a procedure, the instrument being manually inserted into a patient so as to dispose the tool at a target site at which the procedure is to be executed. The support holds a part of the instrument fixed in position relative to the patient. A controller coupled between the user interface and the instrument is responsive to a remote control by the operator for controlling the instrument at the target site.

Another embodiment is a method for remotely controlling an instrument having multiple degrees-of-freedom. The instrument is manually inserted into a patient so as to dispose its distal end at a target site at which a procedure is to be executed. An instrument holder, that receives the instrument, is supported stationary relative to the patient during the procedure so as to maintain the instrument distal end at the target site. A user input device is used to remotely control the motion of the instrument distal end in executing the procedure at the target site.

In a further method embodiment for remotely controlling an instrument, an instrument holder is provided for removably receiving and supporting a disposable instrument insert. The instrument holder is inserted into a patient so as to dispose its distal end at an operative site at which the procedure is to be executed. The instrument insert is received in the holder so as to dispose a tool at the distal end of the insert so that it extends from the holder and is positioned at the operative site. A user input device remotely controls motion of the insert in executing the procedure at the operative site. Preferably, the instrument holder is maintained at the operative site as the insert is withdrawn, enabling ready exchange of one instrument insert for another.

The invention also provides a medical apparatus for exchanging surgical instruments having a selected tool to be positioned at an operative site of a subject, the apparatus comprising: a guide tube having an open distal end inserted through an incision of the subject, the guide tube being fixedly positioned relative to the subject such that the distal end of the guide tube is fixedly positioned at the operative site, the guide tube being readily manually insertable through the incision; one or more surgical instruments each having a selected tool mounted at a distal end of the instrument; wherein the one or more surgical instruments are readily insertable through the fixedly positioned guide tube such that the selected tool of an instrument is disposed through the open distal end of the guide tube at the operative site upon full insertion of the surgical instrument, the guide tube having a first mounting interface and the surgical instruments having a second mounting interface, the first and second mounting interfaces being readily engageable with each other to fixedly mount the surgical instruments within the guide tube upon full insertion of the surgical instrument. Such a medical apparatus may further comprise a readily manually portable support for fixedly positioning the guide tube in a selected location and orientation relative to the subject, the manually portable support being readily fixedly attachable to and detachable from a stationary structure on or relative to which the subject is mounted.

These and other embodiments of the instrument, system and method are more particularly described in the later detailed description section.

Ready Attachability, Couplability and Mountability

Another aspect of the invention is to provide a drive unit or motor assembly which is attachable and detachable from a medical instrument assembly in order to provide one or more of the features of, positioning the motor assembly outside a sterile field in which a medical procedure takes place, increasing portability of the instrument assembly for ease of positioning with respect to the patient and ease of access to the patient during the procedure, e.g., avoiding bulky and unnecessary electromechanical equipment in the sterile field of the procedure so as to increase ease of access to the patient, enabling detachment, sterilization and reusability of certain components of the instrument assembly and/or detachment and disposability of certain other portions of the instrument assembly.

In the first embodiment, a medical procedure instrument is provided, including a medical implement and a drive unit. The medical implement includes a mechanically drivable mechanism intercoupled with the tool used in executing a medical procedure. A drive unit, disposed remote from the medical implement, is used for mechanically driving the implement. The implement is initially decoupled from the drive unit and manually insertable into a patient so as to dispose the tool at an operative site within the patient. The medical implement is attachable and detachable with the drive unit for coupling and decoupling the mechanically drivable mechanism with the drive unit.

In various preferred embodiments, the medical implement includes a holder and an instrument insert, the holder receiving the insert and the insert carries the mechanically drivable mechanism. Preferably, the insert is an integral disposable unit, including a stem section with the tool at its distal end and the mechanically drivable mechanism at its proximal end.

The drive unit may be an electromechanical unit, and mechanical cabling may intercouple the drive unit with the mechanically drivable mechanism. Mechanical cabling may be provided to control motion for both the instrument holder, and the instrument insert. The medical implement may be remotely controllable by a user, manipulating a manually controllable device, which device is connected to the drive unit through an electrical drive control element.

In another embodiment, a slave station of a robotic surgery system is provided in which manipulations by a surgeon control motion of a surgical instrument at a slave station. The slave station includes a support, mechanical cabling, and a plurality of motors. The support is manually portable and is provided to hold the surgical instrument at a position over an operating table so that the instrument may be readily disposed at an operative site. Mechanical cabling is coupled to the instrument for controlling movement of the instrument. The plurality of motors are controlled, by way of a computer interface, and by surgeon manipulations for driving the mechanical cabling. The mechanical cabling is driven by the plurality of motors in a manner so as to be attachable and detachable from the plurality of motors.

In a preferred embodiment, a two section housing is provided, one housing section accommodating the ends of the mechanical cabling and the other housing section accommodating the plurality of motors. The two housing sections are respectively attachable and detachable. A plurality of coupler spindles supported by the one housing section receive cables of the mechanical cabling. The plurality of coupler spindles and plurality motors are disposed in aligned arrays. A plurality of coupler disks of the other housing section are provided, one associated with and supported by each motor by the plurality of motors. The housing sections support the coupler spindles and the coupler disks in aligned engagement. An engagement element may lock the coupler spindles and disks against relative rotation.

In a further embodiment, a robotic surgery system is provided, including an instrument, a support, mechanical cabling, an array of actuators, and an engagement member. The support is manually portable and holds the instrument over an operating table so that the instrument may be disposed at an operative site in a patient for remote control thereof via a computer interface. The mechanical cabling is coupled to the instrument for controlling movement of the instrument. An array of electrically driven actuators is controlled by the computer interface for driving the mechanical cabling. An engagement member intercouples between the mechanical cabling and the array of actuators so that the mechanical cabling is readily attachable to and detachable from the array of actuators.

In another aspect of the invention, there is provided a robotic surgery apparatus comprising: a mechanically drivable surgical instrument for use at an internal operative site of a subject; an electrically driven drive unit for driving the surgical instrument; mechanical cabling drivably intercoupled to the surgical instrument at one end of the cabling; the mechanical cabling having another end which is readily drivably couplable to and decouplable from the drive unit.

In another aspect of the invention, there is provided a robotic surgery apparatus comprising: a surgical instrument for use at an internal operative site of a subject; a mechanically drivable mounting unit on which the surgical instrument is mounted, the mounting unit being drivably movable outside the operative site of the subject; an electrically driven drive unit for driving movement of the mounting unit; mechanical cabling drivably intercoupled to the mounting unit at one end of the cabling; the mechanical cabling having another end which is readily drivably couplable to and decouplable from the drive unit.

In another aspect of the invention there is provided a robotic surgery apparatus comprising: a mechanically drivable surgical instrument for use at an internal operative site of a subject; an electrically driven drive unit for driving the surgical instrument; mechanical cabling drivably intercoupled to the surgical instrument at one end of the cabling; the drive unit being readily manually portable and readily attachable to and detachable from a fixed support on or relative to which the subject is mounted.

These and other embodiments are described in the following detailed description section.

Disposability

Another aspect of the invention is to provide a disposable medical procedure instrument which includes a mechanically drivable mechanism for driving a tool.

Disposable or disposability generally means that a device or mechanism is used or intended for a single use without a re-use of the device/mechanism and/or without the necessity or intention of a use of the device followed by sterilization of the device for an intended re-use. In practice, a device which is intended for one time or single use may be re-used by the user/physician but such re-use more than once, twice or a very limited number of times is not intended for a disposable device or mechanism.

In one embodiment, a medical procedure instrument is provided including a disposable implement and a mounting mechanism interconnected to a drive mechanism. The disposable implement includes a shaft having a tool at its distal end and a mechanically drivable mechanism drivably interconnected to the tool. A mounting mechanism, interconnected to the drive mechanism, enables the mechanically drivable mechanism of the implement to be removably mounted on the mounting mechanism for drivable interconnection to the drive mechanism. The shaft is insertable into a patient along a select length of the shaft to position the tool at a target site in the patient. The shaft together with the mechanically drivable mechanism is disposable.

At various embodiments, the drive mechanism is drivably interconnected to the mounting mechanism at a first interface which is remote from a second interface at which the mechanically drivable mechanism is mounted to the mounting mechanism. The drive mechanism may include a plurality of motors, and the mounting mechanism is preferably attachable and detachable from the drive mechanism. The mounting mechanism may include a guide tube, through which the shaft is inserted into the patient, and wherein the mounting mechanism includes a drivable mechanism for mechanically driving the guide tube.

Preferably, the disposable instrument can be removed from the mounting mechanism and discarded after use, while the mounting mechanism can be removed from the drive mechanism and sterilized for reuse.

The disposable implement is preferably remote controllably drivable by a user via a manually controllable mechanism which is electrically connected to the drive mechanism through an electrical drive control mechanism.

Preferably, the mounting mechanism and the disposable implement are manually portable in a sterile field, while the drive mechanism is outside the sterile field.

In another embodiment, a medical procedure instrument is provided which is a disposable instrument, drivably interconnectable to and disconnectable from a drive mechanism, the disposable instrument including a mechanically drivable interface, drivably interconnected through a shaft to a tool, the mechanically drivably interface being drivably engageable with and disengageable from a second drive interface which is drivably interconnected to the drive mechanism. Preferably, the mechanically drivable interface and the shaft are an integral disposable unit. The disposable implement may be remote controllably drivable by a user via a manually controllable mechanism which is electrically interconnected to the drive mechanism through an electrical drive control mechanism. The second drive interface may be manually portable in a sterile field. After use, the second drive interface is sterilized for reuse. The drive mechanism is outside the sterile field.

In yet another embodiment, a surgical instrument system is provided positionable within an anatomic body structure and controllable by an operator. The system contains a guide member, a support, and an integral instrument member. The guide member has a proximal end and a distal end. The support positions the guide member with the proximal end outside the anatomic body structure and the distal end within the anatomic body structure adjacent to the operative site. An integral instrument member, disposable as a unit, includes a mechanical drivable element, a stem section and a distal tool. The instrument member is removably engageable with the guide member.

In various embodiments, each of the instrument member and guide member has a coupler, the couplers being removably engageable in order to drive the mechanical drivable element of the instrument member. At least one motor is provided remote from the guide member and instrument member, and mechanical cabling is provided from the motor to the instrument member coupler via the guide member coupler to provide at least 1 degree-of-freedom of motion of the instrument member. The couplers may include interengageable wheels. The guide member coupler is pivotal to facilitate the removable engagement of the guide member and instrument member.

In one embodiment, the guide member includes a base piece, and a guide tube extending from the base piece, wherein the coupler is pivotally supported from the base piece. The instrument member stem section has a mechanical cabling extending therethrough from the instrument member coupler to the distal tool. The instrument member stem section may include sections with different amounts of flexibility. The guide tube includes a straight section, and a more distal curved section. When the instrument member engages with the guide member, the more flexible stem section is disposed in the guide tube curved section. An electromechanical drive member may be provided remote from the guide tube and instrument member, having only mechanical coupling to the guide tube and instrument member. The mechanical coupling may control rotation of the guide tube as well as rotation of the instrument stem within the guide tube.

In another embodiment, a disposable integral medical instrument is provided including a mechanical coupler, an elongated stem, and a tool. The mechanical coupler is at the proximal end of instrument for receiving mechanical drive from a drive unit. The elongated stem extends from the mechanical coupler. The tool is disposed at the distal end of the elongated stem and is interconnected, via the elongated stem, to the mechanical coupler. The elongated stem enables removable insertion in an instrument holder to position a tool at a target site inside a patient for performing a medical procedure.

Preferably, the disposable integral medical instrument is attachable to and detachable from an instrument holder in order to couple mechanical drive from a remote drive unit. The mechanical coupler includes at least one interlocking wheel for coupling with the instrument holder. The mechanical coupler includes mechanical cabling extending to the tool. The stem is mounted to enable rotation of the stem relative to the mechanical coupler. A wrist joint may be provided at the distal end of the stem, coupling to the tool. The elongated stem may have a more distal flexible section. The instrument may have a means for registering the mechanical coupler with an instrument holder.

In another aspect of the invention, there is provided a disposable surgical instrument comprising: a disposable elongated tube having a tool mounted at a distal end of the tube; one or more disposable cables drivably interconnected between the tool and a drive unit, the one or more disposable cables extending through the disposable tube between the tool and a proximal end of the disposable tube. The apparatus preferably includes a guide tube having an open distal end, the guide tube being readily manually insertable through an incision in a subject to position the distal end at an operative site within the subject, the disposable elongated tube being readily insertable through the guide tube to position the tool through the open distal end of the guide tube. The apparatus preferably also includes a manually portable support readily fixedly attachable to and detachable from a stationary structure on or relative to which the subject is mounted, the guide tube being readily fixedly interconnectable to and disconnectable from the support for fixedly positioning the distal end of the guide tube at the operative site. The drive unit is preferably mounted remotely from the operative site and is drivably interconnected to the one or more cables extending through the disposable tube by one or more cables extending between the drive unit and the proximal end of the disposable elongated tube.

In another embodiment of the invention there is provided a disposable surgical instrument comprising: a disposable elongated tube having a tool mounted at a distal end of the tube; a disposable mechanically drivable interface mounted at a proximal end of the disposable tube, the tool being drivably intercoupled to a drive unit via the disposable mechanically drivable interface.

These and other features of the invention are set forth more fully in the following detailed description.

Translation and Other Movement Capability

Another aspect of the invention relates to controlled movement of a surgical instrument system having a distal end positionable within a patient. More specifically, the controlled movement may be limited to translation in a predetermined plane. This controlled movement specifies certain degrees-of-freedom of the surgical instrument, including a guide tube that receives an instrument member having a tool at its distal end. Such movement may be remotely controlled via computer control in response to movements by a surgeon at an input interface.

In one embodiment, a surgical instrument system is provided that is adapted to be inserted through an incision of a patient for operation by a surgeon from outside the patient. The system includes an arm member, a support for the arm member and an instrument member. The arm member has a proximal end disposed outside the patient and a distal end internal of the patient. A support for the arm member provides controlled translation of the arm member with a proximal end thereof moving substantially only in a predetermined plane. The instrument member is carried by the arm member and includes a tool disposed at the distal end of the arm member.

In a preferred embodiment, a controller responsive to a surgeon manipulation controls movement of the arm member and of the tool. The surgeon may be positioned at a master station having an input interface, at which the surgeon manipulates an input device. The controller may allow a number of degrees-of-freedom of the tool and of the arm member. In one embodiment, the tool has 4 degrees-of-freedom, while the arm member has 3 degrees-of-freedom. More specifically, the arm member may have one degree-of-freedom in the predetermined plane. The arm member may have another degree-of-freedom that is rotation of the arm member about a longitudinal axis of the arm member. The arm member may have a further degree-of-freedom that is linear movement of the arm member along the longitudinal axis of the arm member. The tool may have one degree-of-freedom that is rotation of the instrument member about a longitudinal axis of the instrument member. The tool may have another degree-of-freedom that is pivotal in a second plane orthogonal to the first plane. The tool may have jaws and a further degree-of-freedom may be provided enabling opening and closing of the jaws.

The support for the arm member may include a support post for positioning the arm member over an operating table upon which a patient is placed. Preferably, the support post positions the arm member at an acute angle to the operating table. The arm member may include a guide tube that receives the instrument member.

In another embodiment, a surgical instrument system is provided adapted to be inserted through an incision in a patient for operation by a surgeon from outside the patient. The system may include an instrument member having a tool at its distal end. The guide member has a guide tube with a proximal end disposed outside the patient and a distal end internal of the patient. The guide tube has an elongated portion with a central access of rotation and a distal portion having an end which is positioned a radial distance away from the central access. The support for the guide member provides controlled translation of the guide member with the proximal end thereof moving substantially only in a predetermined plane.

In various embodiments, a drive unit is coupled to the guide tube for rotating the guide tube and thereby displacing the tool with respect to the central access. Preferably, the distal portion of the guide tube is curved so as to displace the end thereof the radial distance away from the central access. When combined with translation in the plane, the rotation of the guide tube enables three-dimensional placement of the instrument tool.

The instrument member may include a coupler for engaging the instrument member to the guide member, and an elongated section that is, at least, partially flexible for insertion into the guide tube. The instrument member may include in its distal end at least two adjacent link members intercoupled by way of at least one joint, and at least one cable extending along at least one of the link members for operating the adjacent link member. Separate cable sections may be coupled to opposite sides of the adjacent link members for enabling pivoting in either direction of the adjacent link member relative to the at least one link member.

The instrument member can be readily engageable and disengageable with the guide member and constructed to enable exchange with other instrument members. The instrument member may be disposable.

The instrument member may be couplable to and decouplable from a drive unit, the drive unit being controlled by a controller for operating the instrument member. The drive unit may be disposed remote from a sterile field in which the patient and instrument member are disposed.

In another embodiment, an instrument system is provided, including a user interface, an instrument, a support, a controller, and a drive unit. A surgeon may manipulate an input device at the user interface. The instrument has a distal end internal of the patient and carrying at its distal end a tool used in executing a procedure at an operative site of the patient. The support for the instrument includes a pivot at the proximal end of the instrument that limits motion of the proximal end of the instrument substantially only in one plane. The controller receives commands from the user interface for controlling movement of the instrument. A drive unit intercouples with the controller and the instrument.

In a preferred embodiment, the instrument includes an adapter and an instrument insert. The adapter may have a guide tube with an elongated portion having a longitudinal access of rotation and a distal end that is positioned a radial distance away from the longitudinal access. When the distal end of the guide tube is curved, the distal end will orbit about the longitudinal access as the guide tube is rotated under control from the user interface. The insert may be removably couplable with the adapter and include an elongated stem having a tool at its distal end. The adapter and insert may each include a coupler for lateral relative coupling and decoupling of the adapter and insert. The instrument coupler may include a series of wheels that engage with a series of wheels on the adapter coupler.

The instrument insert may have an elongated stem which includes a more flexible stem section disposed distally of a less flexible stem section. Alternatively, the full length of the elongated stem may be flexible. A wrist link, intercoupling a more flexible stem section with the tool, provides one degree-of-freedom of the tool.

In another embodiment of the invention there is provided a remotely controlled surgical instrument system that is adapted to be inserted through an incision of a patient for operation by a surgeon from outside the patient in a remote location, the system comprising: an elongate tube having a proximal end disposed outside the patient and a distal end internal of the patient; a support for the elongate tube that provides controlled translation of said elongate tube with the proximal end thereof moving substantially only in a predetermined plane; and the elongate tube having an axis and a tool mounted on a distal end of the tube, the elongate tube being curved along a distal length of the elongate tube and controllably rotatable around the axis such that the tool is movable in a circle or an additional two degrees of freedom internal of the patient by rotation of the arm member.

These and other features of the invention are described in the following detailed description.

Portability

Another aspect of the invention is to provide readily manually portable components positionable in close proximity to a patient within the sterile field, without unduly reducing access to the patient or otherwise interfering with the procedure.

In one embodiment, a portable remotely controllable surgical instrument is provided including a shaft, a mounting mechanism and a drive unit. A manually portable elongated shaft is provided having a proximal end and a distal end manually positionable at an operative site within a subject upon insertion of the shaft through an incision in the subject. A manually portable mounting mechanism is readily manually mountable in a fixed position outside the patient through the incision, the proximal end of the portable shaft being mounted thereon. A manually portable drive unit is drivably interconnected through the mounting mechanism to a tool mounted at the distal end of the portable shaft. The drive unit is readily manually positionable at a selected position outside the patient.

In various embodiments, the drive unit is controllably drivable by a computer. The proximal end of the portable shaft is readily manually mountable on the portable mounting mechanism for enabling readily drivable intercoupling of the tool to the drive unit. The portable shaft may be disposable. The drive unit may be readily manually mountable at a position remote from the incision.

In another embodiment, there is provided a portable remotely controllable surgical apparatus comprising: a manually portable elongated shaft having a proximal end and a distal end manually positionable at an operative site within a subject upon insertion of the shaft through an incision in the subject; a manually portable mounting mechanism being readily manually mountable in a fixed position outside the patient near the incision, the proximal end of the portable elongated shaft being mounted thereon; a manually portable support for fixedly positioning the manually portable mounting mechanism in a selected location relative to the subject, the manually portable support being readily fixedly attachable to and detachable from a stationary structure on or relative to which the subject is mounted. A portable drive unit is preferably drivably intercoupled through the mounting mechanism to a tool mounted at the distal end of the portable shaft; wherein the drive unit is readily positionable at a selected position outside and remote from the incision. The surgical instrument may include one or more mechanically drivable components drivably intercoupled to a drive unit, the apparatus further comprising mechanical cabling drivably coupled to the one or more components at one end of the cabling, the mechanical cabling being readily drivably couplable to and decouplable from the drive unit at another end of the mechanical cabling.

In another embodiment there is provided a portable remotely controllable surgical apparatus comprising: a manually portable elongated shaft having a proximal end and a distal end manually positionable at an operative site within a subject upon insertion of the shaft through an incision in the subject; a manually portable mounting mechanism being readily manually mountable in a fixed position outside the patient near the incision, the proximal end of the portable elongated shaft being mounted thereon; a portable drive unit drivably interconnected to the portable elongated shaft through the mounting mechanism; mechanical cabling drivably coupled to the mounting mechanism at one end of the cabling and readily drivably couplable to and decouplable from the portable drive unit at another end of the cabling. The mounting mechanism typically includes one or more mechanically drivable components for moving the mounting mechanism outside the subject, the one or more mechanically drivable components being drivably interconnected to the drive unit through the mechanical cabling.

These and other features of the invention are set forth in greater detail in the following detailed description section.

User Control Apparatus

Another aspect of the invention is to provide, in a master/slave surgery system, a master station which includes upper and lower positioner assemblies, movably connected, including an arm assembly with a distal hand assembly for engagement by the surgeon's hand.

In one embodiment, a master station is adapted to be manually manipulated by a surgeon to, in turn, control motion to a slave station at which is disposed a surgical instrument. The master station includes a lower positioner assembly, an upper positioner assembly and an arm assembly. The upper positioner assembly is supported over and in rotational engagement with the lower positioner assembly to enable a lateral side-to-side surgical manipulation. An arm assembly has at its distal end a hand assembly for engagement by a surgeon's hand, and a proximal end pivotally supported from the upper positioner assembly to enable an orthogonal forward and back surgeon manipulation in a direction substantially orthogonal to the lateral surgeon manipulation.

In various preferred embodiments, the arm assembly includes a proximal arm member and a distal arm member joined by a rotational joint. A position encoder is disposed at a rotational joint detects rotation of the distal arm member. A pivotal joint connects the hand assembly to the distal end of the distal arm member, this movement being responsive to a pivotal movement of a surgeon's wrist.

The hand assembly may include a base piece with a pair of holders coupled with a base piece. One of these holder is adapted to receive a thumb and the other adapted to hold a forefinger. Each holder may comprise a metal bar positioned along the thumb or forefinger and a Velcro loop for attaching the thumb or finger to the bar. The hand assembly may further include a pair of rotating element pivotally supported from opposite ends of the base piece. One of these holders is secured to one of the rotating elements so that the surgeon can move one holder toward and away from the other holder. The pivotal joint that connects the hand assembly to the distal end of the distal arm is connected to the other rotating element, to account for rotational motion at the surgeon's wrist.

In another embodiment, a master station of a master/slave surgery system includes a base, an arm assembly pivotally supported from the base, and a hand assembly pivotally supported from the arm assembly, wherein the hand assembly includes a finger holder and a thumb holder and wherein the holders are supported for relative movement therebetween. The hand assembly may include a base piece for the holders, wherein the thumb holder is fixed in position relative to a base piece and the finger holder rotates from the base piece.

In another embodiment, a master station of a master/slave surgery system includes a base, an arm assembly pivotally supported from the base, and a hand assembly pivotally supported from the arm assembly, the hand assembly including a guide shaft adapted to be grasped by the surgeon, an actuator on the guide shaft, and a multiple rotation joint attaching the guide shaft to the arm assembly.

In yet another embodiment, a template is provided secured to the support which holds the surgical instrument, for locating the position of the support and subsequently the position of the surgical instrument, relative to the incision point of the patient. This enables an accurate placement of the instrument at an operative site internal to the patient.

These and other features of the present invention are described in greater detail in the following detailed description section.

Electronic Controls and Methodology

The invention also provides a method of controlling a surgical instrument that is inserted in a patient for facilitating a surgical procedure and controlled remotely from an input device manipulated by a surgeon at a user interface, the method comprising the steps of: initializing the position of the surgical instrument without calculating its original position, and the position of the input device under electronic control; the initializing including establishing an initial reference position for the input device and an initial reference position for the surgical instrument; calculating the current absolute position of the input device as it is manipulated by the surgeon; determining the desired position of the surgical instrument based upon: the current position of the input device, the reference position of the input device, and the reference position of the surgical instrument, and moving the surgical instrument to the desired position so that the position of the surgical instrument corresponds to that of the input device. The input device typically has position sensors, and the step of initializing includes initializing these position sensors. The initializing is preferably to zero. The method may include computing an initial reference orientation for the input device, computing a desired orientation for the surgical instrument and/or computing a desired position for the surgical instrument. The initializing step may include performing a forward kinematic computation from the input device. The method may include reading position sensor values and current time. The calculating step may include calculating both the position and orientation of the input device. The method may further include calculating the current orientation of the input device. The step of determining may include performing an inverse kinematic computation and/or a transformation into an earth coordinate system From the transformation determined joint angles and drive motor angles for the surgical instrument orientation may be determined.

In another embodiment, there is provided a method of controlling a tool of a surgical instrument that is inserted in a patient for carrying out a surgical procedure and is controlled remotely by way of a controller from an input device at a user interface, the method comprising the steps of: the input device at an initial reference configuration and under controller control; setting the surgical instrument in the patient at an initial predefined reference configuration without controller control; calculating the current absolute position of the input device; determining the desired location of the tool by a kinematic computation that accounts for at least the initial reference configuration of the input device and the current absolute position of the input device; and moving the surgical instrument to the desired position so that the location of the tool corresponds to that of the input device. The step of determining may also be based upon the initial reference configuration of the tool.

In another embodiment, there is provided a system for controlling an instrument that is inserted in a patient to enable a surgical procedure and controlled remotely from an input device controlled by a surgeon at a user interface, the system comprising: a base; a first link rotatably connected to the base; an elbow joint for rotatably connecting the second link to the first link; a handle; a wrist member connecting the handle to the distal end of the second link; and a controller coupled to at least the base and links and for receiving signals representative of: a rotational position of the base, a rotational position of the first link relative to the base, and a rotational position of the second link relative to the first link.

In another embodiment, there is provided a control system for an instrument that is controlled remotely from an input device, the system comprising: a forward kinematics block for computing the position of the input device; an initialization block for storing an initial reference position of the input device; an inverse kinematics block coupled from the forward kinematics block and the initialization block for receiving information from the forward kinetics block of the current input device position; and a controller block coupled from the inverse kinematics block for controlling the position of the instrument in response to manipulations at the input device. Such a control system may include a scaling block coupled between the forward kinematics block and the inverse kinematics block for scaling motions imparted at the input device. The system may also include an output from the forward kinematics block directly to the inverse kinematics block representative of current input device orientation. The system may also include a combining device coupled from the forward kinematics block and the initialization block to the scaling block for providing a signal to the inverse kinematics block representative of desired instrument position. The input device typically includes a wrist and a handle and the position of the wrist is expressed in x, y and z coordinates. The orientation of the handle is typically determined by a series of coordinate transformations. Such system may include a transformation matrix for the handle coordinate frame with respect to a reference coordinate frame, a transformation matrix $R_{wh}$ for the wrist joint coordinate with respect to a reference coordinate, and a transformation matrix $R_{hwh}$ for the handle coordinate with respect to the wrist coordinate. The transformation matrix $R_h$ for the handle coordinate with respect to the reference coordinate may be $R_h = R_{wh} R_{hwh}$.

In another embodiment there is provided a method of controlling a medical implement remotely from an input device that is controlled by an operator, the method comprising the steps of: positioning the medical implement at an initial start position at an operative site for the purpose of facilitating a medical procedure; establishing a fixed position reference coordinate representative of the initial start position of the medical implement based upon a base point of the implement and an active point of the implement being in a known relative dimensional configuration, positioning the input device at an initial start position; establishing a fixed position reference coordinate representative of the initial start position of the input device; calculating the current position of the input device as it is controlled; determining the desired position of the medical implement based upon; the current position of the input device, the fixed position reference coordinate of the input device, and the fixed position reference coordinate of the medical implement, and moving the medical implement to the desired position so that the position of the medical implement corresponds to that of the input device.

In another embodiment there is provided a method of controlling a surgical instrument remotely from an input device and by way of an electronic controller, the method comprising the steps of: inserting the surgical instrument through an incision in the patient so as to dispose the distal end of the instrument at an initial start position; establishing a fixed position reference coordinate system corresponding to a fixed known position on the surgical instrument at the initial start position of the surgical instrument; positioning the input device at an initial start position; establishing a fixed position reference coordinate system representative of the initial start position of the input device; calculating the current absolute position of the input device as it is controlled; determining the desired position of the surgical instrument based upon the current absolute position of the input device, and the fixed position reference coordinate system for the respective surgical instrument and input device; and moving the surgical instrument to the desired position so that the position of the surgical instrument corresponds to that of the input device.

The invention also provides a program of instructions for the processor which include: receiving an insertion length of a medical instrument inserted in a patient; and determining a distal end location of the instrument at a target site in the patient from the insertion length. The instrument typically has a straight proximal portion and curved distal portion, lies in a single plane and is a rigid guide member. The instrument is typically inserted and then fixed at a pivot axis outside the patient. The pivot axis is generally aligned with an insertion point at which the instrument is inserted into the patient. The program of instructions may include determining a subsequent location of the distal end associated with pivoting about the pivot axis. The program of instructions may include determining a subsequent location of the distal end associated with axial rotation of the instrument, determining a subsequent location of the distal end associated with linear translation along a length axis of the instrument and/or determining a subsequent movement of the distal end in a single plane about the pivot axis. The pivotal axis is typically a reference point used by the program of instructions in determining subsequent movement of the distal end.

The invention also provides a processor and a memory device containing a program of instructions for the processor which include: receiving a coordinate representative of the desired location of the distal end of a medical instrument at a target site in a patient; and determining from the coordinate an insertion length for the medical instrument so as to locate the distal end at the target site.

These and other features of the present invention are described in greater detail in the following detailed description section.

DESCRIPTION OF DRAWINGS

FIGS. 1A–1C are three views of a flexible cannula for use with the embodiment of FIG. 1;

FIG. 8 is a perspective view of the slave station;

FIG. 8A is a perspective view of an alternative adjustable clamp member at the slave station;

FIG. 8D is a perspective view of a template used with this embodiment;

FIG. 8E is a schematic cabling diagram illustrating one cable arrangement used to operate a tool;

FIG. 8G is a schematic perspective view similar to that illustrated in FIG. 8F but specifically showing the cabling construction;

FIG. 8H is a partially broken away front elevational view as taken along line 8H—8H of FIG. 8F;

FIG. 8I is a top plan cross-sectional view taken along line 8I—8I of FIG. 8H;

FIG. 8J is a further cross-sectional top plan view as taken along line 8J—8J of FIG. 8H;

FIG. 8K is a cross-sectional side view as taken along line 8K—8K of FIG. 8H;

FIG. 9 is a view at the slave station taken along line 9—9 of FIG. 8;

FIG. 10 is a side elevation view at the slave station taken along line 10—10 of FIG. 9;

FIG. 11 is a perspective view at the slave station;

FIG. 11A is a cross-sectional view as taken along line 11A—11A of FIG. 11;

FIG. 11B is a cross-sectional view as taken along line 11B—11B of FIG. 11A;

FIG. 11C is a cross-sectional view as taken along line 11C—11C of FIG. 11A;

FIG. 12 is a cross-sectional view as taken along line 12—12 of FIG. 11;

FIG. 16E is a perspective view of an alternate embodiment of the tool and wrist construction;

FIG. 16F is an exploded perspective view of the construction illustrated in FIG. 16E;

FIG. 16G is a fragmentary perspective view showing a portion of the bending section;

FIG. 16H is a plan view of the flexible wrist member associated with the construction of FIGS. 16E–16G.

FIG. 16I is a perspective view of still another embodiment of a flexible end tool;

FIG. 16J is an exploded perspective view of the construction illustrated in FIG. 16I;

FIG. 16K is a fragmentary perspective view showing further details of the bending section;

DETAILED DESCRIPTION

A. Overview of Surgical Robotic System (FIGS. 1–2)

An embodiment of a surgical robotic system of the present invention is illustrated in the accompanying drawings. The described embodiment is preferably used to perform minimally invasive surgery, but may also be used for other procedures such as endoscopic or open surgical procedures.

Figure 1:
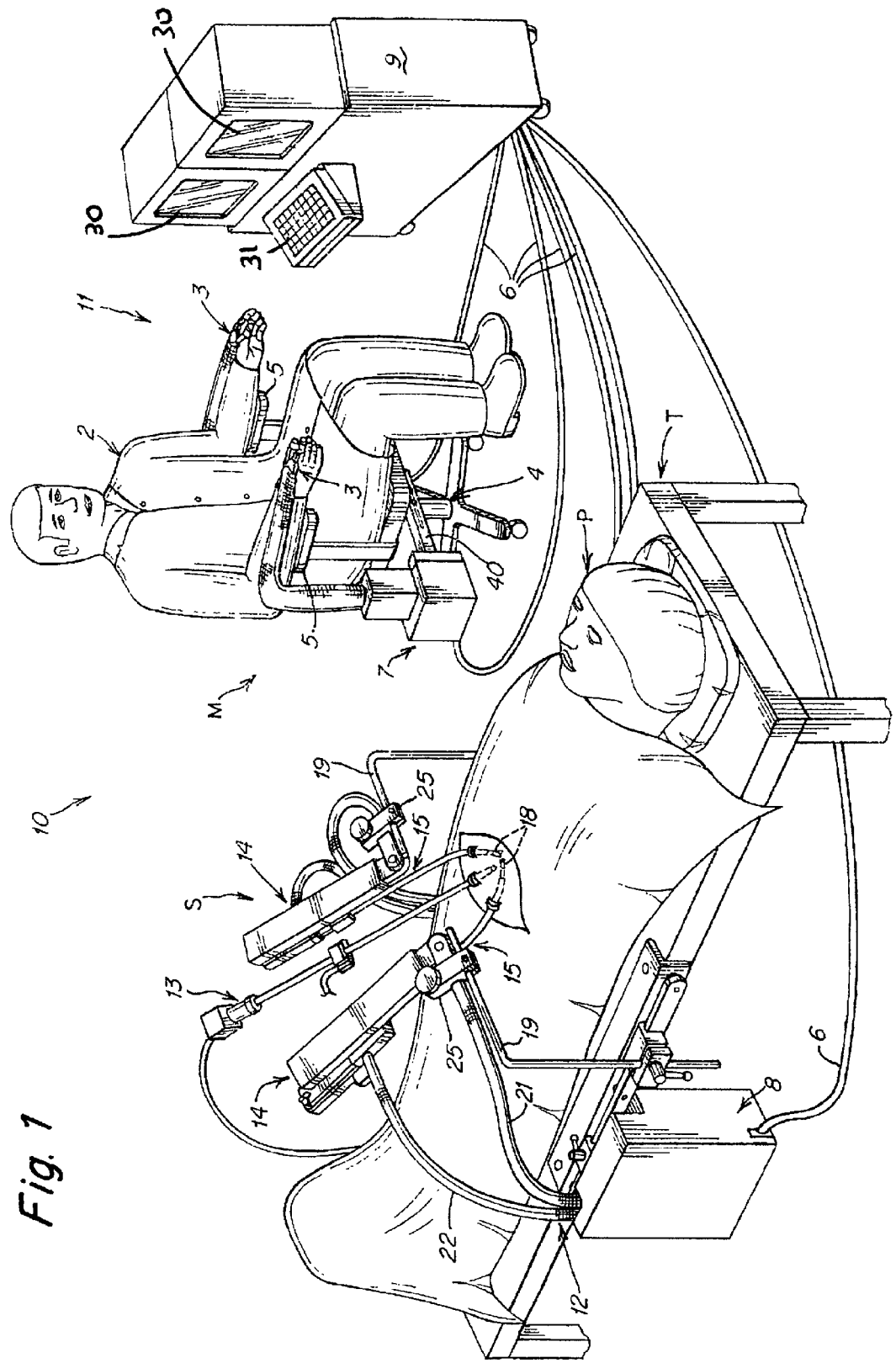
FIG. 1 is a perspective view illustrating one embodiment of the robotic system of the present invention.

FIG. 1 illustrates a surgical instrument system 10 that includes a master station M at which a surgeon 2 manipulates a pair of input devices 3, and a slave station S at which is disposed a pair of surgical instruments 14. The surgeon is seated in a comfortable chair 4 with his forearms resting upon armrests 5. His hands manipulate the input devices 3 which cause a responsive movement of the surgical instruments 14.

A master assembly 7 is associated with the master station M and a slave assembly 8 is associated with the slave station S. Assemblies 7 and 8 are interconnected by cabling 6 to a controller 9. Controller 9 has one or more display screens enabling the surgeon to view a target operative site, at which is disposed a pair of tools 18. The controller further includes a keyboard for inputting commands or data.

As shown in FIG. 1, the slave assembly 8, also referred to as a drive unit, is remote from the operative site and is positioned outside of the sterile field. In this embodiment, the sterile field is defined above the plane of the top surface of the operating table T, on which is placed the patient P. The drive unit 8 is controlled by a computer system, part of the controller 9. The master station M may also be referred to as a user interface, whereby commands issued at the user interface are translated by the computer into an electrical signal received by drive unit 8. Each surgical instrument 14, which is tethered to the drive unit 8 through mechanical cabling, produces a desired responsive motion.

Thus, the controller 9 couples the master station M and the slave station S and is operated in accordance with a computer program or algorithm, described in further detail later. The controller receives a command from the input device 3 and controls the movement of the surgical instrument in a manner responsive to the input manipulation.

With further reference to FIG. 1, associated with the patient P are two separate surgical instruments 14, one on either side of an endoscope 13. The endoscope includes a camera mounted on its distal end to remotely view the operative site. The dashed line circle in FIG. 2B, labeled OS, is an example of the operative site). A second camera may be positioned away from the site to provide an additional perspective on the medical procedure or surgical operation. It may be desirable to provide the endoscope through an orifice or incision other than the one used by the surgical instrument. Here three separate incisions are shown, two for the surgical instruments 14, 14 and a centrally disposed incision for the viewing endoscope 13. A drape over the patient has a single opening for the three incisions.

Each of the two surgical instruments 14 is generally comprised of two basic components, an adaptor or guide member 15 and an instrument insert or member 16. The adaptor 15 is a mechanical device, driven by an attached cable array from drive unit 8. The insert 16 extends through the adaptor 15 and carries at its distal end the surgical tool 18. Detailed descriptions of the adapter and insert are found in later drawings.

Although reference is made to "surgical instrument" it is contemplated that this invention also applies to other medical instruments, not necessarily for surgery. These would include, but are not limited to catheters and other diagnostic and therapeutic instruments and implements.

In FIG. 1 there is illustrated cabling 12 coupling the instrument 14 to the drive unit 8. The cabling 12 is readily attachable and detachable from the drive unit 8. The surgical adaptor 15, which supports the instrument at a fixed reference point is of relatively simple construction and may be designed for a particular surgical application such as abdominal, cardiac, spinal, arthroscopic, sinus, neural, etc. As indicated previously, the instrument insert 16 is couplable and decouplable to the adaptor 15, and provides a means for exchanging instrument inserts, with then attached tools. The tools may include, for example, forceps, scissors, needle drivers, electrocautery, etc.

Referring again to FIG. 1, the overall system 10 includes a surgeon's interface 11, computer system or controller 9, drive unit 8 and surgical instruments 14. Each surgical instrument 14 is comprised of an instrument insert 16 extending through adapter 15. During use, a surgeon manipulates the input device 3 at the surgeon's interface 11, which manipulation is interpreted by controller 9 to effect a desired motion of the tool 18 within the patient.

Each surgical instrument 14 is mounted on a separate rigid support post 19 which is illustrated in FIG. 1 as removably affixed to the side of the surgical table T. This mounting arrangement permits the instrument to remain fixed relative to the patient even if the table is repositioned. Although two instruments 14 are shown here, the invention can be practiced with more or with only a single surgical instrument.

Each surgical instrument 14 is connected to the drive unit 8 by two mechanical cabling (cable-in-conduit) bundles 21 and 22. These bundles 21 and 22 terminate at connection modules, illustrated in FIG. 8F, which are removably attachable to the drive unit 8. Although two cable bundles are used here, more or fewer cable bundles may be used. Also, the drive unit 8 is preferably located outside the sterile field as shown here, although in other embodiments the drive unit may be draped with a sterile barrier so that it may be located within the sterile field.

In a preferred technique for setting up the system, a distal end of the surgical instrument 14 is manually inserted into the patient through an incision or opening. The instrument 14 is then mounted to the rigid post 19 using a mounting bracket 25. The cable bundles 21 and 22 are then passed away from the operative area to the drive unit 8. The connection modules of the cable bundles are then engaged to the drive unit 8. One or more instrument inserts 16 may then be passed through the surgical adaptor 15, while the adapter remains fixed in position at the operative site. The surgical instrument 14 provides a number of independent motions, or degrees-of-freedom, to the tool 18. These degrees-of-freedom are provided by both the surgical adaptor 15 and the instrument insert 16.

The surgeon's interface 11 is in electrical communication with the controller 9. This electrical control is primarily by way of the cabling 6 illustrated in FIG. 1 coupling from the master assembly 7. Cabling 6 also couples from the controller 9 to the drive unit 8. The cabling 6 is electrical cabling. The drive unit 8 however, is in mechanical communication with the instruments 14 in mechanical cabling 21, 22. The mechanical communication with the instrument allows the electromechanical components to be removed from the operative region, and preferably from the sterile field.

Figure 2A:
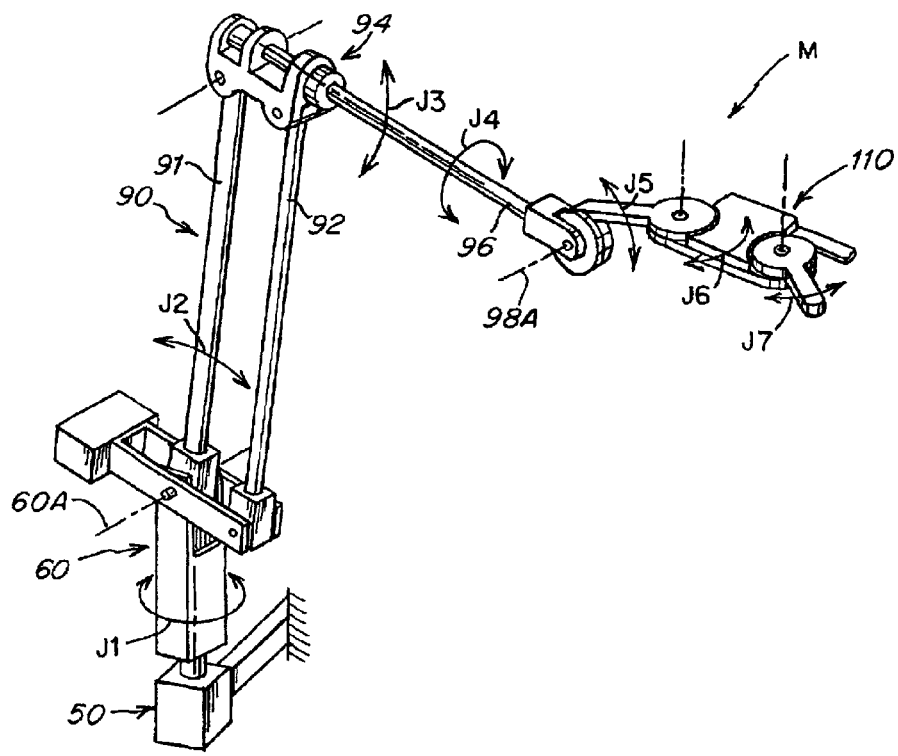
FIG. 2A is a schematic diagram illustrating the degrees-of-freedom associated with the master station.
Figure 2B:
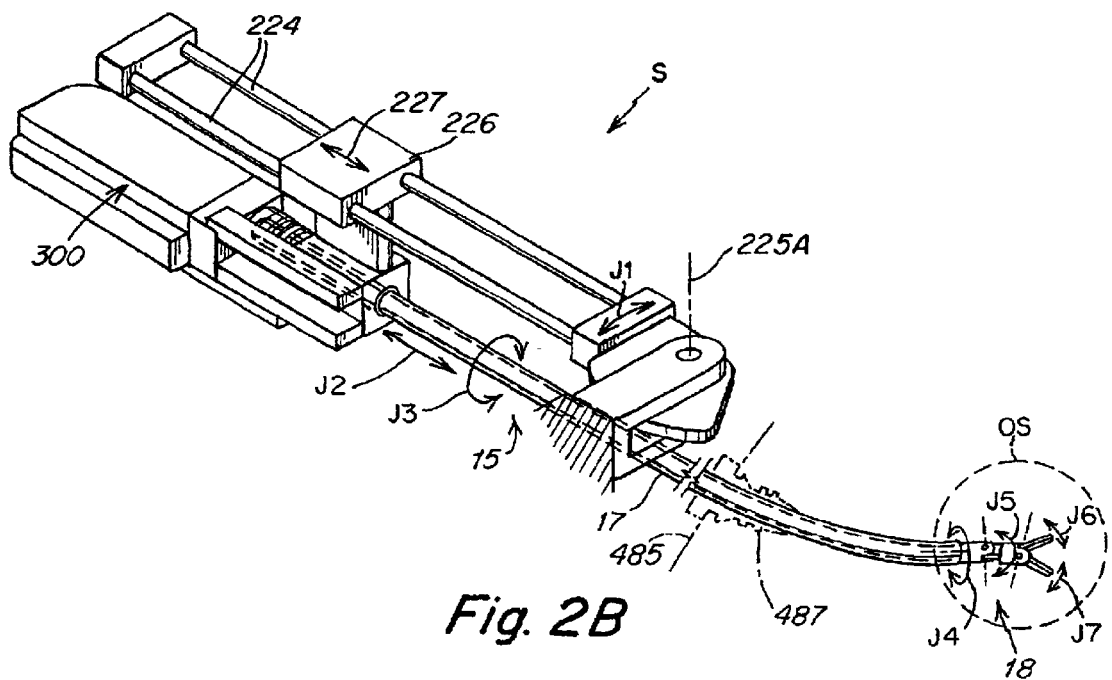
FIG. 2B is a schematic diagram illustrating the degrees-of-freedom associated with the slave station.

FIG. 2A illustrates the various movements (J1–J7) that occur at the master station M while FIG. 2B illustrates various movements (J1–J7) that occur at the slave station S. More specific details regarding FIGS. 2A and 2B are contained in a later discussion of FIGS. 3–4 (with regard to the master station of FIG. 2A) and FIGS. 8–9 (with regard to the slave station of FIG. 2B).

Figure 2C:
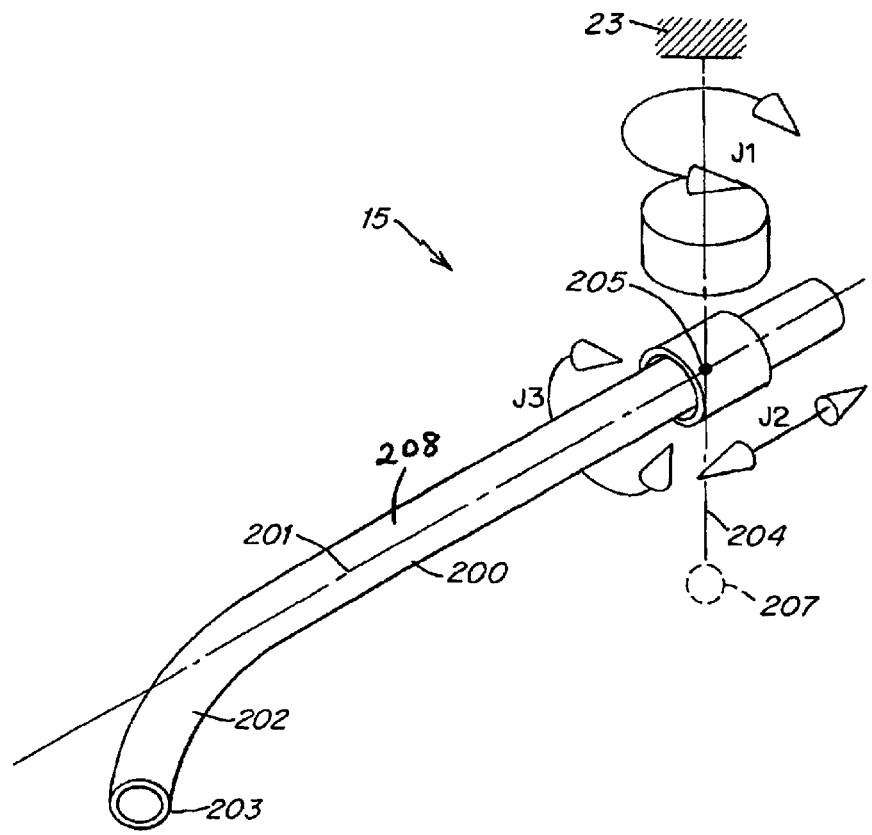
FIG. 2C shows a functional schematic diagram of the surgical adapter component of the system of FIG. 1.

FIG. 2C is a simplified representation of adaptor 15 of the slave station, useful in illustrating the three degrees-of-freedom enabled by the adapter. The adapter as shown in FIG. 2C comprises a generally rigid outer guide tube 200 (corresponding to guide tube 17 in FIG. 2B) through which an inner flexible shaft, carrying a tool 18 at its distal end, is inserted into the patient. The adapter provides three degrees-of-freedom by way of a pivotal joint J1, a linear joint J2, and a rotary joint J3. From a fixed mounting point 23 shown schematically at the top of FIG. 2C, the pivotal joint J1 allows the guide tube 200 to pivot about a fixed vertical axis 204, while maintaining the tube (both the proximal straight portion 208 and distal curved portion 202) in a single plane, transverse to pivot axis 204, in which lies central horizontal tube axis 201. The linear joint J2, moves the rigid guide tube 200 along this same axis 201. The rotary joint J3 rotates the guide tube 200 about the tube axis 201. The guide tube 200 has a fixed curve or bend 202 at its distal end 203; as a result the distal end 203 will orbit in a circle about the axis 201 when the straight portion 208 of the guide tube 200 is rotated about its axis 201. Alternatively, the three degrees-of-freedom can be achieved by a structure other than a curve 202, such as by means of a joint or angular end section. The point is to have the distal end 203 of the tube 200 at a location spaced away from the tube axis 201.

FIG. 2C thus shows a schematic view of the three degrees of freedom of the rigid curved guide tube 200. In summary, via the pivot 205 the guide tube 200 may rotate in a direction J1 about an axis 204. The guide tube 200 may also slide in an axial direction J2 along proximal tube axis 201 (via the linear slider) and rotate in a direction J3 about the proximal tube axis 201 (via a rotatable mounting at the guide tube housing). It is intended that the point 205 at which the axes of linear movement and rotation 201 and 204 intersect, be in linear alignment (along axis 204) with the incision point illustrated in dotted outline at 207, at which the guide tube enters the patient. Positioning the incision 207 in substantially vertical linear alignment with point 205 results in less trauma to the patient in the area around the incision, because movement of the guide tube 17 near the point 205 is limited.

In addition to the three degrees-of-freedom provided by the guide tube 17, the tool 18 may have three additional degrees-of-freedom. This is illustrated schematically in FIG. 2D which shows an inner flexible shaft 309, fixed at its proximal end 300, having a straight proximal portion 301 and having a curved distal portion 302 with a tool 18 mounted at the distal end. The shaft 309 has a wrist joint that rotates about axis 306. A pair of pinchers 304, 305 independently rotate as shown (J6 and J7) about horizontal axis 308 to open and close (e.g., to grasp objects). Still further, the inner shaft can be rotated (J4) about the central axis of proximal portion 301.

In practice, an instrument insert 16 (carrying the inner shaft 309) is positioned within the adaptor 15 (including guide tube 17), so that the movements of the insert are added to those of the adaptor. The tool 18 at the distal end of insert 16 has two end grips 304 and 305, which are rotatably coupled to wrist link 303, by two rotary joints J6 and J7. The axis 308 of the joints J6 and J7 are essentially collinear. The wrist link 303 is coupled to a flexible inner shaft 302 through a rotary joint J5, whose axis 306 is essentially orthogonal to the axis 308 of joints J6 and J7. The inner shaft 309 may have portions of differing flexibility, with distal shaft portion 302 being more flexible than proximal shaft portion 301. The more rigid shaft portion 301 is rotatably coupled by joint J4 to the instrument insert base 300. The axis of joint J4 is essentially co-axial with the rigid shaft 301. Alternatively, the portions 301 and 302 may both be flexible.

Through the combination of movements J1–J3 shown in FIG. 2C, the adaptor 15 can position the curved distal end 203 of guide tube 200 to any desired position in three-dimensional space. By using only a single pivotal motion (J1), the motion of the adaptor 15 is limited to a single plane. Furthermore, the fixed pivot axis 204 and the longitudinal axis 201 intersect at a fixed point 205. At this fixed point 205, the lateral motion of the guide tube 200 is minimal, thus minimizing trauma to the patient at the aligned incision point 207.

Figure 2D:
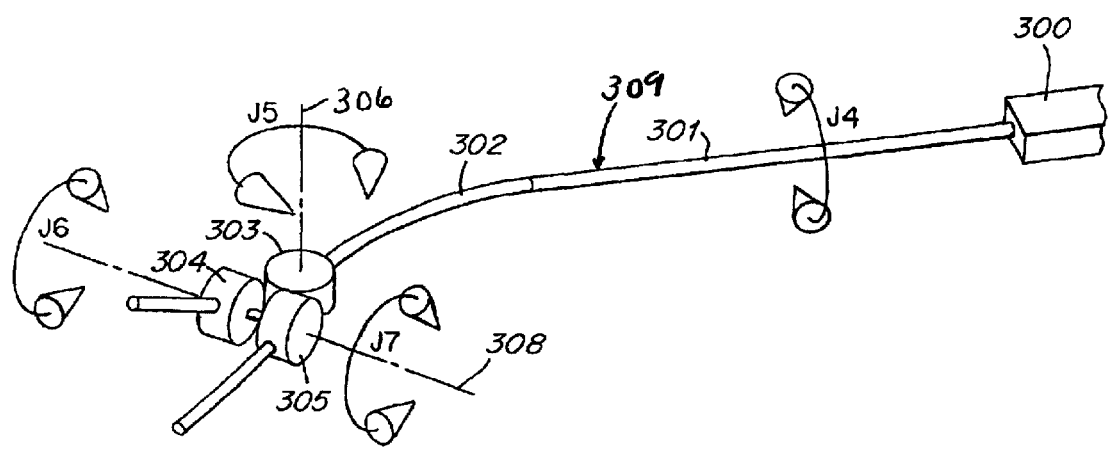
FIG. 2D shows a functional schematic diagram of the instrument insert component of the system of FIG. 1.

The combination of joints J4–J7 shown in FIG. 2D allow the instrument insert 16 to be actuated with four degrees-of-freedom. When coupled to the adaptor 15, the insert and adaptor provide the instrument 14 with seven degrees-of-freedom. Although four degrees-of-freedom are described here for the insert 16, it is understood that greater and fewer numbers of degrees-of-freedom are possible with different instrument inserts. For example an energized insert with only one gripper may be useful for electro-surgery applications, while an insert with an additional linear motion may provide stapling capability.

FIG. 2B shows in dotted outline a cannula 487, through which the guide tube 17 is inserted at the incision point. Further details of the cannula are illustrated in FIGS. 1A–1C. FIG. 1A is a longitudinal cross-sectional view showing a cannula 180 in position relative to, for example, an abdominal wall 190 of the patient. FIG. 1B is a schematic view of the guide tube 17 being inserted through the flexible cannula 180. FIG. 1C is a schematic view of the guide tube inserted so that the proximal straight section of the tube is positioned at the incision point within the cannula, with the curved distal end of the guide tube and tool 18 disposed at a target or operative site.

The cannula 180 includes a rigid base 182 and a flexible end or stem 184. The base may be constructed of a rigid plastic or metal material, while the stem may be constructed of a flexible plastic material having a fluted effect as illustrated in FIGS. 1A–1C. The length of the base is short enough that the curve in the guide tube can easily pass through a center passage or bore 186 in the base 182. The bore 186 has a larger diameter than the outer diameter of the guide tube 17 to facilitate passage of the guide tube through the cannula 180. A diaphragm or valve 188 seals the guide tube 17 within the cannula 180.

FIG. 1A shows a cap 192 secured to the proximal end of the base 182 by one or more o-rings 194. Before the guide tube 17 is inserted in cannula 180, a plug 196 may be inserted to seal the proximal end of the base 182. The plug 196 is secured by a tether 198 to base 182.

In the context of an insertable instrument system, there may generally be distinguished two types of systems, flexible and rigid. A flexible system would use a flexible shaft, which may be defined as a shaft atraumatically insertable in a body orifice or vessel which is sufficiently pliable that it can follow the contours of the body orifice or vessel without causing significant damage to the orifice or vessel. The shaft may have transitions of stiffness along its length, either due to the inherent characteristics of the material comprising the shaft, or by providing controllable bending points along the shaft. For example, it may be desirable to induce a bend at some point along the length of the shaft to make it easier to negotiate a turn in the body orifice. A mechanical bending of the tube may be caused by providing one or more mechanically activatable elements along the shaft at the desired bending point, which a user remotely operates to induce the bending upon demand. The flexible tube may also be caused to bend by engagement with a body portion of greater stiffness, which may, for example, cause the tube to bend or loop around when it contacts the more stiffer body portion. Another way to introduce a bend in the flexible shaft is to provide a mechanical joint, such as the wrist joint provided adjacent to tool 18 as previously described, which, as discussed further, is mechanically actuated by mechanical cabling extending from a drive unit to the wrist joint.

One potential difficulty with flexible shafts or tubes as just described is that it can be difficult to determine the location of any specific portion or the distal end of such shaft or tube within the patient. In contrast, what is referred to as a rigid system may utilize a rigid guide tube 17 as previously described, for which the position of the distal end is more easily determined, simply based upon knowing the relevant dimensions of the tube. Thus, in the system previously described, a fixed pivot point (205 in FIG. 2C) is aligned with an incision point 207. One can determine the position of the rigid guide tube 17, knowing the length from the fixed point to the distal end of the guide tube, which is fixed and predetermined based upon the rigid nature of the guide tube, and the known curvature of the distal end of the guide tube. The point of entry or incision point serves as a pivot point, for which rotation J1 of the guide tube about the fixed axes 204 is limited to maintaining the proximal end of the guide tube in a single plane.

Furthermore, by inserting the more flexible shaft, carrying a tool 18 at its distal end, within the rigid guide tube, the rigid guide tube in effect defines a location of the flexible shaft and its distal end location tool 18.

Also relevant to the present invention is the use of the term "telerobotic" instrument system, in which a physician or medical operator is manually manipulating some type of hand tool, such as a joy stick, and at the same time is looking at the effect of such manual manipulation on a tool which is shown on a display screen, such as a television or a video display screen, accessible to the operator. The operator then can adjust his manual movements in response to visual feedback he receives by viewing the resulting effect on the tool, shaft guide tube, or the like, shown on the display screen. It is understood that the translation of the doctor's manual movement, via a computer processor which feeds a drive unit for the inserted instrument, is not limited to a proportional movement, rather, the movement may be scaled by various amounts, either in a linear fashion or a nonlinear fashion. The scaling factor may depend on where the instrument is located or where a specific portion of the instrument is located, or upon the relative rate of movement by the operator. The computer controlled movement of the guide tube or insert shaft in accordance with the present invention, enables a higher precision or finer control over the movement of the instrument components within the patient.

In practice, the physician, surgeon or medical operator would make an incision point, inserting the flexible cannula previously shown. He would then manually insert the rigid curved guide tube until the distal point of the guide tube was positioned at the operative site. With the guide tube aligned in a single plane, the operator would clamp the guide tube at the support bracket 25 on post 19, to establish the fixed reference pivot point, (205 in FIG. 2C), with the incision point axially aligned under the fixed pivot point. The operator would then manually insert the instrument insert through the guide tube until the tool 18 is extended out from the distal end of the guide tube. The wrist joint on the inner insert shaft is then positioned at a known point, based upon the known length and curvature of the rigid guide tube and distance along that length at which the incision point is disposed. Then, a physician, surgeon or medical operator located at the master station can manually adjust the hand assembly to cause a responsive movement of the inserted instrument. The computer control decides what the responsive movement at the instrument is, including one or more of movement of the guide tube, the whole instrument 14, or the flexible inner shaft or the tool at its distal end. A pivotal movement J1 will rotate the proximal end of the guide tube, causing pivoting of the whole instrument 14. An axial movement J2 of the whole instrument 14 will reposition the instrument in the single plane. A rotational movement J3 of just the guide tube results in the end of the guide tube and end of the inner shaft being taken out of the plane, following a circular path or orbit in accordance with rotation of the guide tube shaft. These three movements J1, J2 and J3 are defined as setting the position of the wrist joint 303 of the tool.

The other three movements J4–J7, are defined as setting the orientation of the instrument insert, and more specifically, a direction at which the tool is disposed with respect to the wrist joint. Central mechanical cables in the inner shaft cause motions J5–J7, J5 being the wrist movement and J6–J7 being the jaw movement of the tool. The J4 movement is for rotation of the inner shaft by its proximal axis, within the guide tube. These relative movements, and the position and orientation of the instrument insert, will be further described in a later discussion of an example of the computer algorithm for translating the movement at the master station to a movement at the slave station.

B. The Master Station M (FIGS. 3–7)

Figure 3:
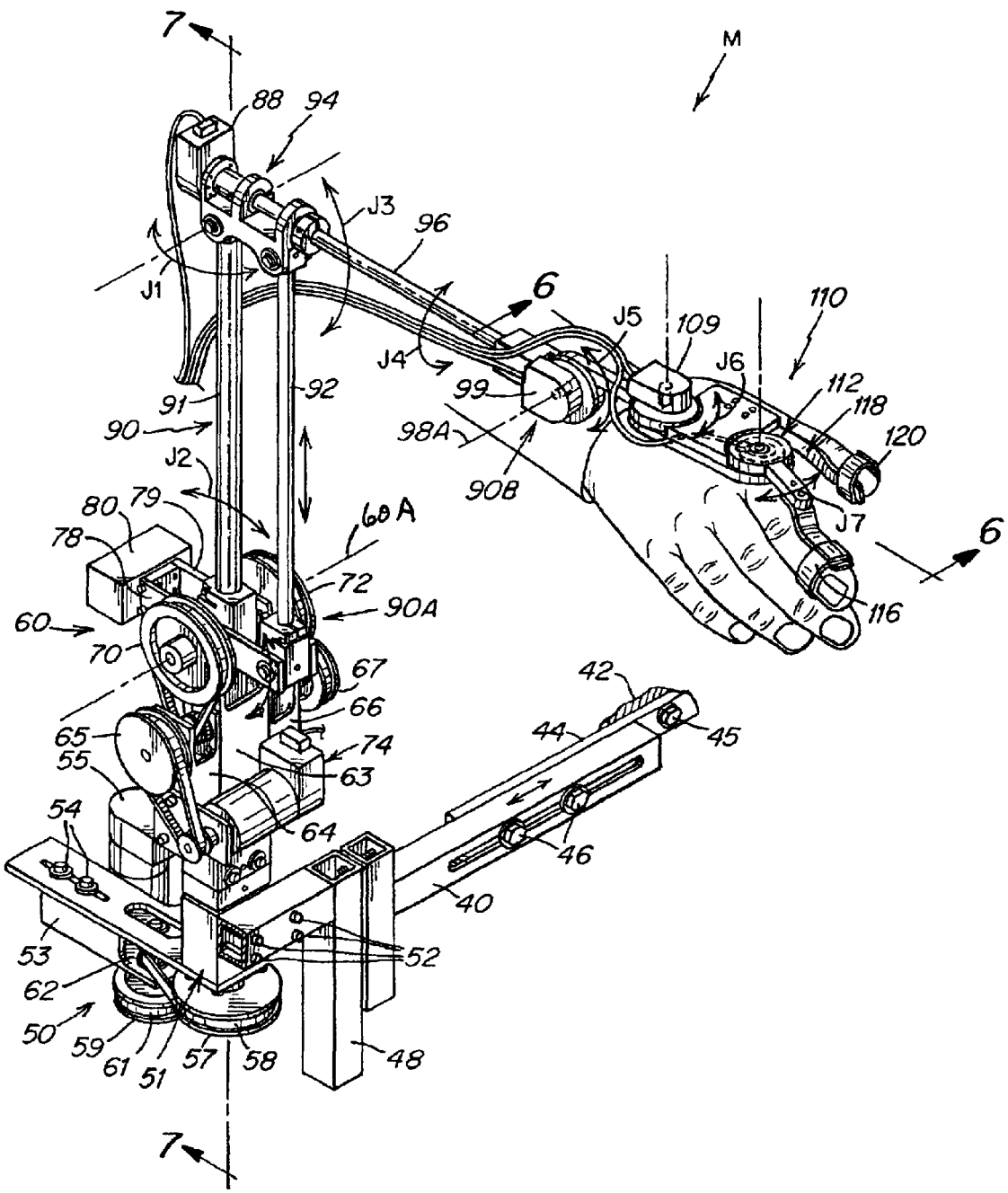
FIG. 3 is a perspective view of the positioner assembly at the master station.

At the master station M illustrated in FIG. 1 and shown in further detail in FIG. 3, there are two sets of identical hand controls, one associated with each hand of the surgeon. The outputs of both controls are fed to assembly 7, which is secured to the surgeon's chair 4 by a cross-brace 40. In FIG. 3, the brace 40 is shown secured to the chair frame 42 by means of adaptor plate 44 and bolts 45. Additional bolts 46, with associated nuts and washers secure the cross-brace 40 in a desired lateral alignment (see double headed arrow) along the adaptor plate 44. Additional bolts 49 (see FIG. 4) are used for securing the cross-brace 40 with a base piece 48. The base piece 48 supports lower and upper positioner assemblies, as will now be described.

A lower positioner assembly 50 is supported from the base piece 48. An upper positioner assembly 60 is supported above and in rotational engagement (see arrow J1 in FIGS. 2A and 4), in a substantially horizontal plane with the lower positioner assembly. This rotational movement J1 enables a lateral or side-to-side manipulation by the surgeon. An arm assembly 90, having a lower proximal end 90A, is pivotally supported (J2) from the upper positioner assembly 60 about a substantially horizontal axis 60A (see FIGS. 2A and 3) to enable substantially vertical surgeon manipulation. The arm assembly 90 has an upper distal end 90B (FIG. 3), carrying a hand assembly 110.

Figure 4:
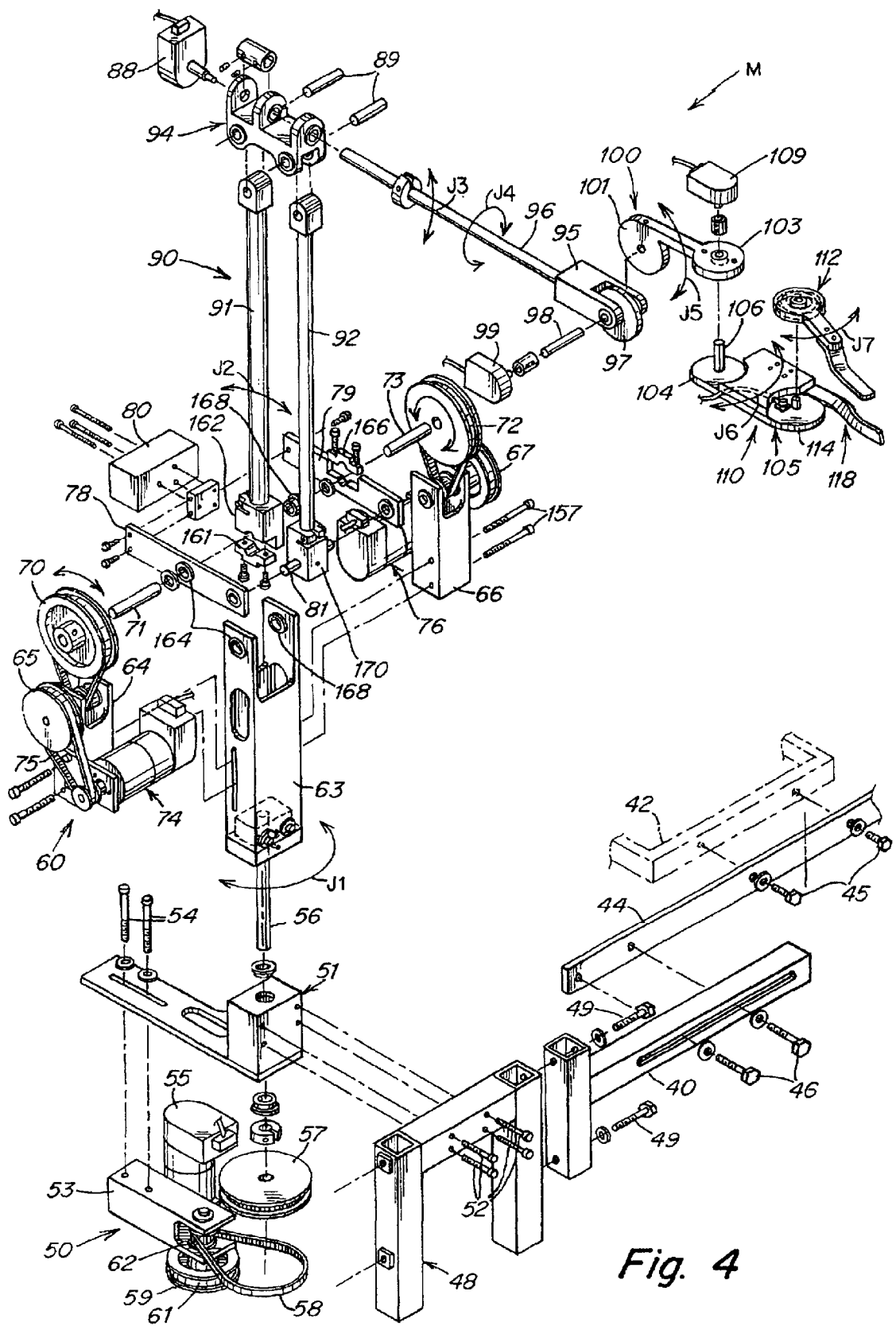
FIG. 4 is an exploded perspective view also of the positioner assembly at the master station.

As shown in FIG. 4, the lower positioner assembly 50 includes a base member 51 that is secured to the base piece 48 by bolts 52. It also includes a bracket 53 that is secured to the base member 51 by means of bolts 54. The bracket 53 supports a motor/encoder 55. A vertical shaft 56 that extends from the upper positioner assembly 60 to the base member 51, extends through a passage in the base member 51 and is secured to a pulley 57 disposed under the base member 51. A belt 58 engages with pulley 57 and with a further pulley 62 supported from the bracket 53. This further pulley 62 is on a shaft that engages a pulley 59. A further belt 61 intercouples pulley 59 to the shaft of the motor/encoder 55.

In FIGS. 3 and 4, the base member 51 and bracket 53 are stationary; however, upon rotation about J1, drive is applied to the pulleys 57 and 59 thus applying drive to the motor/encoder 55. This detects the position and movement from one position to another of the upper positioner assembly 60 relative to the lower positioner assembly 50.

The upper positioner assembly 60 has a main support bracket 63, supporting on either side thereof side support brackets 64 and 66. Side bracket 64 supports a pulley 65, while side bracket 66 supports a pulley 67. Above pulley 65 is another pulley 70, while above pulley 67 is another pulley 72. Pulley 70 is supported on shaft 71, while pulley 72 is supported on shaft 73.

Also supported from side support bracket 64 is another motor/encoder 74, disposed on one side of the main support bracket 63. On the other side of bracket 63 is another motor/encoder 76, supported from side support bracket 66. Motor/encoder 74 is coupled to the shaft 71 by pulleys 65 and 70 and associated belts, such as the belt 75 disposed about pulley 65. Similarly, motor/encoder 76 detects rotation of the shaft 73 through pulleys 67 and 72 by way of two other belts. The pulley 65 is also supported on a shaft coupling to pulley 70 supported by side support bracket 64. A further belt goes about pulley 70 so there is continuity of rotation from the shaft 71 to the motor/encoder 74. These various belts and pulleys provide a movement reduction ratio of, for example, 15 to 1. This is desirable so that any substantial movements at the master station are translated as only slight movements at the slave station, thereby providing a fine and controlled action by the surgeon.

Extending upwardly from main support bracket 63, is arm assembly 90 which includes a pair of substantially parallel and spaced apart upright proximal arms 91 and 92, forming two sides of a parallelogram. Arm 91 is the main vertical arm, while arm 92 is a tandem or secondary arm. The bottoms of arms 91 and 92 are captured between side plates 78 and 79. The secondary arm 92 is pivotally supported by pin 81 (see FIG. 4) from the forward end of the side plates 78 and 79. The main arm 91 is also pivotally supported between the side plates 78 and 79, but is adapted to rotate with the shaft 71. Thus, any forward and back pivoting J2 of the arm 91 is sensed through the shaft 71 down to the motor/encoder 74. This movement J2 in FIGS. 2A and 4 translates the forward and rearward motion at the surgeon's shoulder.

The side plates 78 and 79 pivot on an axis defined by shafts 71 and 73. However, the rotation of the plates 78 and 79 are coupled only to the shaft 73 so that pivotal rotation, in unison, of the side plates 78 and 79 is detected by motor/encoder 76. This action is schematically illustrated in FIGS. 2A and 4 by J3. Movement J3 represents an up and down motion of the surgeon's elbow. A counterweight 80 is secured to the more rear end of the side plates 78 and 79, to counter-balance the weight and force of the arm assembly 90.

As depicted in FIGS. 3 and 4, the tops of the arms 91 and 92 are pivotally supported in a bracket 94 by two pivot pins 89. The bracket 94 also supports a distal arm 96 of the arm assembly 90. The rotation of distal arm 96 is sensed by an encoder 88. Thus, the distal arm 96 is free to rotate J4 about its longitudinal axis, relative to the arms 91 and 92. This rotation J4 translates the rotation of the surgeon's forearm.

The distal end of distal arm 96 is forked, as indicated at 95 in FIG. 4. The forked end 95 supports disc 97 in a fixed position on shaft 98. The disc 97 is fixed in position while the shaft 98 rotates therein; bearings 93 support this rotation. The shaft 98 also supports one end of pivot member 100, which is part of hand assembly 110. The pivot member 100 has at its proximal end a disc 101 that is supported co-axially with the disc 97, but that rotates relative to the fixed disc 97 (see FIGS. 5 and 6). This rotation is sensed by an encoder 99 associated with shaft 98. The disc end 101 of the pivot member 100 defines the rotation J5 in FIG. 4, which translates the wrist action of the surgeon, particularly the up and down wrist action.

The pivot member 100 has at its other end a disc 103 that rotates co-axially with a disc end 104 of hand piece 105. There is relative rotation between disc 103 and disc 104 about a pivot pin 106 (see FIGS. 4 and 6). This relative rotation between the pivot member 100 and the hand piece 105 is detected by a further encoder 109 associated with discs 103 and 104. This action translates lateral or side to side (left and right) action of the surgeon's hand.

At the very distal end of the master station is a forefinger member 112 that rotates relative to end 114 of the hand piece 105. As indicated in FIG. 3, the forefinger piece 112 has a Velcro loop 116 for holding the surgeon's forefinger to the piece 112. Also extending from the hand piece 105 is a fixed position thumb piece 118, with an associated Velcro loop 120. In FIG. 3, motion J7 represents the opening and closing between the surgeon's forefinger and thumb.

Figure 5:
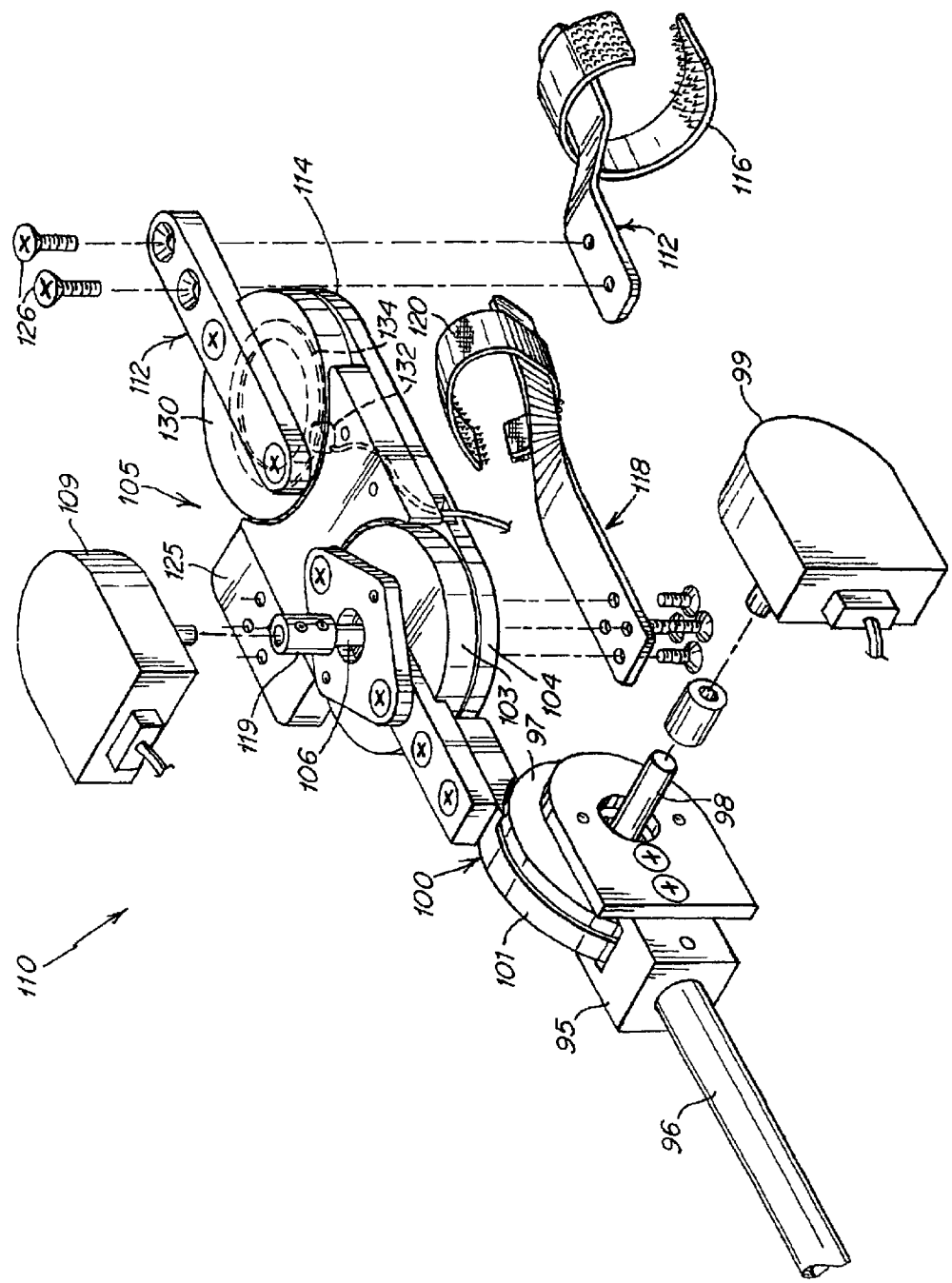
FIG. 5 is a partially exploded view of the hand assembly portion associated with the positioner assembly.

Reference is now made to FIG. 5, which shows expanded details of the distal end of the arm assembly. One end of the distal arm 96 couples to the fork 95; fork 95 supports one end of the pivot member 100. The encoder 99 detects the position of the pivot member 100 relative to the distal arm 96. The encoder 109 couples to a shaft adapter 119 and detects relative displacement between the pivot member 100 and the hand piece 105. The thumb piece 118 is secured to the side piece 125 which, in turn, is secured as part of the hand piece 105. Bolts 126 secure the finger piece 112 to the rotating disc 130. The distal end encoder 132, with encoding disc 134, detects the relative movement between the surgeon's thumb and forefinger pieces.

Figure 6:
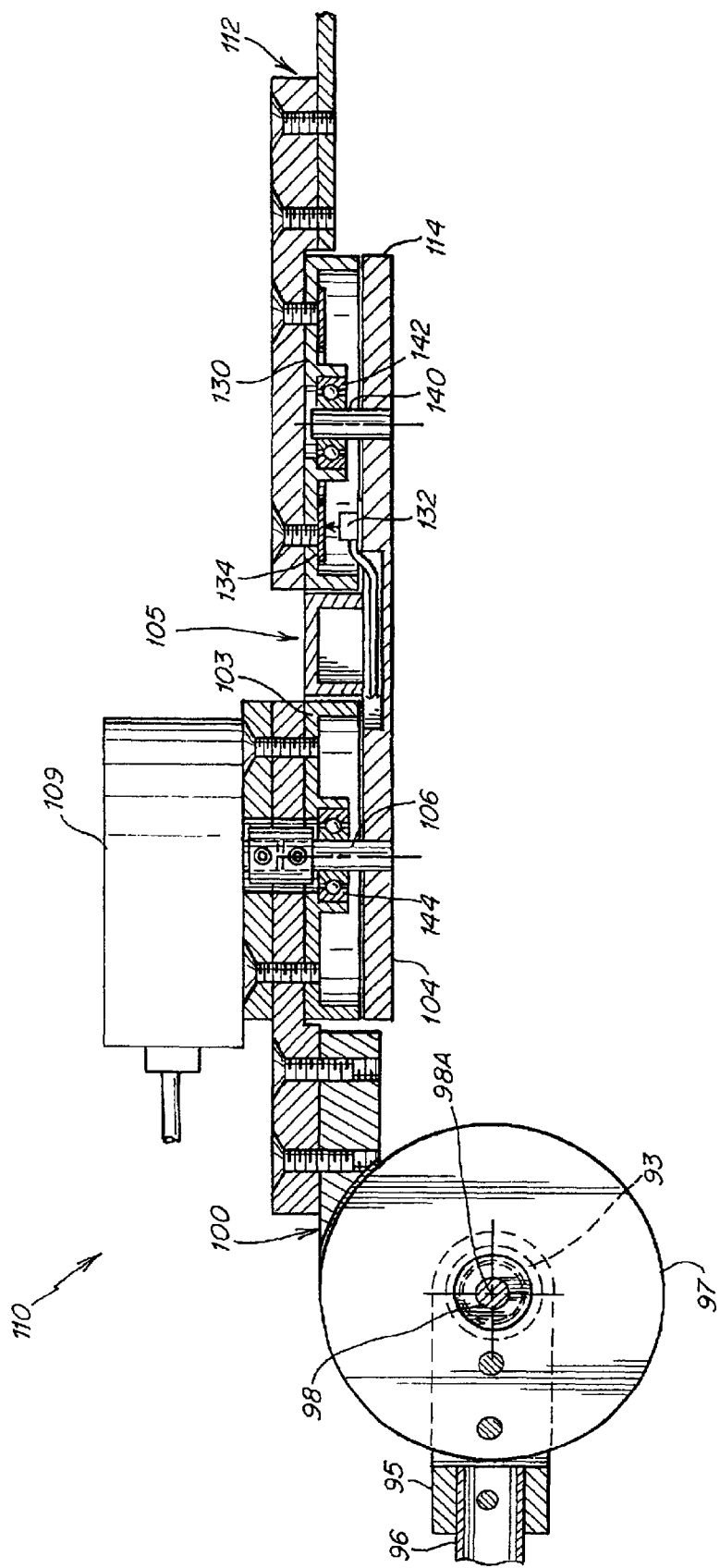
FIG. 6 is a cross-sectional view of the hand assembly as taken along line 6—6 of FIG. 3.

FIG. 6 shows further details of the distal end of the arm assembly. Pivot member 100 is attached to the distal arm 96 and the hand piece 105. Further details are shown relating to the encoder 132 and the encoder disc 134. A shaft 140, intercoupling hand piece 105 and disc 130, is supported by a bearing 142. The shaft 106 is also supported by a bearing 144.

Figure 7:
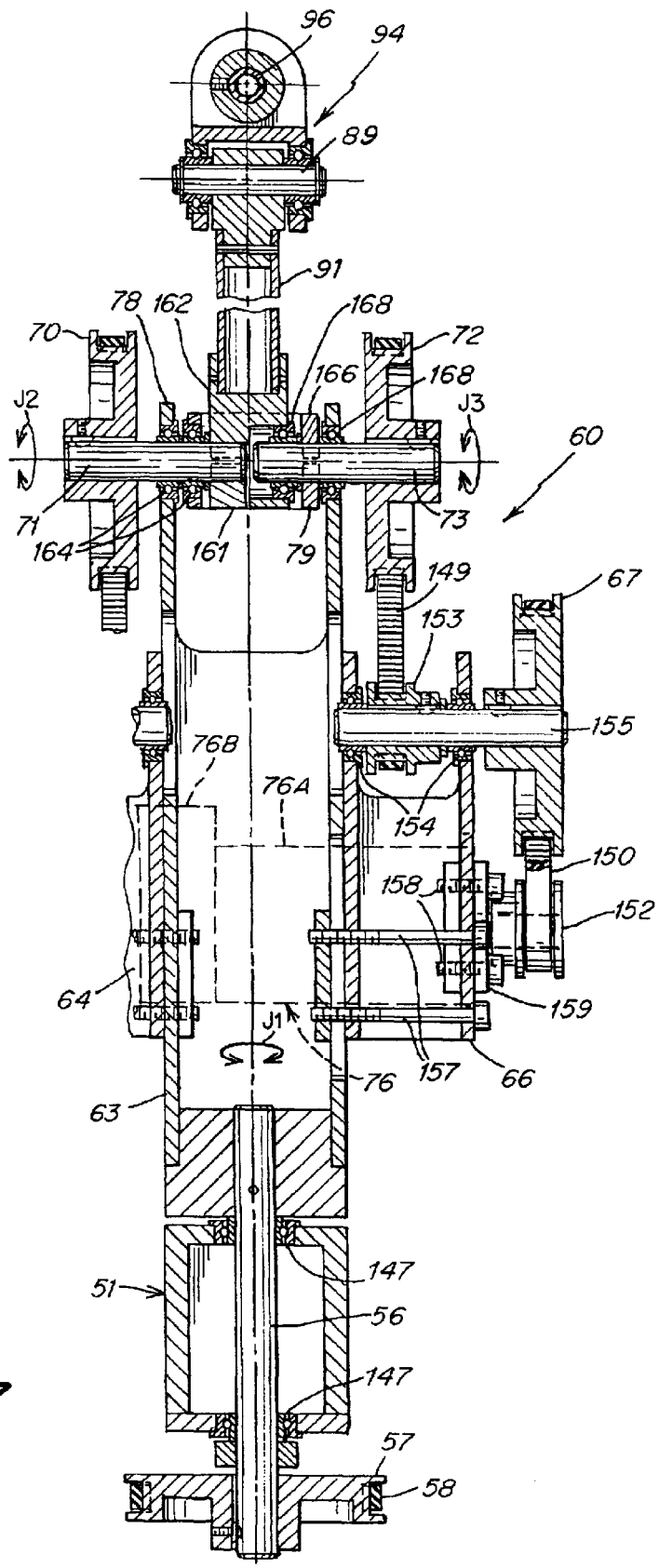
FIG. 7 is a cross-sectional view at the master station as taken along lines 7—7 of FIG. 3.

The detailed cross-sectional view of FIG. 7 is taken along lines 7—7 of FIG. 3. This illustrates the base member 51 with the pulley 57 supported thereunder by means of the shaft 56. Also illustrated are bearings 147 about shaft 56 which permit the main support bracket 63 to pivot (J1). Pulley 57 rotates therewith and its rotation is coupled to the encoder 55 for detecting the J1 rotation. FIG. 7 also illustrates the motor/encoder 76, where the separate dashed portions identify motor 76A and encoder 76B.

FIG. 7 also shows further details of the belt and pulley arrangement. For simplicity, only the pulley 67 and its associated support is disclosed. Substantially the same construction is used on the other side of the main support bracket 63 for the mounting of the opposite pulley 65. A belt 149 about pulley 72 also engages with pulley 153 fixedly supported on the shaft 155. The shaft 155 rotates relative to the fixed side support bracket 66, by way of bearings 154. The shaft 155 supports the pulley 67. A toothed belt 150 is disposed about pulley 67 to the smaller pulley 152. The pulley 152 is supported on the shaft of the motor/encoder 76. For the most part all pulleys and belts disclosed herein are toothed so that there is positive engagement and no slippage therebetween.

In order to provide adjustment of the belts 149 and 150, adjusting screws are provided. One set of adjusting screws is shown at 157 for adjusting the position of the side support bracket 66 and thus the belt 149. Also, there are belt adjusting screws 158 associated with support plate 159 for adjusting the position of the encoder and thus adjusting the belt 150.

Figure 7A:
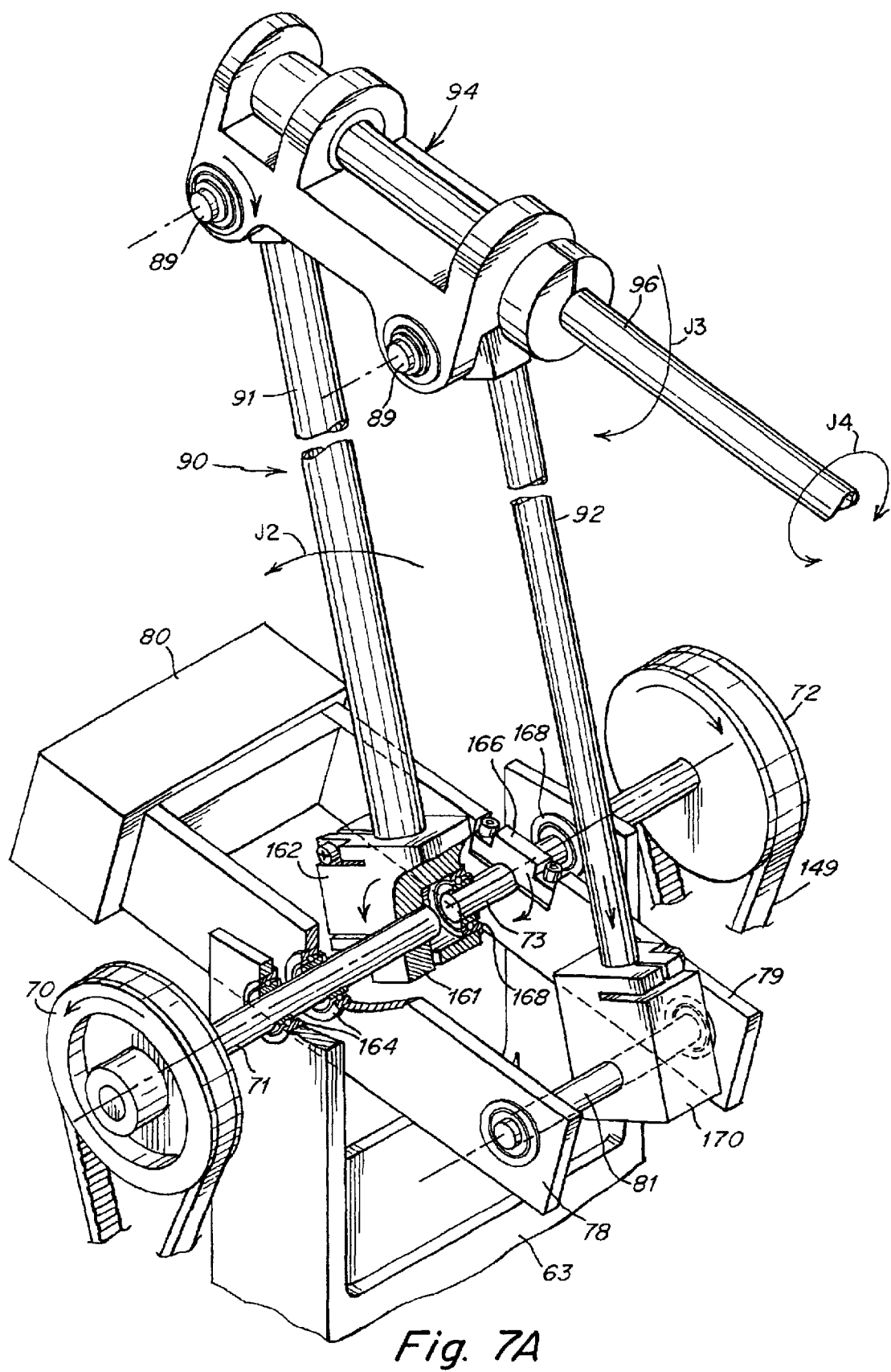
FIG. 7A is a schematic perspective view of the yoke assembly portion of the positioner assembly.

FIG. 7 also illustrates the pulleys 70 and 72 with their respective support shafts 71 and 73. FIG. 7A shows details of the pulleys 70 and 72 and their support structure. The pulley 70 is associated with motion J2. The pulley 72 is associated with motion J3. The pulley 70 and its associated shaft 71 rotate with the vertical main shaft or arm 91. The pulley 72 and its associated shaft 73 rotate independent of the arm 91 and instead rotate with the rotation of the side plates 78 and 79. One end of shaft 71 is secured with the pulley 70. The other end of the shaft 71 engages a clamp 161, which clamps the other end of the shaft to the support piece 162 of the main vertical arm 91. The shaft 71 is supported for rotation relative to the main support bracket 63 and the side plates 78, 79 by means of bearings 164.

The opposite pulley 72 and its shaft 73 are supported so that the pulley 72 rotates with rotation of the yoke formed by side plates 78 and 79. A clamp 166 clamps the shaft 73 to the side plate and thus to the rotating yoke. This yoke actually rotates with the pin of shaft 73. For further support of the shaft 73, there are also provided bearings 168, one associated with the support bracket 63 and another associated with support piece 162.

Regarding the yoke formed by side plates 78 and 79, at one end thereof is a counterweight 80, as illustrated in FIGS. 4 and 7A. The other end supports a rotating block 170 (see FIG. 4) that supports the lower end of arm 92 and has oppositely disposed ends of pin 81 rotatably engaged with that end of the yoke (side plates 78 and 79). Bushings or bearings may be provided to allow free rotation of the bottom end of the arm 92 in the yoke that captures this arm.

In practice, the following sequence of operations occur at master station M. After the instrument 14 has been placed at the proper operative site, the surgeon is seated at the console and presses an activation button, such as the "enter" button on the keyboard 31 on console 9. This causes the arms at the master station to move to a predetermined position where the surgeon can engage thumb and forefinger grips. FIG. 1 shows such an initial location where the arm assemblies 3 are essentially pointed forward. This automatic initialization movement is activated by the motors in unit 7 at the master station. This corresponds, in FIG. 2A, to upper arm 96 being essentially horizontal and lower arm 92 being essentially vertical.

While observing the position of the tools on the video display screen 30, the surgeon now positions his hand or hands where they appear to match the position of the respective tool 18 at the operative site (OS in FIG. 2B). Then, the surgeon may again hit the "enter" key. This establishes a reference location for both the slave instrument and the master controls. This reference location is discussed later with details of controller 9 and an algorithm for controlling the operations between the master and slave stations. This reference location is also essentially identified as a fixed position relative to the wrist joint at the distal end of distal arm 96 at pin 98 in FIG. 4 (axis 98A in FIG. 2A). This is the initial predefined configuration at the master station, definable with three dimensional coordinates.

Now when the surgeon is ready to carry out the procedure, a third keystroke occurs, which may also be a selection of the "enter" key. When that occurs the motors are activated in the drive unit 8 so that any further movement by the surgeon will initiate a corresponding movement at the slave end of the system.

Figure 18:
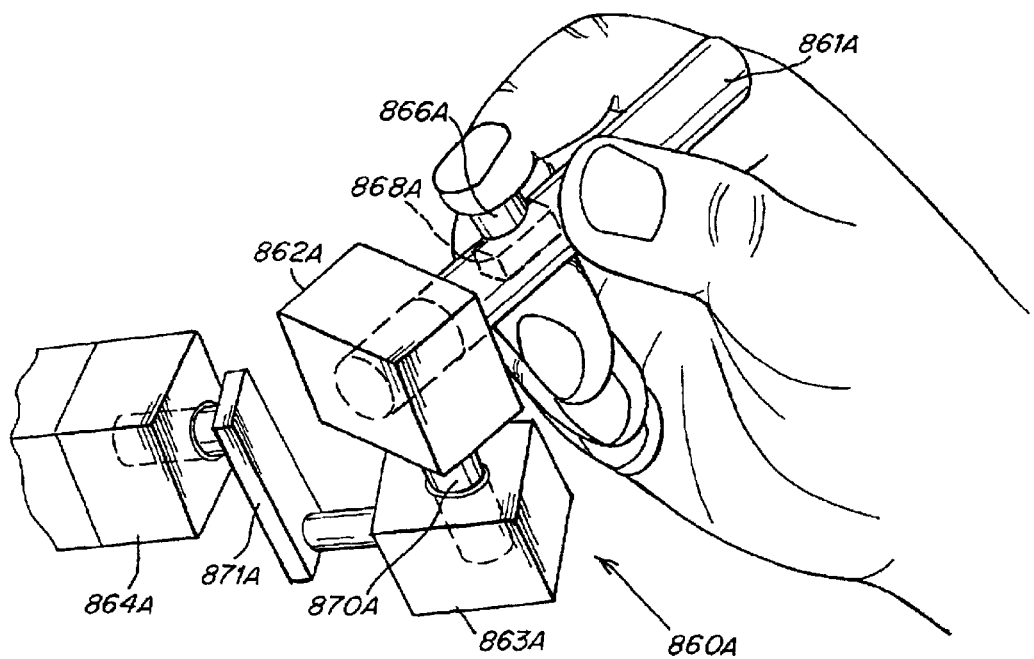
FIG. 18 is a schematic perspective view of an alternative hand piece for use at the master station.

Reference is now made to FIG. 18 which is a schematic perspective view of an alternate embodiment of an input device or hand assembly 860A. Rather than providing separate thumb and forefinger members, as illustrated previously, the surgeon's hand is holding a guide shaft 861A. On the shaft 861 there is provided a push-button 866A that activates an encoder 868A. The guide shaft 861A may be considered more similar to an actual surgical instrument intended to be handled directly by the surgeon in performing unassisted nonrobotic surgery. Thus, the hand piece 860A illustrated in FIG. 18 may be more advantageous to use for some types of operative procedures.

FIG. 18 illustrates, in addition to the encoder 868A, three other encoder blocks, 862A, 863A and 864A. These are schematically illustrated as being intercoupled by joints 870A and 871A. All four of these encoders would provide the same joint movements depicted previously in connection with joints J4–J7. For example, the button 866A may be activated by the surgeon to open and close the jaws.

C. The Slave Station S

C1—Slave Overview (FIGS. 8–8D)

Reference is now made to FIG. 8 which is a perspective view illustrating the present embodiment of the slave station S. A section of the surgical tabletop T is shown, from which extends the rigid angled post 19 that supports the surgical instrument 14 at mounting bracket 25. The drive unit 8 is also supported from the side of the tabletop by an L-shaped brace 210 that carries an attaching member 212. The brace is suitably secured to the table T and the drive unit 8 is secured to the attaching member 212 by means of a clamp 214. A lower vertical arm 19A of the rigid support rod 19 is secured to the attaching member 212 by another clamping mechanism 216, which mechanism 216 permits vertical adjustment of the rigid support 19 and attached instrument 14. Horizontal adjustment of the surgical instrument is possible by sliding the mounting bracket 25 along an upper horizontal arm 19B of the support rod 19. One embodiment of the drive unit 8 is described in further detail in FIG. 17. A preferred embodiment is illustrated in FIGS. 8F–8L.

The clamping bracket 216 has a knob 213 that can be loosened to reposition the support rod 19 and tightened to hold the support rod 19 in the desired position. The support rod 19, at its vertical arm 19A, essentially moves up and down through the clamp 216. Similarly, the mounting bracket 25 can move along the horizontal arm 19B of the support rod 19, and be secured at different positions therealong. The clamp 214, which supports the drive unit 8 on the operating table, also has a knob 215 which can be loosened to enable the drive unit to be moved to different positions along the attaching member 212.

FIG. 8 also shows the cable-in-conduit bundles 21 and 22. The cables in the bundle 21 primarily control the action of the adapter or guide member 15. The cables in bundle 22 primarily control the tool 18, all described in further detail below.

FIG. 8 also illustrates a support yoke 220 to which is secured the mounting bracket 25, a pivot piece 222, and support rails 224 for a carriage 226. Piece 222 pivots relative to the support yoke 220 about pivot pin 225.

FIG. 2B is a schematic representation of the joint movements associated with the slave station S. The first joint movement J1 represents a pivoting of the instrument 14 about pivot pin 225 at axis 225A. The second joint movement J2 is a transition of the carriage 226 on the rails 224, which essentially moves the carriage and instrument 14 supported therefrom, in the direction indicated by the arrow 227. This is a movement toward and away from the operative site OS. Both of these movements J1 and J2 are controlled by cabling in bundle 21 in order to place the distal end of the guide tube 17 at the operative site. The operative site is defined as the general area in proximity to where movement of the tool 18 occurs, usually in the viewing area of the endoscope and away from the incision.

FIG. 8 also shows a coupler 230 pivotally coupled from a base piece 234 by means of a pivot pin 232. The coupler 230 is for engaging with and supporting the proximal end of the instrument insert 16.

Figure 8B:
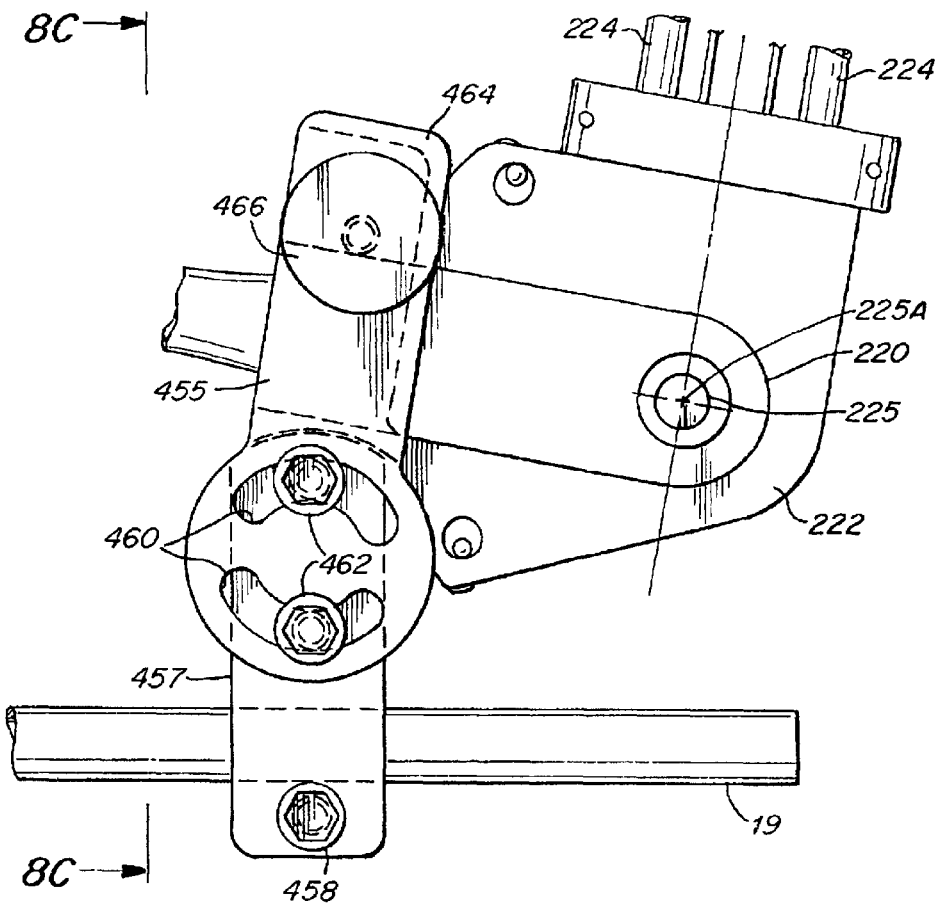
FIG. 8B is a top plan view of the clamp of FIG. 8A.
Figure 8C:
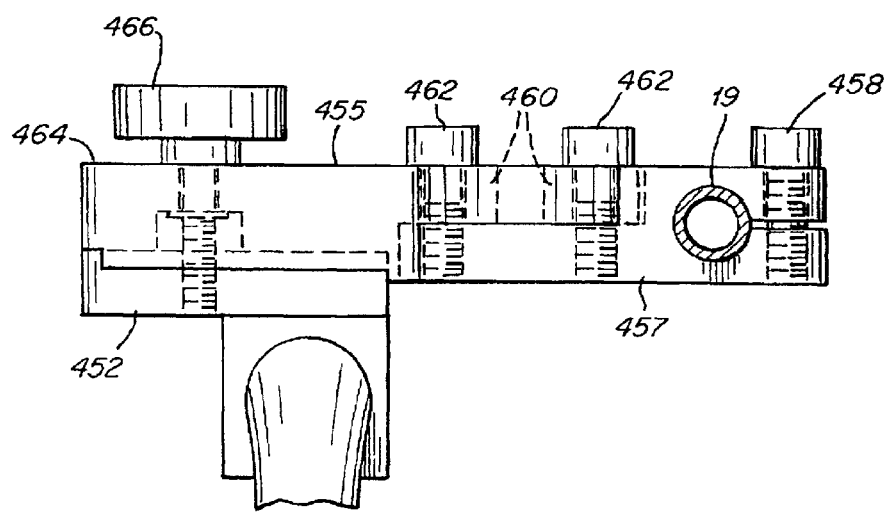
FIG. 8C is a side view of the clamp of FIGS. 8A and 8B as taken along line 8C—8C of FIG. 8B.

Reference is now made to FIGS. 8A, 8B and 8C which are perspective views of a preferred clamping arrangement which allows a limited amount of pivoting of the mounting bracket 25 (which supports instrument 14). The mounting bracket 25 includes a securing knob 450 that clamps the mounting bracket 25 to a base 452. The mounting bracket is basically two pieces 455 and 457. A bottom piece 457 is adapted to receive the upper arm of rigid supporting rod 19 (see FIG. 8B) and is secured thereto by a bolt 458. A top piece 455 is pivotably adjustable relative to the bottom piece 457 by means of slots 460 that engage with bolts 462. When bolts 462 are loosened, the top piece 455 may be rotated relative to the bottom piece 457 so that the instrument 14 may be held in different positions. The bolts 462 may then be tightened when the instrument 14 is in a desired angular position.

An adjustable bracket 25 and support post 19 may be provided at each side of the table for mounting a surgical instrument 14 on both the left and the right sides of the table. Depending upon the particular surgical procedure, it may be desirable to orient a pair of guide tubes on the left and right sides in different arrangements. In the arrangement of FIG. 1, the guide tubes 17, 17 are arranged so that the respective tools 18, 18 face each other. However, for other procedures it may be desirable to dispose the guides in different positions, allowed by the adjustability of brackets 25, 25 on their respective support posts 19, 19.

FIG. 8D shows a template 470 useful in a preferred procedure for positioning the guide tube. In this procedure, when the support post 19 is initially positioned, the mounting bracket 25 holds the template 470 (rather than the instrument 14). The template 470 has a right angle arm 472 with a locating ball 474 at the end thereof. The arm 472 extends a distance that is substantially the same as the lateral displacement of the guide tube 200 from pivot point 205 above the incision point 207 in FIG. 2C (see also the trocar 487 at the incision point 485 in FIG. 2B). The mounting bracket 25 is adjusted on the support post 19 so that the ball 474 coincides with the intended incision point of the patient. Thereafter, the template is removed and when the instrument 14 is then clamped to the mounting bracket, the guide tube 17 will be in the proper position vis-à-vis the patient's incision. Thus, the template 470 is used to essentially position the bracket 25 where it is desired to be located with the ball 474 coinciding with the incision point. Once the template is removed and the instrument is secured, the guide tube 17 will be in the proper position relative to the incision.

In connection with the operation of the present system, once the patient is on the table, the drive unit 8 is clamped to the table. It's position can be adjusted along the table by means of the attaching member 212. The lower arm 19A of the rigid support rod 19 is secured to the table by the bracket 216. The surgeon determines where the incision is to be made. The mounting bracket on the rigid rod 19 is adjusted and the template 470 is secured to the clamp 25. The ball 474 on the template is lined up with the incision so as to position the securing rod 19 and clamp 25 in the proper position. At that time the rigid rod 19 and the securing clamp 25 are fixed in position. Then the template is removed and the instrument 14 is positioned on the clamp 25. The incision has been made and the guide tube 17 is inserted through the incision into the patient and the instrument 14 is secured at the fixed position of mounting bracket 25.

With regard to the incision point, reference is made to FIG. 2B which shows the incision point along the dashed line 485. Also shown at that point is the cannula 487. In some surgical procedures it is common to use a cannula in combination with a trocar that may be used to pierce the skin at the incision. The guide tube 17 may then be inserted through the flexible cannula so that the tool is at the operative site. The cannula typically has a port at which a gas such as carbon dioxide enters for insufflating the patient, and a switch that can be actuated to desufflate. The cannula may typically include a valve mechanism for preventing the escape of the gas.

C2—Slave Cabling and Decoupling (FIGS. 8E–8L)

FIG. 8E illustrates a mechanical cabling sequence at the slave station from the drive unit 8, through adaptor 15 and insert 16, to the tool 18. Reference will again be made to FIG. 8E after a description of further details of the slave station.

Figure 8F:
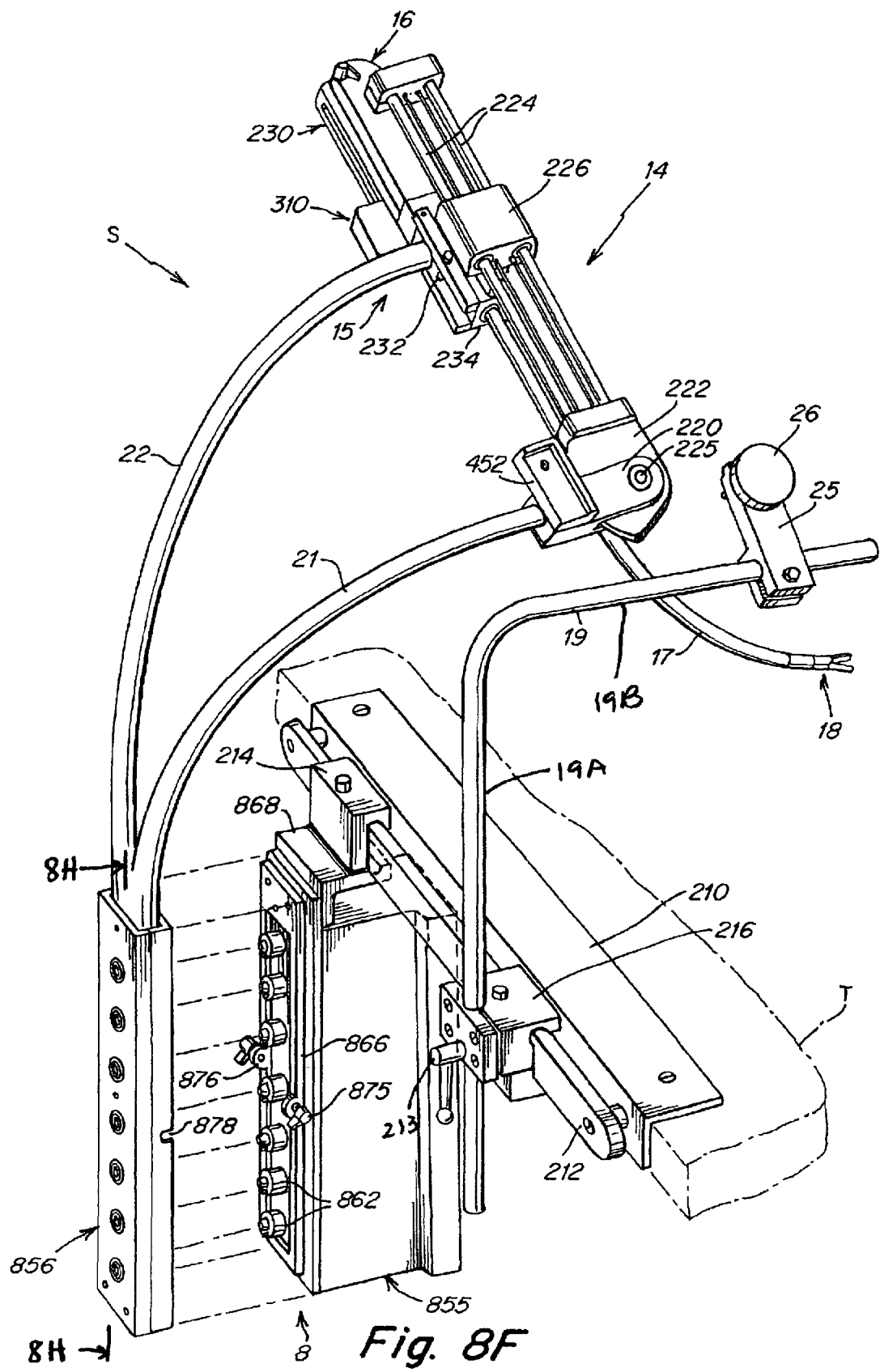
FIG. 8F is an exploded perspective view of another version of the cable drive mechanism and tool in accordance with the present invention.
Figure 86:
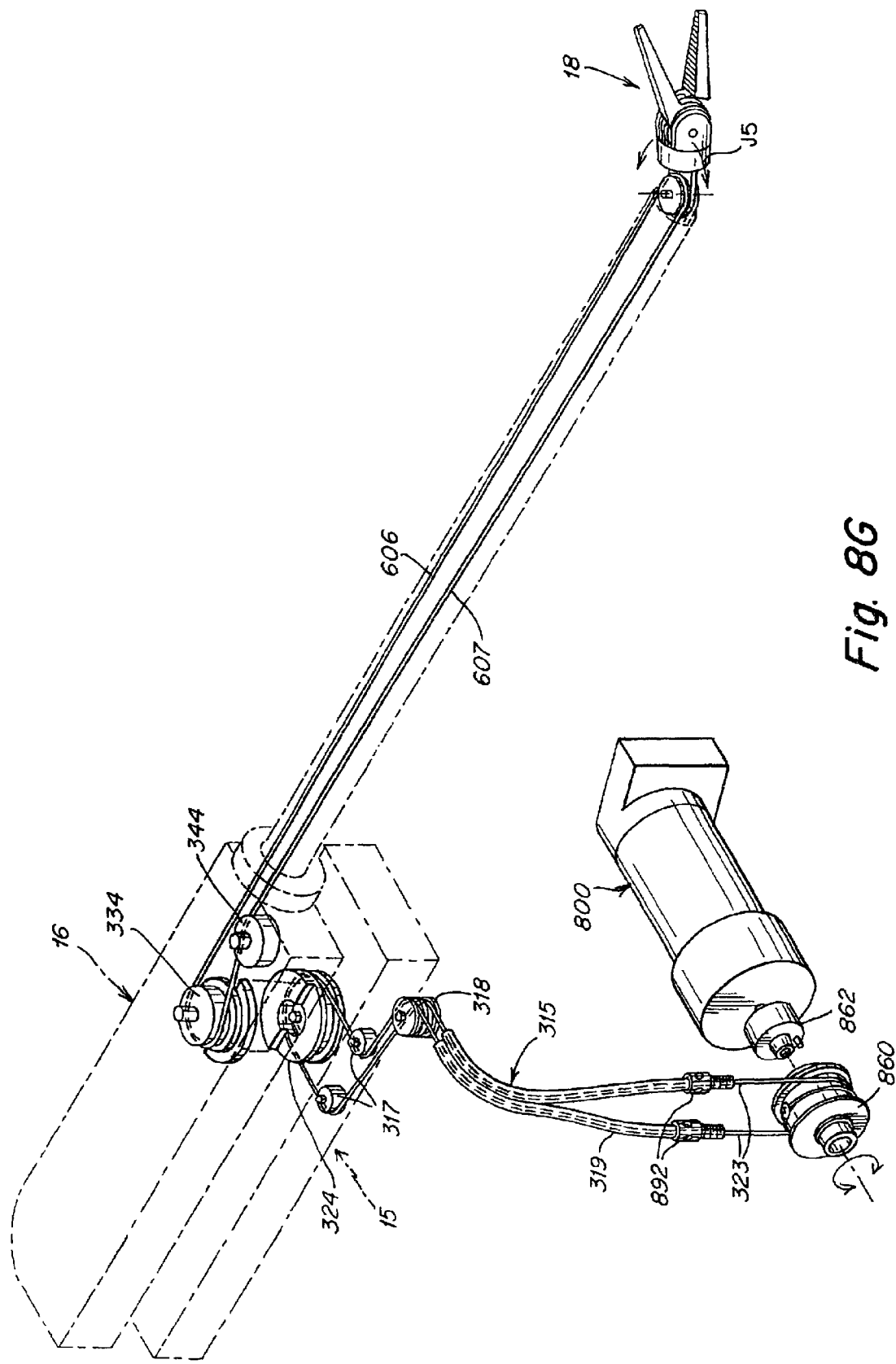

In the present embodiment the cable conduits 21 and 22 are detachable from the drive unit 8. This is illustrated in FIG. 8F wherein the drive unit includes separable housing sections 855 and 856. The instrument 14 along with the attached cable conduits 21 and 22 and housing section 856 are, as a unit, of relatively light weight and easily maneuverable (portable) to enable insertion of the instrument 14 into the patient prior to attachment to the bracket 25 on support post 19.

FIG. 8F is an exploded perspective view of the cable drive mechanism and instrument illustrating the de-coupling concepts of the present embodiment at the slave station S. A section of the surgical tabletop T which supports the rigid post 19 is shown. The drive unit 8 is supported from the side of the tabletop by an L-shaped brace 210 that carries an attaching member 212. The brace 210 is suitably secured to the table T. The drive unit 8 is secured to the attaching member 212 by means of a clamp 214. Similarly, the rigid support rod 19 is secured to the attaching member 212 by means of another clamping mechanism 216.

Also in FIG. 8F the instrument 14 is shown detached from (or not yet attached to) support post 19 at bracket 25. The instrument 14 along with cables 21 and 22 and lightweight housing section 856 provide a relatively small and lightweight decoupleable slave unit that is readily manually engageable (insertable) into the patient at the guide tube 17.

After insertion, the instrument assembly, with attached cables 21, 22 and housing 856, is attached to the support post 19 by means of the knob 26 engaging a threaded hole in base 452 of adapter 15. At the other end of the support post 19, bracket 216 has a knob 213 that is tightened when the support rod 19 is in the desired position. The support rod 19, at its vertical arm 19A, essentially moves up and down through the clamp 216. Similarly, the mounting bracket 25 can move along the horizontal arm 19B of the support rod to be secured at different positions therealong. A further clamp 214 enables the drive unit 8 to be moved to different positions along the attaching member 212.

FIG. 8F also shows the coupler 230 which is pivotally coupled from base piece 234 by means of the pivot pin 232.

The coupler 230 is for engaging with and supporting the proximal end of the instrument insert 16.

Reference is now made to FIG. 8G which illustrates the mechanical cabling sequence at the slave station. The cabling extends from a motor 800 (of the drive unit 8), via adaptor 15, and via the instrument insert 16 to the tool 18. The adapter 15 and insert 16 are intercoupled by their associated interlocking wheels 324 and 334. Cables 606 and 607, which in reality, are a single-looped cable, extend between the interlocking wheel 334 and the tool 18. These cables 606, 607 are used for pivoting the wrist-joint mechanism (at the tool 18), in the direction of arrow J5 illustrated in FIG. 8G.

FIG. 8G also illustrates an idler pulley 344 on the insert 16, as well as a pair of pulleys 317 associated with the wheel 324 on the adapter 15. Cabling 315 extends from interlocking wheel 324 about the pulleys 317, about an idler pulley 318 and through sheathing 319 to conduit turn buckles 892. The cables 323 extending from the turn buckles 892 are wrapped about a coupler spindle 860. Associated with the coupler spindle 860 is a coupler disk 862 secured to an output shaft of one of the motors 800 of drive unit 8.

Figure 8L:
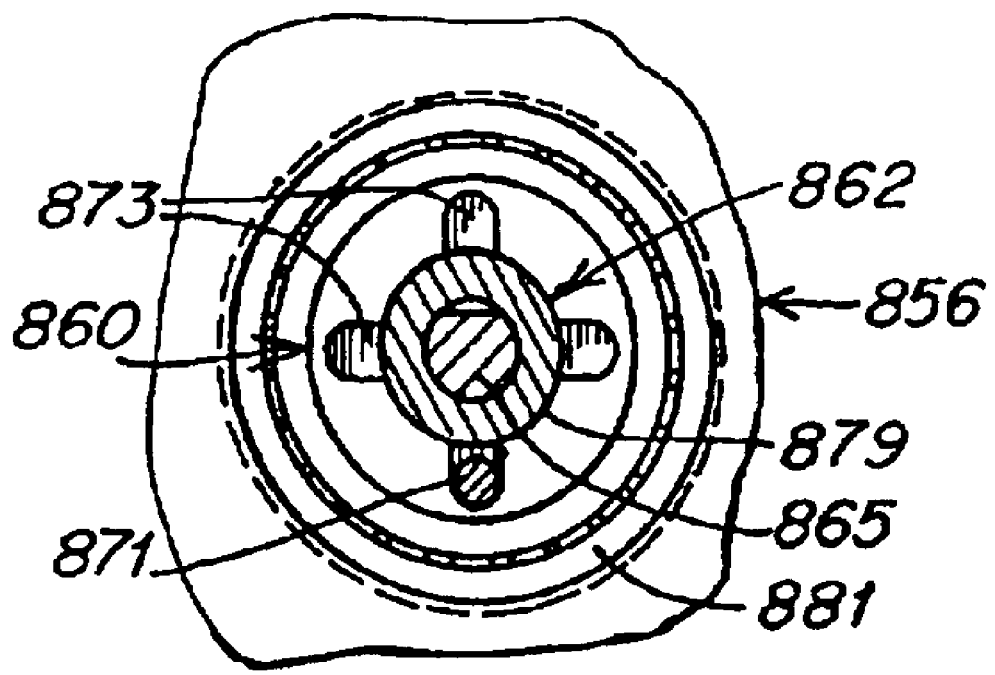
FIG. 8L is a cross-sectional rear view of the coupler spindle and disk as taken along line 8L—8L of FIG. 8K.

Reference is now made to further cross-sectional views illustrated in FIGS. 8H–8L. FIG. 8H is a partially broken away front-elevational view as taken along line 8H—8H of FIG. 8F. FIGS. 8I and 8J are cross-sectional views taken respectively along lines 8I—8I and 8J—8J of FIG. 8H. FIG. 8K is a cross-sectional side view taken along line 8K—8K of FIG. 8H. Lastly, FIG. 8L is a cross-sectional view as taken along line 8L—8L of FIG. 8K.

These cross-sectional views illustrate a series of seven motors 800, one for each of an associated mechanical cabling assembly. In, FIG. 8K, there is illustrated one of the motors 800 with its output shaft 865 extending therefrom. The motor 800 is secured to a housing wall 866 (also shown in FIG. 8F). FIG. 8K also shows the angle iron 868 that is used to support the housing section 855 from the bracket 214 (see FIG. 8F).

A coupler disk 862 is illustrated in FIGS. 8J and 8K, secured to the shaft 865 by a set screw 869. The coupler disk 862 also supports a registration pin 871 that is adapted to be received in slots 873 of the coupler spindle 860. FIGS. 8K and 8L illustrate the pin 871 in one of the slots 873. The registration pin 871 is biased outwardly from the coupler disk by means of a coil spring 874.

The first housing section 855 also carries oppositely disposed thumb screws 875 (see FIG. 8H). These may be threaded through flanges 876 as illustrated in FIG. 8J. When loosened, these set screws enable the second housing section 856 to engage with the first housing section 855. For this purpose, there is provided a slot 878 illustrated in FIG. 8F. Once the second housing section 856 is engaged with the first housing section 855, then the thumb screws 875 may be tightened to hold the two housing sections together, at the same time facilitating engagement between the coupler disks 862 and the coupler spindles 860.

The cross-sectional view of FIG. 8K shows that at the end of coupler disk 862 where it is adapted to engage with the coupler spindle 860, the coupler disk is tapered as illustrated at 879. This facilitates engagement between the coupler disk and the coupler spindle.

As illustrated in FIG. 8F, the two housing sections 855 and 856 are separable from each other so that the relatively compact slave unit can be engaged and disengaged from the motor array, particularly from the first housing section 855 that contains the motors 800. The first housing section 855, as described previously, contains the motors 800 and their corresponding coupler disks 862. In FIG. 8F, the second housing section 856 primarily accommodates and supports the coupler spindles 860 and the cabling extending from each of the spindles to the cable bundles 21 and 22 depicted in FIG. 8F.

FIGS. 8J and 8K illustrate one of the coupler spindles 860 supported within a pair of bearings 881. The cable associated with the coupler spindle is secured to the coupler spindle by means of a cable clamp screw 883. FIGS. 8J and 8K illustrate the cable extending about the coupler spindle, and secured by the cable clamp screw 883. The particular cable illustrated in FIGS. 8J about spindle 860 is identified as cable D.

In FIGS. 8H–8K, the cabling is identified by cables A–G. This represents seven separate cables that are illustrated, for example, in FIG. 8H as extending into the second housing section 856 with a flexible boot 885 (see the top of FIGS. 8H and 8K) extending thereabout.

At the top of the second housing section 856 there is provided a conduit stop or retainer 888 that is secured in place at the top of the housing section in an appropriate manner. The conduit retainer 888 has through slots 890, one for accommodating each of the cables A–G (see FIG. 8I). Refer in particular to FIGS. 8H and 8K illustrating the cables A–G extending through the retainer 888 in the slots thereof. Each of the cables may also be provided with a turnbuckle 892 that is useful in tensioning the cables. Each turnbuckle 892 screws into an accommodating threaded passage in the retainer 888, as illustrated in FIG. 8K.

In FIG. 8H the coupler spindles are all disposed in a linear array. To properly accommodate the cabling, the spindles are of varying diameter, commencing at the top of the second housing section 856 with the smallest diameter spindle and progressing in slightly larger diameter spindles down to the bottom of the second housing section 856 where there is disposed the largest diameter coupler spindle.

The detachability of the two housing sections 855 and 856 enables the cleaning of certain components which are disposed above the plane of the operating table, here referred to as the sterile field. More specifically, the detachable housing 856 with attached cables 21 and 22 and instrument 14, needs to be sterilized after use, except for the instrument insert 16 which is an integral disposal unit. The sterilization of the designated components may include a mechanical cleaning with brushes or the like in a sink, followed by placement in a tray and autoclave in which the components are subjected to superheated steam to sterilize the same. In this manner, the adapter 15 is reusable. Also, the engagement between the adapter 15 and insert 16 is such that the disposable insert element may have holes, which are relatively hard to clean, whereas the recleanable adapter element has a minimum number of corresponding projections, which are relatively easier to clean than the holes. By disposable, it is meant that the unit, here the insert 16, is intended for a single use as sold in the marketplace. The disposable insert interfaces with an adapter 15 which is intended to be recleaned (sterilized) between repeated uses. Preferably, the disposable unit, here the insert 16, can be made of relatively lower cost polymers and materials which, for example, can be molded by low-cost injection molding. In addition, the disposable instrument insert 16 is designed to require a relatively minimal effort by the operator or other assistant who is required to attach the insert to the adapter 15. More specifically, the operator is not required to rethread any of the multiple mechanical cabling assemblies.

C3—Slave Instrument Assembly (FIGS. 9–16)

Further details of the detachable and portable slave unit are shown in FIGS. 9–16. For example, FIG. 11 shows the carriage 226 which extends from the mounting bracket 25 on support post 19. Below carriage 226, a base piece 234 is supported from the carriage 226 by a rectangular post 228. The post 228 supports the entire instrument assembly, including the adaptor 15 and the instrument insert 16 once engaged.

As indicated previously, a support yoke 220 is supported in a fixed position from the mounting bracket 25 via base 452. Cabling 21 extends into the support yoke 220. The support yoke 220 may be considered as having an upper leg 236 and a lower leg 238 (see FIG. 12). In the opening 239 between these legs 236, 238 there is arranged the pivot piece 222 with its attached base 240. Below the base 240 and supported by the pivot pin 225 is a circular disc 242 that is stationary relative to the yoke legs 236, 238. A bearing 235 in leg 236, a bearing 237 in leg 238, and a bearing 233 in disc 242, allow rotation of these members relative to the pivot pin 225.

Figure 13:
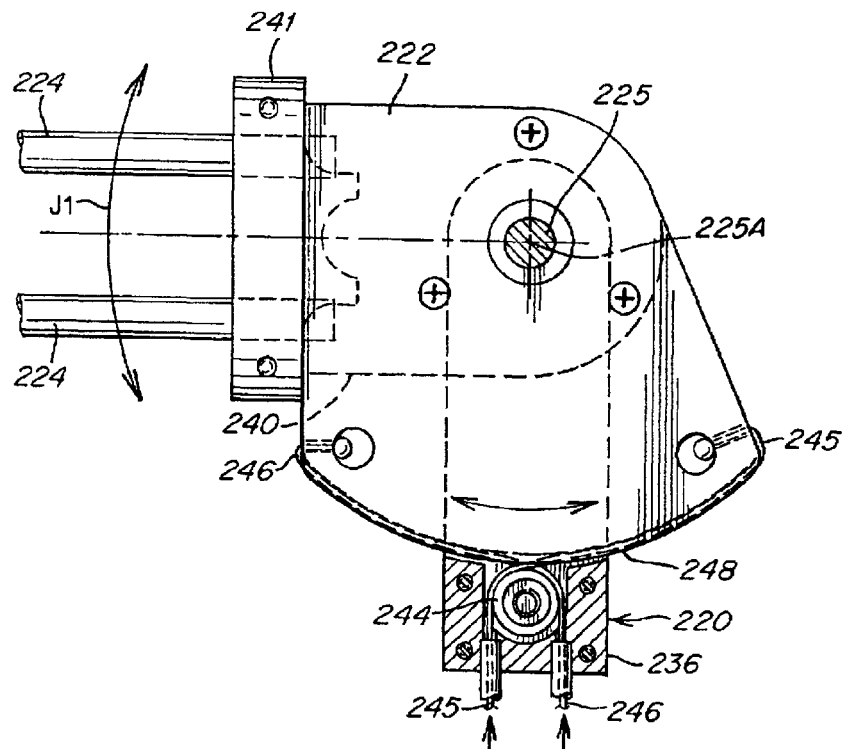
FIG. 13 is a cross-sectional view as taken along line 13—13 of FIG. 12.

Disposed within a recess in the support yoke 220, as illustrated in FIG. 13, is a capstan 244 about which cables 245 and 246 extend and are coupled to opposite sides of the arcuate segment 248 of pivot piece 222. The ends of cables 245 and 246 are secured in holes at opposite sides of arcuate segment 248. The cables 245 and 246 operate in conjunction with each other. At their other ends, these cables connect to a motor. Depending upon the direction of rotation of the motor, either cable 245 or cable 246 will be pulled, causing the pivot price 232 to rotate in a direction indicated by J1.

Figure 14:
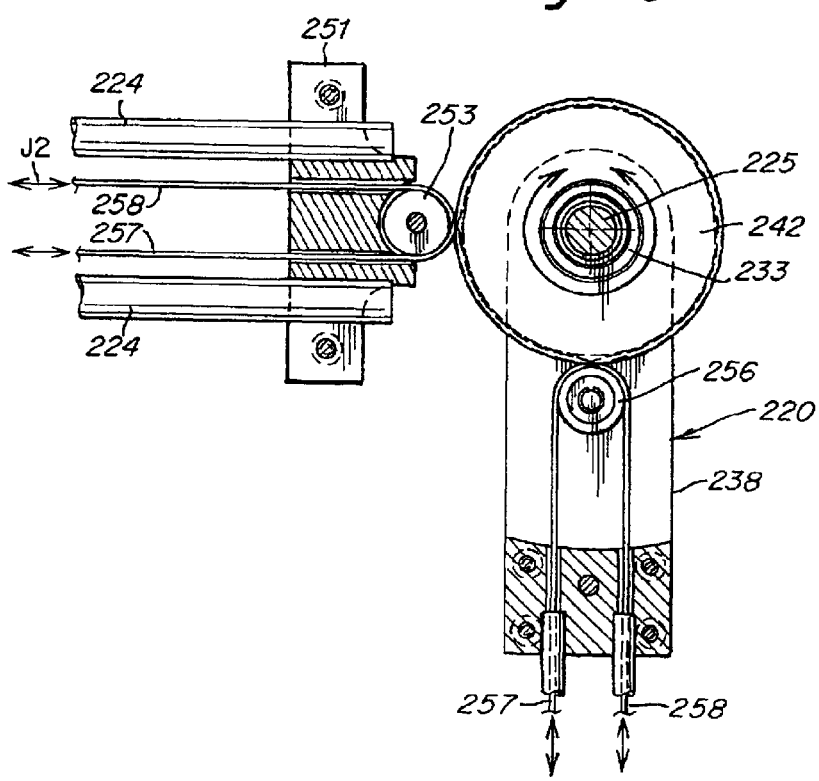
FIG. 14 is a cross-sectional view as taken along line 14—14 of FIG. 12.

The base 240 of pivot piece 222 also has at one end thereof an end piece 241 into which are partially supported the ends of rails 224 (see FIG. 13). The other ends of the rails are supported by an end piece 251, which also has cabling 257, 258 for the carriage 226 extending therethrough, such as illustrated in FIG. 14. A capstan 253 is supported from a lower surface of the base 240. Another capstan 256 is supported within the support yoke 220. The cables 257 and 258 extend about the capstan 256, about disc 242 (which may be grooved to receive the cables), to the carriage 226, and from there about another capstan 260 disposed within end member 262 (see FIG. 11). End member 262 supports the other ends of the rails 224, upon which the carriage 226 transitions. The ends of the cables 257 and 258 are secured appropriately within the carriage. FIG. 11 illustrates by the arrow 227 the forward and backward motion of the carriage 226, and thus of the attached actuator 15 toward and away from the operative site.

Figure 15:
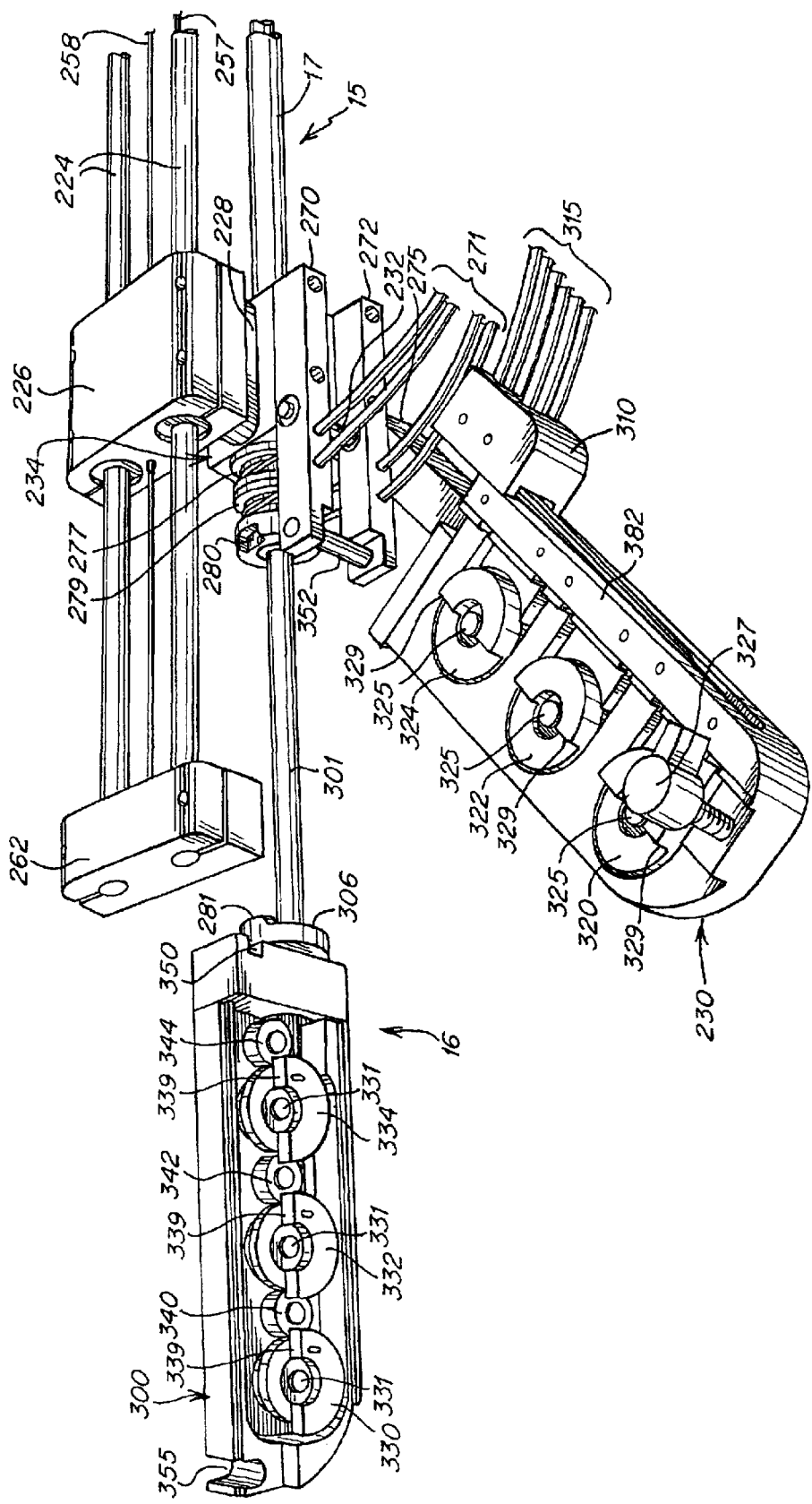
FIG. 15 is a perspective view at the slave station showing the instrument insert being removed from the adapter.

Now, reference is made to FIG. 15 illustrating a portion of the slave unit with the instrument insert 16 partially removed and rotated from the base piece 234. FIG. 15 shows a portion of the carriage mechanism, including the carriage 226 supported on rails 224. As indicated previously, below the carriage 226 there is a support post 228 that supports the base piece 234. It is at the base piece 234, that cabling 22 from the drive unit 8 is received.

Also extending from the base piece 234 is the guide tube 17 of adapter 15. The guide tube 17 accommodates, through its center axial passage, the instrument insert 16. Also, supported from the base piece 234, at pivot pin 232, is the adaptor coupler 230. The adaptor coupler 230 pivots out of the way so that the instrument insert 16 can be inserted into the adaptor 15. FIG. 15 shows the instrument insert 16 partially withdrawn from the adaptor 15. The pivot pin 232 may be longer than the distance between the two parallel bars 270 and 272 carried by base piece 234, so that the pin not only allows rotation, but can also slide relative to bars 270 and 272. This permits the coupler 230 to not only pivot, but also to move laterally to enable better access of the instrument insert 16 into the base piece 234. The instrument insert 16 has a base (coupler) 300 that in essence is a companion coupler to the adapter coupler 230.

Figure 15A:
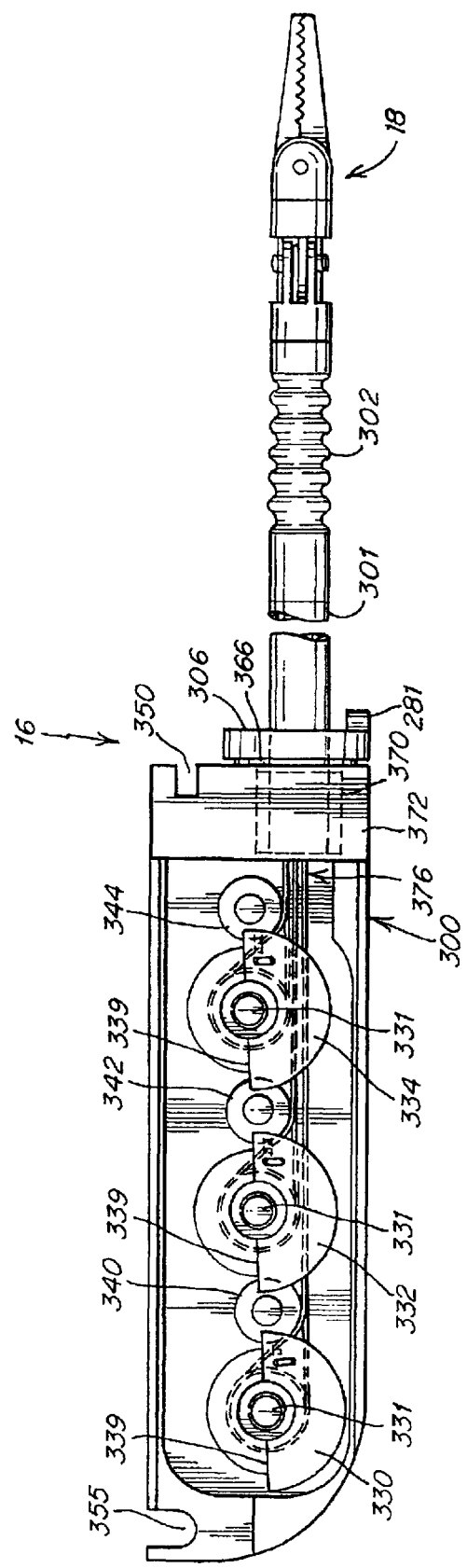
FIG. 15A is a top plan view of the instrument insert itself.

With further reference to FIG. 15, the instrument insert 16 is comprised of a coupler 300 at the proximal end, and at the distal end an elongated shaft or stem, which in this embodiment has a more rigid proximal stem section 301 and a flexible distal stem section 302 (see FIG. 15A). The distal stem section 302 carries the tool 18 at its distal end. The instrument coupler 300 includes one or more wheels 339 which laterally engage complimentary wheels 329 of the coupler 230 on adaptor 15. The instrument coupler 300 also includes an axial wheel 306 at its distal end through which the stem 301 extends, and which also engages a wheel on the adaptor, as to be described below in further detail. The axial engagement wheel 306 is fixed to the more rigid stem section 301, and is used to rotate the tool 18 axially at the distal end of the flexible stem section 302 (as shown by arrow J4 in FIG. 2B).

The base piece 234 has secured thereto two parallel spaced-apart bars 270 and 272. It is between these bars 270 and 272 that is disposed the pivot pin 232. The pivot pin 232 may be supported at either end in bearings in the bars 270 and 272, and as previously mentioned, has limited sliding capability so as to move the adapter coupler 230 away from base piece 234 to enable insertion of the instrument insert 16. A leg 275 is secured to the pivot pin 232. The leg 275 extends from the coupler 230 and provides for pivoting of coupler 230 with respect to base piece 234. Thus, the combination of pivot pin 232 and the leg 275 permits a free rotation of the coupler 230 from a position where it is clear to insert the instrument insert 16 to a position where the coupler 230 intercouples with the base 300 of the instrument insert 16. As depicted in FIG. 15, the bars 270 and 272 also accommodate therethrough cabling from cable bundles 271.

The base piece 234 also rotatably supports the rigid tube 17 (illustrated by arrow J3 in FIG. 2B). As indicated previously, it is the connection to the carriage 226 via post 228 that enables the actuator 15 to move toward and away from the operative site. The rotation of the tube 17 is carried out by rotation of pulley 277 (see FIG. 15). A pair of cables from the bundle 271 extend about the pulley 277 and can rotate the pulley in either direction depending upon which cable is activated. To carry out this action, the tube 17 is actually supported on bearings within the base piece 234. Also, the proximal end of the tube 17 is fixed to the pulley 277 so that the guide tube 17 rotates with the pulley 277.

Also supported from the very proximal end of the tube 17, is a second pulley 279 that is supported for rotation about the actuator tube 17. For this purpose a bearing is disposed between the pulley 279 and the actuator tube. The pulley 279 is operated from another pair of cables in the bundle 271 that operate in the same manner. The cabling is such that two cables couple to the pulley 279 for operation of the pulley in opposite directions. Also, as depicted in FIG. 15, the pulley 279 has a detent at 280 that is adapted to mate with a tab 281 on the axial wheel 306 of instrument coupler 300. Thus, as the pulley 279 is rotated, this causes a rotation of the axial wheel 306 and a corresponding rotation of flexible and rigid sections 301, 302 of the instrument insert 16, including the tool 18.

Again referring to FIG. 15, a block 310 is secured to one side of the coupler 230. The block 310 is next to the leg 275 and contains a series of small, preferably plastic, pulleys that accommodate cabling 315. These cables extend to other pulleys 317 disposed along the length of the coupler 230. Refer also to the cabling diagram of FIG. 8E.

In this embodiment, the coupler 230 includes wheels 320, 322 and 324. Each of these wheels is provided with a center pivot 325 to enable rotation of the wheels in the coupler 230. The knob 327 is used to secure together the adapter coupler 230 and the base coupler 300 of the instrument insert 16.

For the three wheels, 320, 322 and 324, there are six corresponding pulleys 317, two pulleys being associated with each wheel (see FIGS. 8E and 11B). Similarly, there are six pulleys in the block 310. Thus, for cabling bundle 315 there are six separate cable conduits for the six separate cables that couple to the wheels 320, 322 and 324. Two cables connect to each wheel for controlling respective opposite directions of rotation thereof.

Each of the wheels 320, 322 and 324 have a half-moon portion with a flat side 329. Similarly, the instrument base 300 has companion wheels 330, 332 and 334 with complimentary half-moon construction for engagement with the wheels 320, 322 and 324. The wheel 320 controls one of the jaws of the tool 18 (motion J6 in FIG. 2B). The wheel 324 controls the other jaw of the tool 18 (motion J7 in FIG. 2B). The middle wheel 322 controls the wrist pivoting of the tool 18 (motion J5 in FIG. 2B). Also refer to FIG. 8E showing cabling for controlling tool movement.

The coupler 300 of insert 16 has three wheels 330, 332 and 334, each with a pivot pin 331, and which mate with the corresponding wheels 320, 322 and 324, respectively of the adaptor coupler. In FIG. 15 the instrument base piece 300 is shown rotated from its normal position for proper viewing of the wheels. Normally, it is rotated through 180° so that the half-moon wheels 330, 332 and 334 engage with the corresponding coupler wheels 320, 322 and 324. Also illustrated in FIG. 15 are capstans or idler pulleys 340, 342 and 344 associated, respectively, with wheels 330, 332 and 334.

As shown in FIG. 15A, each wheel of the instrument coupler 300 has two cables 376 that are affixed to the wheel (e.g., wheel 334 in FIG. 8E) and wrapped about opposite sides at its base. The lower cable rides over one of the idler pulleys or capstans (e.g., capstan 34 in FIG. 8E), which routes the cables toward the center of the instrument stem 301. It is desirable to maintain the cables near the center of the instrument stem. The closer the cables are to the central axis of the stem, the less disturbance motion on the cables when the insert stem is rotated. The cables may then be routed through fixed-length plastic tubes that are affixed to the proximal end of the stem section 301 and the distal end of the stem section 302. The tubes maintain constant length pathways for the cables as they move within the instrument stem.

The instrument coupler 300 is also provided with a registration slot 350 at its distal end. The slot 350 engages with a registration pin 352 supported between the bars 270 and 272 of base piece 234. The coupler 300 is also provided with a clamping slot 355 on its proximal end for accommodating the threaded portion of the clamping knob 327 (on adapter coupler 230). The knob 327 affirmatively engages and interconnects the couplers 230 and 300.

In operation, once the surgeon has selected a particular instrument insert 16, it is inserted into the adapter 15. The proximal stem 301, having the distal stem 302 and the tool 18 at the distal end, extend through the adapter guide tube 17. FIG. 8 shows the tool 18 extending out of the guide tube 17 when the surgical instrument 16 is fully inserted into the adaptor 15. When it is fully inserted, the tab 281 on the axial wheel 306 engages with the mating detent 280 in pulley 279. Also, the registration slot 350 engages with the registration pin 352. Then the coupler 230 is pivoted over the base 300 of the instrument insert 16. As this pivoting occurs, the respective wheels of the coupler 230 and the coupler 300 interengage so that drive can occur from the coupler 230 to the insert 16. The knob 327 is secured down so that the two couplers 230 and 300 remain in fixed relative positions.

Reference is also now made to detailed cross-sectional views of FIGS. 11A, 11B and 11C. FIG. 11A is a cross sectional view taken along line 11A—11A of FIG. 11. FIG. 11B is a cross-sectional view taken along line 11B—11B of FIG. 11A. FIG. 11C is a further cross-sectional view taken through FIG. 11A along line 11C—11C.

The base piece 234 of adapter 15 rotatably supports the guide tube 17, allowing rotation J3 shown in FIG. 2B. As noted in FIG. 11A, there are a pair of bearings 360 disposed at each end within the axial passage 362 in the base piece 234. The rotation of the guide tube 17 is carried out by rotation of the first pulley 277. In FIG. 11A there is a set screw 364 that secures the pulley 277 to the guide tube 17. Nylon spacers 366 separate various components, such as the base piece 234 and the pulley 277, the two pulleys 277 and 279, and base 300 and wheel 306.

A nylon bearing 368 is also provided between the second pulley 279 and the guide tube 17. FIG. 11A also shows the proximal stem section 301 of the insert 16 inside of the guide tube 17. A nylon bearing 370 is supported within the front block 372 of the insert 16.

In FIG. 11A, the second pulley 279 is supported from the proximal end of the tube 17. The bearing 368 is disposed between the pulley 279 and the tube 17. The pulley 279 has a detent 280 that is adapted to mate with a tab 281 on the axial wheel 306. Thus, when the pulley 279 is rotated by cabling 271 (see FIG. 11C), this causes a rotation of the axial wheel 306, and a corresponding rotation (motion J4 in FIG. 2B) of the sections 301, 302 of the instrument insert 16, including the tool 18. The very proximal end of the section 301 is illustrated in FIG. 11A as being rotatable relative to the bearing 370.

FIG. 11A also shows the intercoupling of the instrument and adapter couplers 230 and 300. Here wheel 324 is shown interlocked with wheel 334. FIGS. 11A and 11C also show cabling at 376. This cabling includes six separate cables that extend through the length of the stem 301, 302 of the instrument. The cabling is illustrated connecting about an idler pulley 344. The cabling associated with wheel 334 is secured by the cable clamping screw 378. For further details of the cabling, refer to FIG. 8E.

FIG. 11B is a cross-sectional view taken along 11B—11B of FIG. 11A which again shows the cooperating wheels 324 and 334. Also illustrated is a cable clamping set screw 380 that is used to secure the cabling 376 to wheel 324. A cable guide rail 382 is attached and forms part of the base of the adapter coupler 230. The cable guide rail 382 contains six idler pulleys 317, one of which is illustrated in FIG. 11B. It is noted that cabling 376 extends about this pulley to the cable idler block 310 where conduits 315 are coupled. The cable guide idler block 310 includes a series of six idler pulleys shown in dotted outline in FIG. 11B at 386.

FIG. 11C is a cross-sectional view taken along line 11C—11C of FIG. 11A, which shows further details at the pulley 279. Also illustrated is post 228 supporting the base piece 234 of the instrument insert, and cabling 376 extending through the instrument.

Figure 16A:
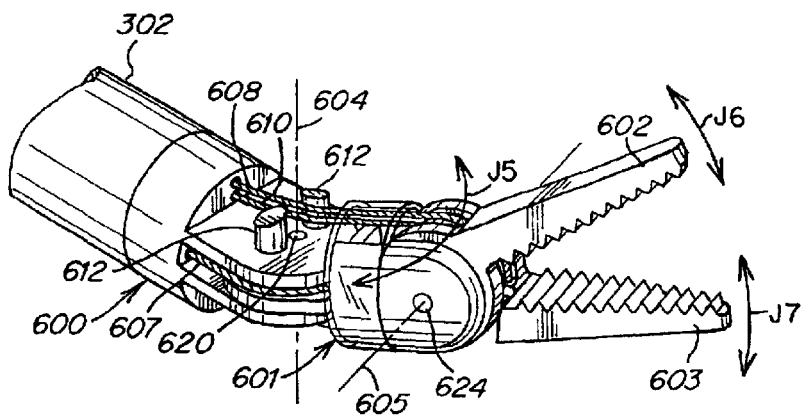
FIG. 16A is a perspective view at the tool as viewed along line 16A—16A of FIG. 11.
Figure 16B:
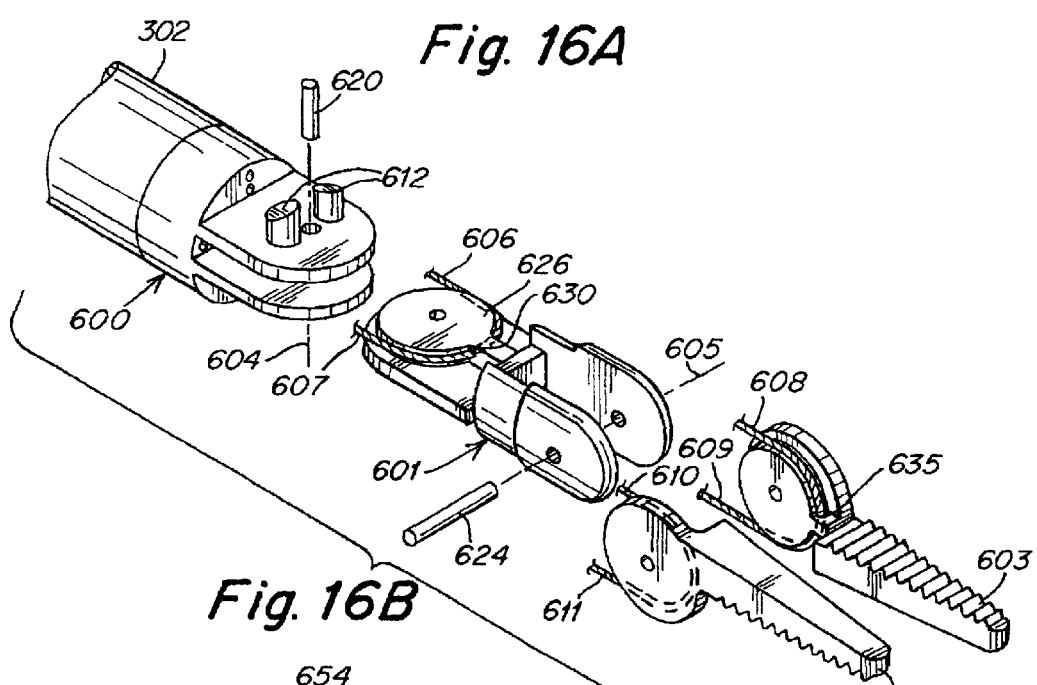
FIG. 16B is an exploded perspective view of the tool of FIG. 16A.

FIGS. 16A and 16B illustrate the construction of one form of a tool. FIG. 16A is a perspective view and FIG. 16B is an exploded view. The tool 18 is comprised of four members including a base 600, link 601, upper grip or jaw 602 and lower grip or jaw 603. The base 600 is affixed to the flexible stem section 302 (see FIG. 15A). The flexible stem may be constructed of a ribbed plastic. This flexible section is used so that the instrument will readily bend through the curved part of the guide tube 17.

The link 601 is rotatably connected to the base 600 about axis 604. FIG. 16B illustrates a pivot pin 620 at axis 604. The upper and lower jaws 602 and 603 are rotatably connected by pivot pin 624 to the link 601 about axis 605, where axis 605 is essentially perpendicular to axis 604.

Six cables 606–611 actuate the four members 600–603 of the tool. Cable 606 travels through the insert stem (section 302) and through a hole in the base 600, wraps around curved surface 626 on link 601, and then attaches on link 601 at 630. Tension on cable 606 rotates the link 601, and attached upper and lower grips 602 and 603, about axis 604 (motion J5 in FIG. 2B). Cable 607 provides the opposing action to cable 606, and goes through the same routing pathway, but on the opposite sides of the insert. Cable 607 may also attach to link 601 generally at 630.

Cables 608 and 610 also travel through the stem 301, 302 and though holes in the base 600. The cables 608 and 610 then pass between two fixed posts 612. These posts constrain the cables to pass substantially through the axis 604, which defines rotation of the link 601. This construction essentially allows free rotation of the link 601 with minimal length changes in cables 608–611. In other words, the cables 608–611, which actuate the jaws 602 and 603, are essentially decoupled from the motion of link 601. Cables 608 and 610 pass over rounded sections and terminate on jaws 602 and 603, respectively. Tension on cables 608 and 610 rotate jaws 602 and 603 counter-clockwise about axis 605. Finally, as shown in FIG. 16B, the cables 609 and 611 pass through the same routing pathway as cables 608 and 610, but on the opposite side of the instrument. These cables 609 and 611 provide the clockwise motion to jaws 602 and 603, respectively. At the jaws 602 and 603, as depicted in FIG. 16B, the ends of cables 608–611 may be secured at 635, for example by the use of an adhesive such as epoxy glue, or the cables could be crimped to the jaws.

To review the allowed movements of the various components of the slave unit, the instrument insert 16 slides through the guide tube 17 of adaptor 15, and laterally engages the adaptor coupler 230. The adaptor coupler 230 is pivotally mounted to the base piece 234. The base piece 234 rotationally mounts the guide tube 17 (motion J3). The base piece 234 is affixed to the linear slider or carriage assembly (motion J2). The carriage assembly in turn is pivotally mounted at the pivot 225 (motion J1).

Figure 16C:
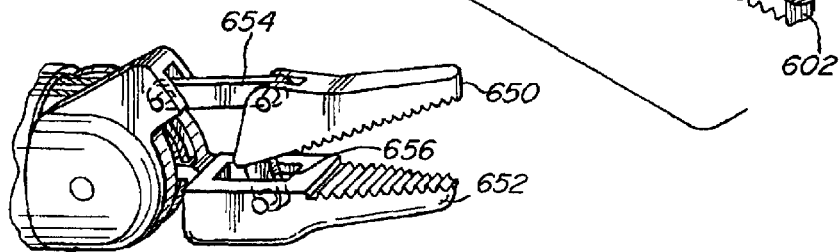
FIG. 16C is a fragmentary perspective view of an alternative tool referred to as a needle driver.
Figure 16D:
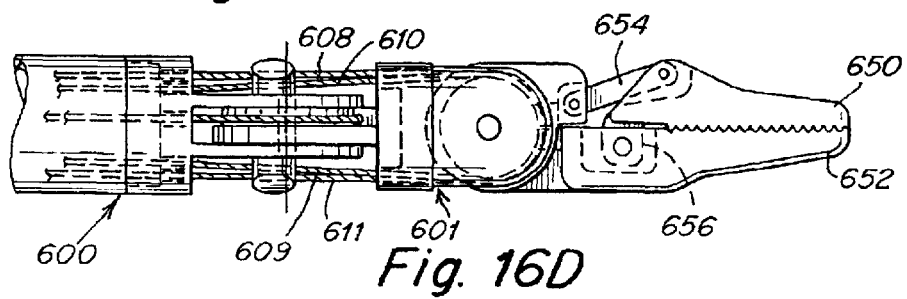
FIG. 16D is a side elevation view of the needle driver of FIG. 16C.

Reference is now made to FIGS. 16C and 16D. FIG. 16C is a fragmentary perspective view of an alternate set of jaws, referred to as needle drivers. FIG. 16D is a side elevation view of the needle drivers. This embodiment employs an over-center camming arrangement so that the jaw is not only closed, but also at a forced closure.

In FIGS. 16C and 16D, similar reference characters are employed with respect to the embodiment of FIGS. 16A and 16B. Thus, there is provided a base 600, a link 601, an upper jaw 650 and a lower jaw 652. The base 600 is affixed to the flexible stem section 302. Cabling 608–611 operate the end jaws. Linkages 654 and 656 provide the over-center camming operation.

The two embodiments of FIGS. 16A–16D employ a fixed wrist pivot. An alternate construction is illustrated in FIGS. 16E–16H in which there is provided, in place of a wrist pivot, a flexible or bending section. In FIGS. 16E–16H, similar reference characters are used for many of the parts, as they correspond to elements found in FIGS. 16A–16D.

In the embodiment of FIGS. 16E–16H, the tool 18 is comprised of an upper grip or jaw 602 and a lower grip or jaw 603, supported from a link 601. Each of the jaws 602, 603, as well as the link 601, may be constructed of metal, or alternatively, the link 601 may be constructed of a hard plastic. The link 601 is engaged with the distal end of the flexible stem section 302. In this regard reference may also be made to FIG. 15A that shows the ribbed, plastic construction of the flexible stem section 302. FIG. 16E shows only the very distal end of the stem section 302, terminating in a bending or flexing section 660. The flexible stem section 302 is constructed so as to be flexible and thus has a substantial length of a ribbed surface as illustrated in FIG. 15A. Also, at the flexible section 660, flexibility and bending is enhanced by means of diametrically-disposed slots 662 that define therebetween ribs 664. The flexible section 660 also has a longitudinally extending wall 665, through which cabling extends, particularly for operation of the tool jaws. The very distal end of the bending section 660 terminates with an opening 666 for receiving the end 668 of the link 601. The cabling 608–611 is preferably at the center of the flex section at wall 665 so as to effectively decouple flex or bending motions from tool motions.

Regarding the operation of the tool, reference is made to the cables 608,609,610, and 611. All of these extend through the flexible stem section and also through the wall 665 such as illustrated in FIG. 16G. The cables extend to the respective jaws 602,603 for controlling operation thereof in a manner similar to that described previously in connection with FIGS. 16A–16D. FIGS. 16E–16H also illustrate the cables 606 and 607 which couple through the bending section 660 and terminate at ball ends 606A and 607A, respectively. Again, refer to FIG. 16G that shows these cables. FIGS. 16F and 16H also show the cables 606,607 with the ball ends 606A, 607A, respectively. These ball ends are adapted to urge against the very end of the bendable section in opening 666. When these cables are pulled individually, they can cause a bending of the wrist at the bending or flexing section 660. FIG. 16H illustrates the cable 607 having been pulled in the direction of arrow 670 so as to flex the section 660 in the manner illustrated in FIG. 16H. Pulling on the other cable 606 causes a bending in the opposite direction.

By virtue of the slots 662 forming the ribs 664, there is provided a structure that bends quite readily, essentially bending the wall 665 by compressing at the slots such as in the manner illustrated in FIG. 16H. This construction eliminates the need for a wrist pin or hinge.

The embodiment illustrated in FIG. 16F has a separate link 601. However, in an alternate embodiment, this link 601 may be fabricated integrally with, and as part of, the bending section 660. For this purpose the link 601 would then be constructed of a relatively hard plastic rather than the metal link as illustrated in FIG. 16F and would be integral with section 660.

In another embodiment, the bending or flexing section 660 can be constructed so as to have orthogonal bending by using four cables separated at 90° intervals and by providing a center support with ribs and slots about the entire periphery. This embodiment is shown in FIGS. 16I–16K. The bending section 613 is at the end of flexible stem section 302. The cables 608, 609, 610 and 611 are for actuation of the jaws 602 and 603 in the same manner as for earlier embodiments. The link 601 couples the bending section 613 to the jaws 602 and 603.

The bending section has a center support wall 614 supporting ribs 618 separated by slots 619. This version enables bending in orthogonal directions by means of four cables 606,607,616 and 617, instead of the single degree-offreedom of FIG. 16E. The operation of cables 606 and 607 provides flexing in one degree-of-freedom, while an added degree-of-freedom is provided by operation of cables 616 and 617.

Mention has also been made of various forms of tools that can be used. The tool may comprise a variety of articulated tools such as: jaws, scissors, graspers, needle holders, micro dissectors, staple appliers, tackers, suction irrigation tools and clip appliers. In addition, the tool may comprise a non-articulated instrument such as: a cutting blade, probe, irrigator, catheter or suction orifice.

Figure 17:
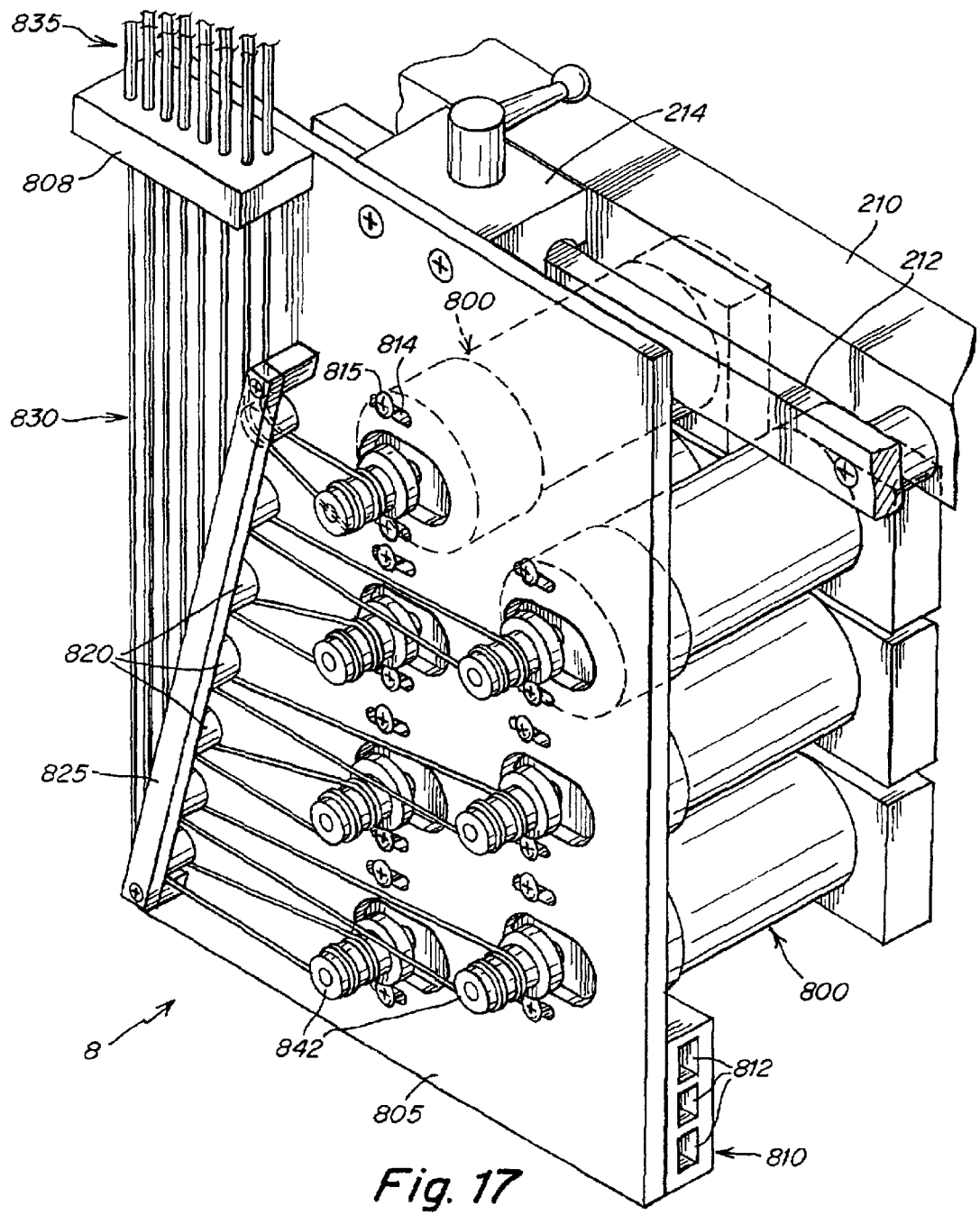
FIG. 17 is a perspective view of the drive unit at the slave station.
Figure 17A:
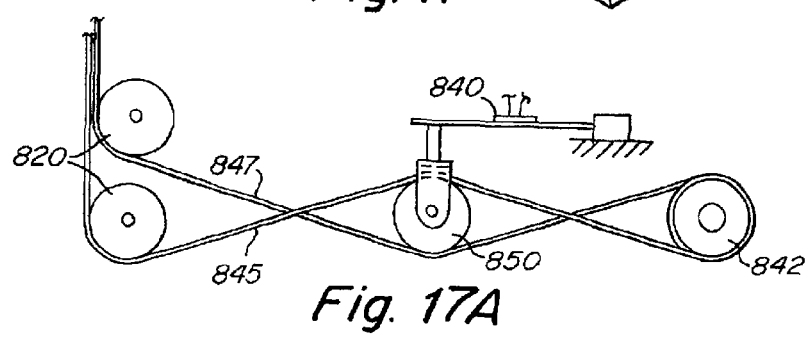
FIG. 17A is a schematic front view of the drive unit at the slave station.

C4—Slave Drive Unit (FIGS. 17–17A)

Reference is now made to the perspective view of the drive unit 8, previously illustrated in FIG. 8. FIG. 17 illustrates the drive unit 8 with the cover removed. The drive unit is adjustably positionable along rail 212 by an angle brace 210 that is attached to the operating table. Within the drive unit 8 are seven separate motors 800, corresponding to the seven separate controls at the slave station, and more particularly, to motions J1–J7 previously described in reference to FIG. 2B.

The drive unit includes a support plate 805 to which there is secured a holder 808 for receiving and clamping the cabling conduits 835. The motors 800 are each supported from the support plate 805. FIG. 17 also illustrates the electrical interface at 810, with one or more electrical connectors 812.

Regarding support for the motors 800 there is provided, associated with each motor, a pair of opposed adjusting slots 814 and adjusting screws 815. This permits a certain degree of positional adjustment of the motors, relative to their associated idler pulleys 820. The seven idler pulleys are supported for rotation by means of a support bar 825. FIG. 17 also shows the cabling coming 830 from each of the idler pulleys. With seven motors, and two cables coming off of each motor for opposite direction control, there are a total of fourteen separate cables conduits at the bundle 835. The cables move within the conduits in a known manner. The conduits themselves are fixedly supported and extend from the holder 808 to the adapter 15. Again, reference may be made to FIG. 8 showing the conduit bundles at 21 and 22.

The seven motors in this embodiment control (1) one jaw of the tool J6, (2) the pivoting of the wrist at the tool J5, (3) the other jaw of the tool J7, (4) rotation of the insert J4, (5) rotation of the adaptor J3, (6) linear carriage motion J2 and (7) pivoting of the adaptor J1. Of course, fewer or lesser numbers of motors may be provided in other embodiments and the sequence of the controls may be different.

FIG. 17A illustrates another aspect of the invention—a feedback system that feeds force information from the slave station back to the master station where the surgeon is manipulating the input device. For example, if the surgeon is moving his arm to the left and this causes some resistance at the slave station, the resistance is detected at the slave station and coupled back to one of the motors at the master station to drive the input device, such as the hand assembly illustrated herein, back in the opposite direction. This provides an increased resistance to the surgeon's movements which occurs substantially instantaneously.

FIG. 17A illustrates schematically a load cell 840 that is adapted to sense cable tension. FIG. 17A shows one of the pulleys 842 associated with one of the motors 800, and cables 845 and 847 disposed about a sensing pulley 850. The sensing pulley 850 is coupled to the piezoelectric load cell 840. The load cell 840 may be disposed in a Wheatstone bridge arrangement.

Thus, if one of the motors is operating under tension, this is sensed by the load cell 840 and an electrical signal is coupled from the slave station, by way of the controller 9, to the master station to control one of the master station motors. When tension is sensed, this drives the master station motor in the opposite direction (to the direction of movement of the surgeon) to indicate to the surgeon that a barrier or some other obstacle has been encountered by the element of the slave unit being driven by the surgeon's movements.

The cabling scheme is important as it permits the motors to be located in a position remote from the adaptor and insert. Furthermore, it does not require the motor to be supported on any moving arms or the like. Several prior systems employing motor control have motors supported on moveable arms. Here the motors are separated from the active instrument area (and sterile field) and furthermore are maintained fixed in position. This is illustrated in FIG. 8E by the motor 800. FIG. 8E also illustrates a typical cabling sequence from the motor 800 through to the tool 18. Both ends of cabling 315 are secured to the motor at 842 and the motor is adapted to rotate either clockwise or counterclockwise, in order to pull the cabling in either one direction or the other. The pair of cabling operates in unison so that as one cable is pulled inwardly toward the motor, the other cable pulls outwardly. As illustrated in FIG. 8E, the cables extend over pulley 820 to other pulleys, such as the pair of pulleys 317 and control wheel 324 associated with coupler 230. From there, the mechanical drive is transferred to the control wheel 334 of the instrument insert 300, which is coupled to wheel 334 and to the output cables 606 and 607 which drive wrist rotation of the tool 18, identified in FIG. 8E by the motion J5.

Another important aspect is the use of inter-mating wheels, such as the wheels 324 and 334 illustrated in FIG. 8E. This permits essentially a physical interruption of the mechanical cables, but at the same time a mechanical drive coupling between the cables. This permits the use of an instrument insert 16 that is readily engageable with the adaptor, as well as disengagable from the adaptor 15. This makes the instrument insert 16 easily replacable and also, due to the simplicity of the instrument insert 16, it can be made disposable. Refer again to FIG. 15A which shows the complete instrument insert and its relatively simple construction, but which still provides an effective coupling between the drive motor and the tool.

Figure 19:
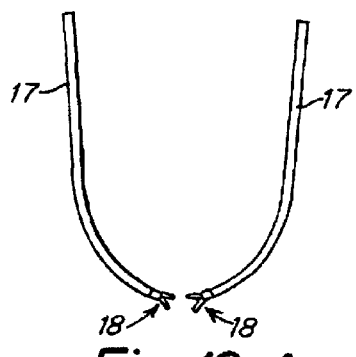
FIGS. 19A–19D are schematic diagrams showing alternate positions of the guide tube of the adapter.
Figure 19:
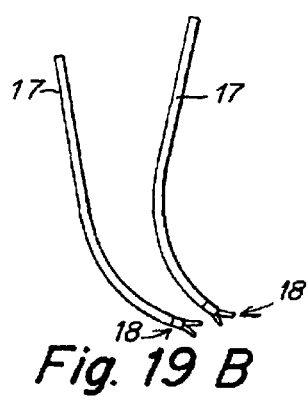
Figure 19:
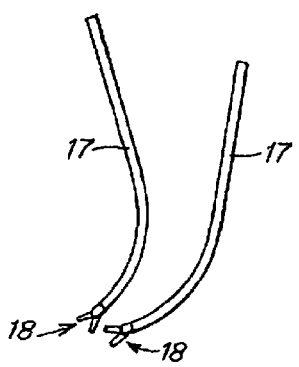
Figure 19:
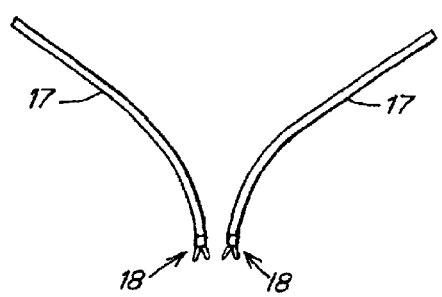

C5—Slave Guide Tube (FIGS. 19–19D)

Reference is now made to FIG. 19, a schematic diagram illustrating different placements of the guide tube 17. FIG. 19A illustrates left and right guide tubes substantially in the same position as illustrated in FIG. 1. For some surgical procedures, it may be advantageous to orient the tubes so that the curvatures are in the same direction. FIG. 19B shows the ends of the tubes pointing to the right, while FIG. 19C shows the ends of the tubes pointing to the left. Lastly, in FIG. 19D the ends of the tubes are shown converging but in a downwardly directed position. Regarding the different placements shown in FIG. 19, the adjustable clamp 25, illustrated in FIGS. 8A–8C may be useful, as this provides some added level of flexibility in supporting the positioning of the guide tubes on both the left and right side.

C6—Slave Motor Control (FIGS. 20–28)

Figure 20:
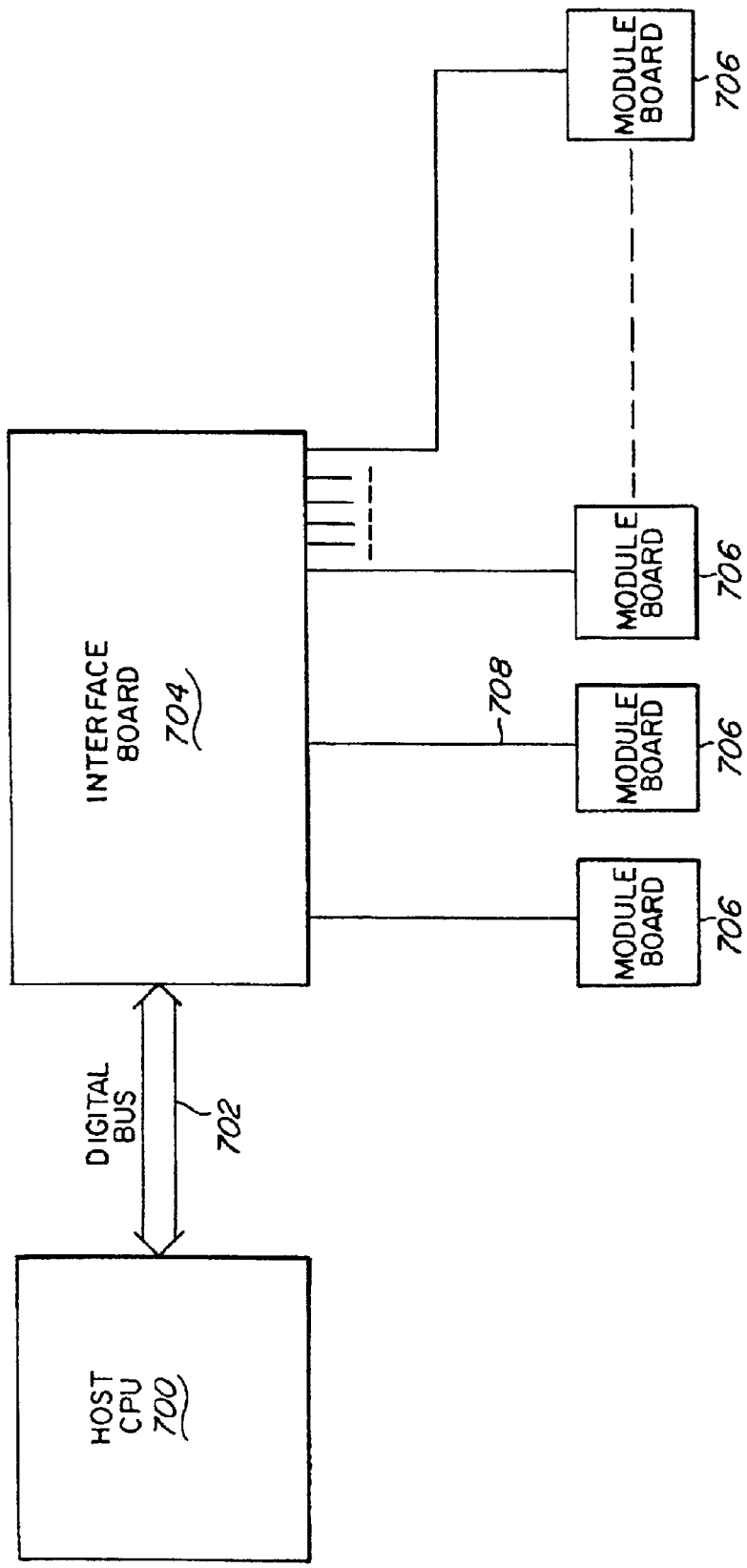
FIG. 20 is a block diagram of the controller used with the robotic system of this embodiment.
Figure 21:
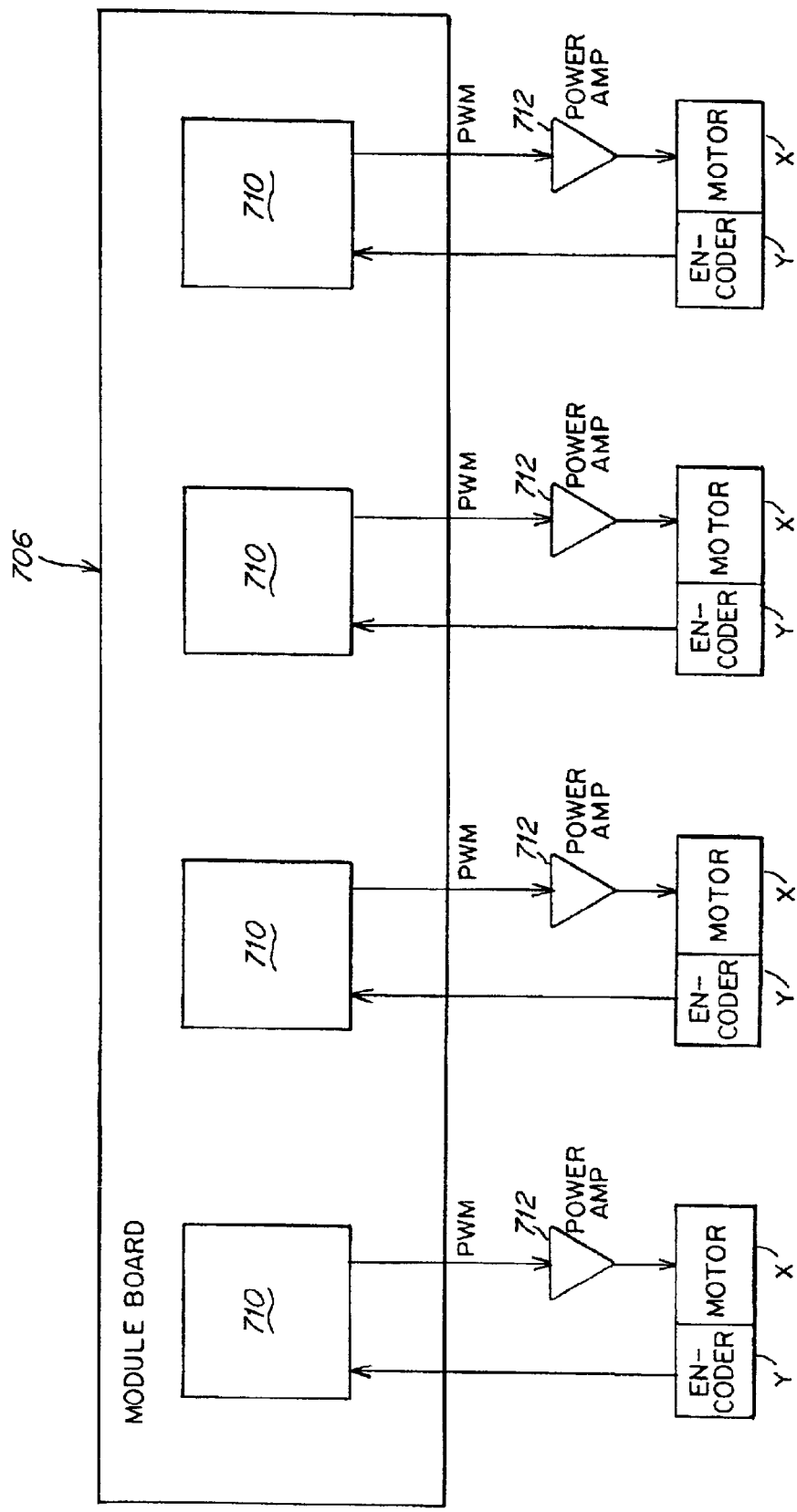
FIG. 21 is a block diagram of further details of the controller, including the module board.

FIGS. 20 and 21 are block diagrams of the motor control system of the present embodiment. In the system of FIG. 1, there are two instruments supported on either side of the operating table. Thus, there are in actuality two separate drive units 8. One of these is considered a left hand (LH) station and the other is considered a right hand (RH) station. Similarly, at the master station, on either side of the chair, as depicted in FIG. 1, there are left hand and right hand master station assemblies. Accordingly, there are a total of 28 (7×4) separate actions that are either sensed or controlled. This relates to seven separate degrees-of-motion at both the master and slave, as well as at left hand and right stations. In other embodiments there may be only a single station, such as either a left hand station or a right hand station. Also, other embodiments may employ fewer or greater numbers of degrees-of-motion as identified herein.

Regarding the master station side, there is at least one position encoder associated with each of degree-of-motion or degree-of-freedom. Also, as previously described, some of the described motions of the active joints have a combination of motor and encoder on a common shaft. With regard to the master station, all of the rotations represented by J1, J2 and J3 (see FIG. 2A) have associated therewith, not only encoders but also individual motors. At the hand assembly previously described, there are only encoders. However, the block diagram system of FIGS. 20 and 21 illustrates a combination with motor and encoder. If a motor is not used at a master station, then only the encoder signal is coupled to the system.

FIGS. 20 and 21 illustrate a multi-axis, high performance motor control system which may support anywhere from 8 to 64 axes, simultaneously, using either eight-bit parallel or pulse width modulated (PWM) signals. The motors themselves may be direct current, direct current brushless or stepper motors with a programmable digital filter/commutater. Each motor accommodates a standard incremental optical encoder.

The block diagram of FIG. 20 represents the basic components of the system. This includes a host computer 700, connected by a digital bus 702 to an interface board 704. The interface board 704 may be a conventional interface board for coupling signals between the digital bus and the eight individual module boards 706. The set of module boards is referred to as the motor control sub unit. Communication cables 708 intercouple the interface board 704 to eight separate module boards 706. The host computer 700 may be an Intel microprocessor based personal computer (PC) at a control station preferably running a Windows NT program communicating with the interface board 704 by way of a high-speed PCI bus 702 (5.0 KHz for eight channels to 700 Hz for 64 channels).

FIG. 21 shows one of the module boards 706. Each board 706 includes four motion control circuits 710. Each of the blocks 710 may be a Hewlett-Packard motion control integrated circuit. For example, each of these may be an IC identified as HCTL1100. Also depicted in FIG. 21 is a power amplifier sub unit 712. The power amplifier sub unit is based on National Semiconductor's H-bridge power amplifier integrated circuits for providing PWM motor command signals. The power amplifier 712 associated with each of the blocks 710 couples to a motor X. Associated with motor X is encoder Y. Also note the connection back from each encoder to the block 710. In FIG. 21, although the connections are not specifically set forth, it is understood that signals intercouple between the block 710 and the interface board 704, as well as via bus 702 to the host computer 700.

The motor control system may be implemented for example, in two ways. In a first method the user utilizes the motor control subunit 706 to effect four control modes: positional control, proportional velocity control, trapezoidal profile control and integral velocity control. Using any one of these modes means specifying desired positions or velocities for each motor, and the necessary control actions are computed by the motion control IC 710 of the motor control subunit, thereby greatly reducing the complexity of the control system software. However, in the case where none of the on-board control modes are appropriate for the application, the user may choose a second method in which a servo motor control software is implemented at the PC control station. Appropriate voltage signal outputs for each motor are computed by the PC control station and sent to the motor control/power amplifier unit (706, 712). Although the computation load is mostly placed on the control station's CPU in this case, there are available high performance computers and high speed PCI buses for data transfer which can accommodate this load.

D. Master—Slave Positioning and Orientation (FIGS. 22–28)

Figure 22:
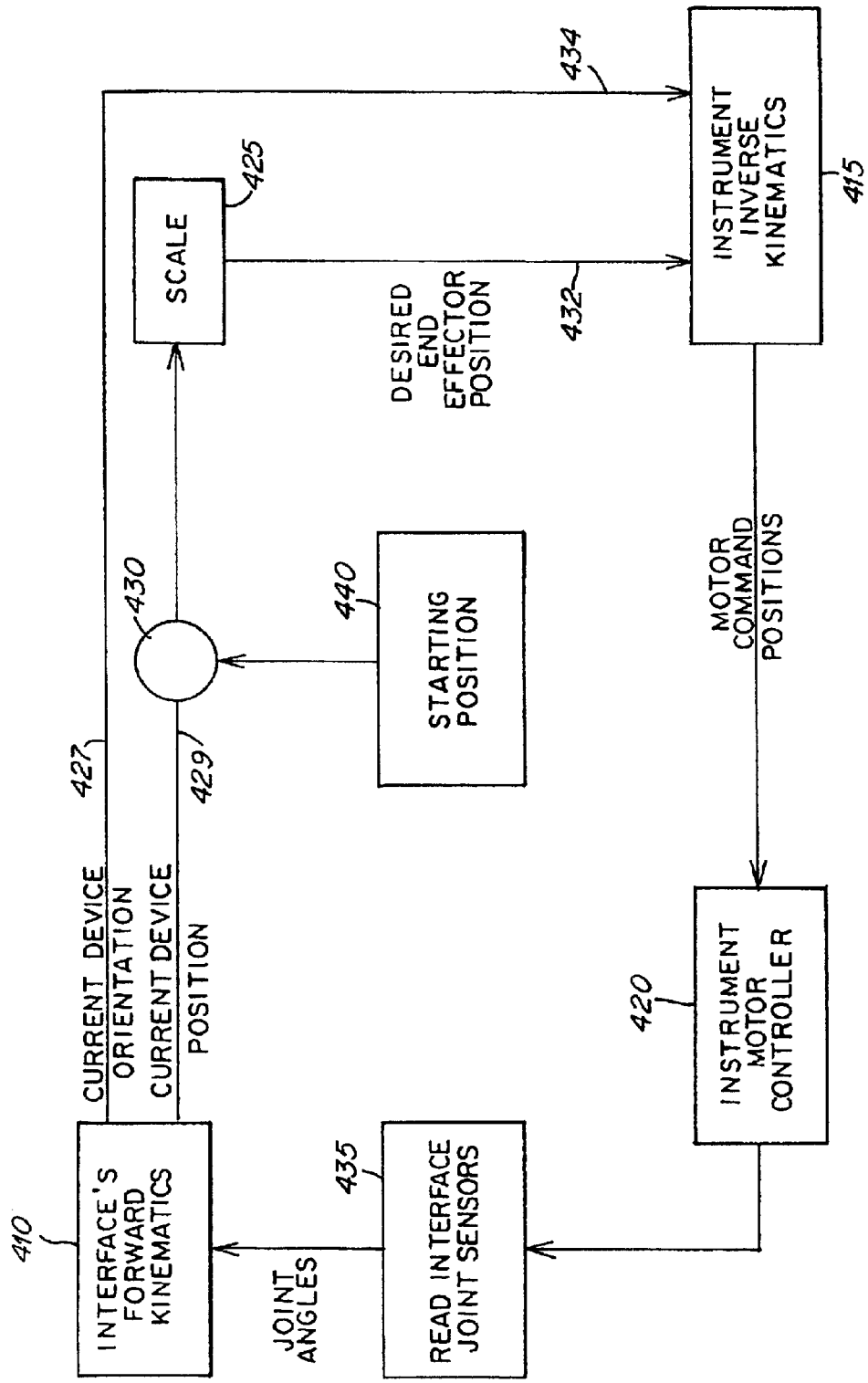
FIG. 22 is a block diagram of a control algorithm in accordance with the present embodiment.

FIG. 22 provides an overview of control algorithm for the present embodiment. Its primary function is to move the instrument tool 18 in such a way that the motions of the instrument tool are precisely mapped to that of the surgeon interface device 3 in three dimensional space, thereby creating the feel of the tool being an extension of the surgeon's own hands. The control algorithm assumes that both the surgeon's input interface as well as the instrument system always start at predefined positions and orientations, and once the system is started, it repeats a series of steps at every sampling period. The predefined positions and orientations, relate to the initial positioning of the master and slave stations.

First, the joint sensors (box 435), which are optical encoders in the present embodiment, of the surgeon's interface system are read, and via forward kinematics (box 410) analysis, the current position (see line 429) and orientation (see line 427) of the input interface handle are determined. The translational motion of the surgeon's hand motion is scaled (box 425), whereas the orientation is not scaled, resulting in a desired position (see line 432) and orientation (see line 434) for the instrument tool. The results are then inputted into the inverse kinematics algorithms (box 415) for the instrument tool, and finally the necessary joint angles and insertion length of the instrument system are determined. The motor command positions are sent to the instrument motor controller (box 420) for commending the corresponding motors to positions such that the desired joint angles and insertion length are achieved.

With further reference to FIG. 22, it is noted that there is also provided an initial start position for the input device, indicated at box 440. The output of box 440 couples to a summation device 430. The output of device 430 couples to scale box 425. The initial handle (or hand assembly) position as indicated previously is established by first positioning of the handle at the master station so as to establish an initial master station handle orientation in three dimensional space. This is compared to the current handle position at device 430. This is then scaled by box 425 to provide the desired tool position on line 432 to the instrument inverse kinematics box 415.

The following is an analysis of the kinematic computations for both box 410 and box 415 in FIG. 22.

Kinematic Computations

The present embodiment provides a surgeon with the feel of an instrument as being an extension of his own hand. The position and orientation of the instrument tool is mapped to that of the surgeon input interface device, and this mapping process is referred to as kinematic computations. The kinematic calculations can be divided into two sub-processes: forward kinematic computation of the surgeon user interface device, and inverse kinematic computation of the instrument tool.

Forward Kinematic Computation

Based on the information provided by the joint angle sensors, which are optical encoders of the surgeon interface system, the forward kinematic computation determines the position and orientation of the handle in three dimensional space.

1. Position

Figure 23:
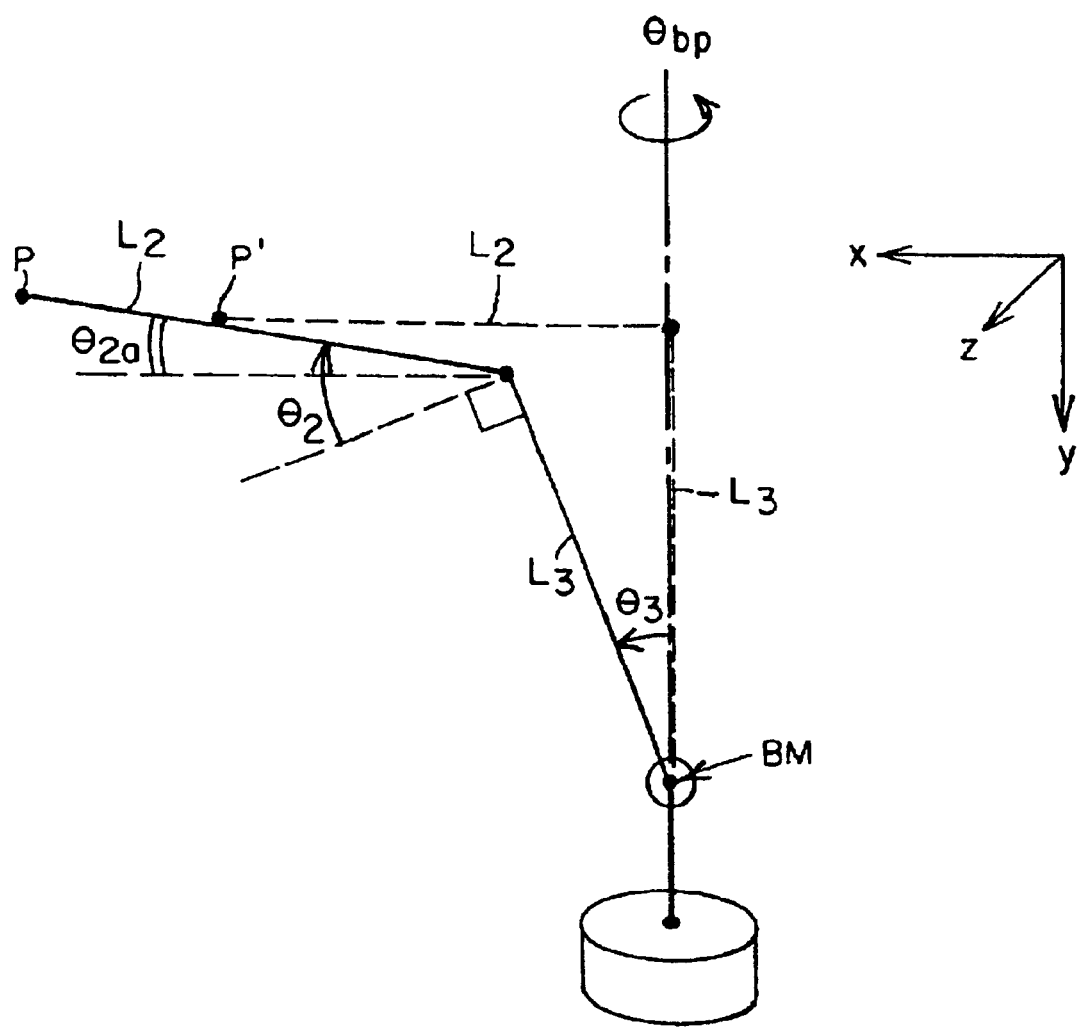
FIGS. 23–28 are a series of schematic diagrams of the input device position and resulting instrument position relating to the algorithm control of the present embodiment.

The position of the surgeon's wrist in three dimensional space is determined by simple geometric calculations. Referring to FIG. 23, the x, y, z directional positions of the wrist with respect to the reference coordinate are $X_p = (L_3 \sin \theta_3 + L_2 \cos \theta_{2a}) \cos \theta_{bp} - L_2$ $Y_p = -(L_3 \cos \theta_3 + L_2 \sin \theta_{2a}) - L_3$ $Z_p = (L_3 \sin \theta_3 + L_2 \cos \theta_{2a}) \sin \theta_{bp}$ where $X_p$, $Y_p$, $Z_p$ are wrist positions in the x, y, z directions, respectively.

These equations for $X_p$, $Y_p$, and $Z_p$ represent respective magnitudes as measured from the initial reference coordination location, which is the location in FIG. 23 when $\theta_3$ and $\theta_{2a}$ are both zero degrees. This corresponds to the position wherein arm L2 is at right angles to arm L3, i.e., arm L2 is essentially horizontal and arm L3 is essentially vertical. That location is identified in FIG. 23 as coordinate location P' where $X_p = Y_p = Z_p = 0$. Deviations from this reference are calculated to determine the current position P.

Figure 25:
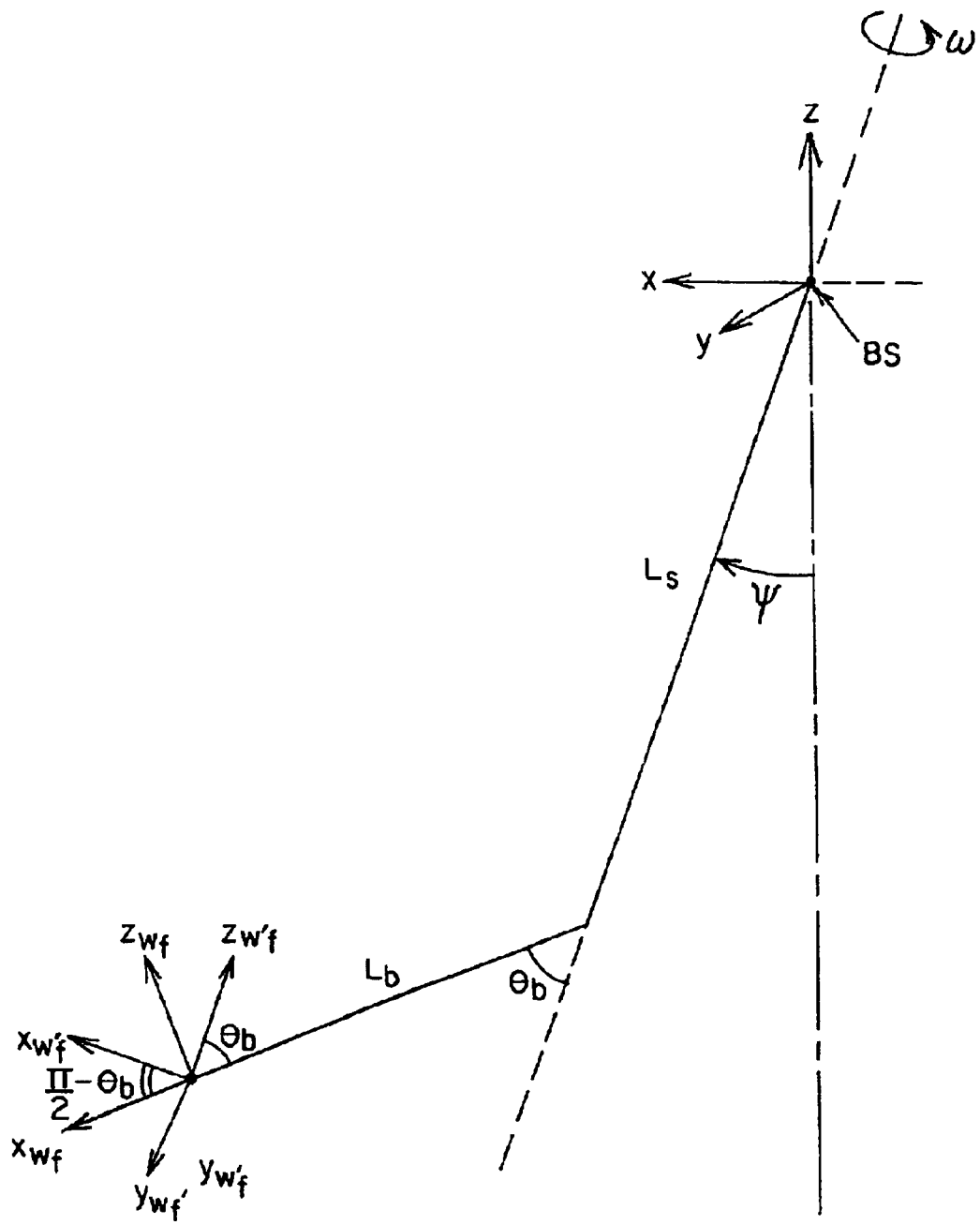

The reference coordinates for both the master and the slave are established with respect to a base location for each. In FIG. 23 it is location BM that corresponds structurally to the axis 60A in FIG. 2A. In FIG. 25 it is the location BS that corresponds structurally to the axis 225A in FIG. 2B. Because both the master and slave structures have predefined configurations when they are initialized, the locations of the master wrist 60A and the slave pivot 225A are known by the known dimensions of the respective structures. The predefined configuration of the master in the illustrated embodiment, per FIG. 23, relates to known lengths of arms L2 and L3, corresponding to arm 91 or arm 92, and arm 96 respectively. The predefined configuration of the slave is similarly defined, per FIG. 25, by dimensions of arms $L_s$ and $L_b$ and by initializing the slave unit with the guide tube 17 flat in one plane (dimension Y=O) and the arm $L_s$ in line with the Z axis.

2. Orientation

Figure 24A:
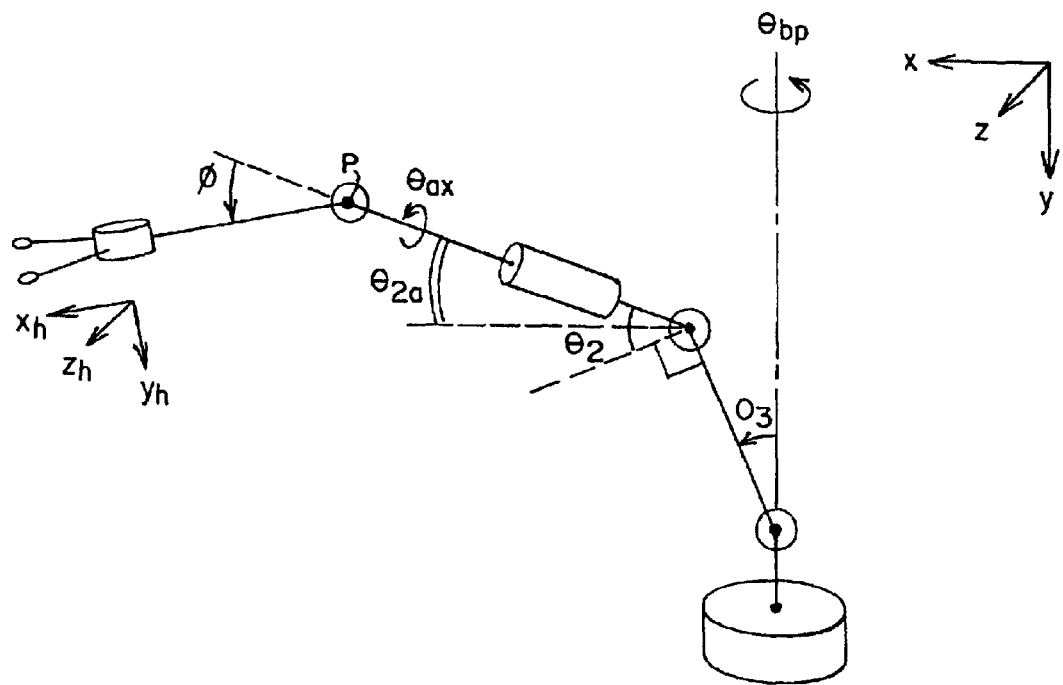
Figure 24B:
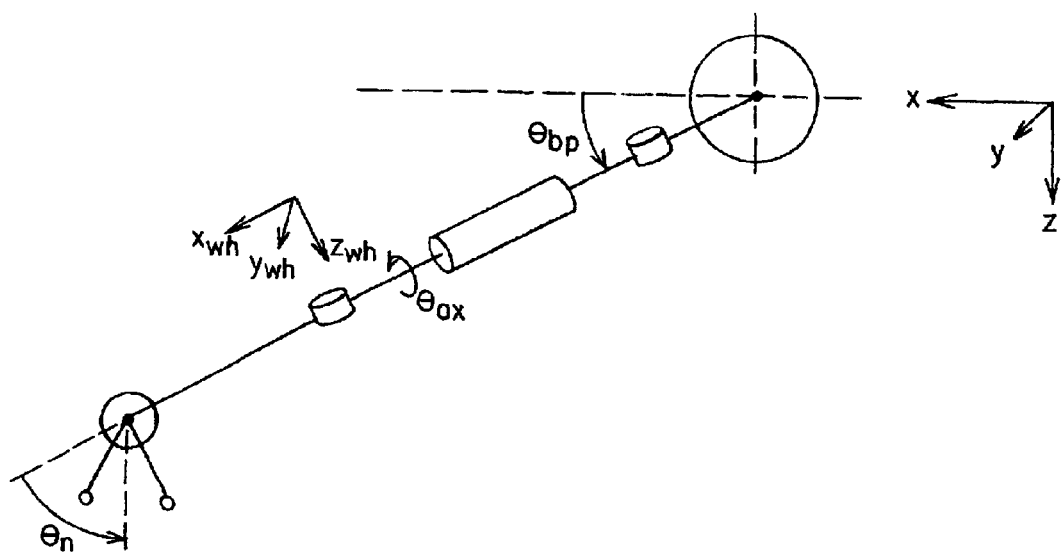

The orientation of the surgeon interface handle in three dimensional space is determined by a series of coordinate transformations for each joint angle. As shown in FIG. 24, the coordinate frame at the wrist joint is rotated with respect to the reference coordinate frame by joint movements $\theta_{bp}$, $\theta_2$, $\theta_3$ and $\theta_{ax}$. Specifically, the wrist joint coordinate frame is rotated $(-\theta_{bp})$ about the y axis, $(-\theta_{2a})$ about the z axis and $\theta_{ax}$ about the x axis where $\theta_{2a}$ is $\theta_2 - \theta_3$. The resulting transformation matrix $R_{wh}$ for the wrist joint coordinate frame with respect to the reference coordinate is then $$R_{wh} = \begin{bmatrix} R_{wh11} & R_{wh12} & R_{wh13} \\ R_{wh21} & R_{wh22} & R_{wh23} \\ R_{wh31} & R_{wh32} & R_{wh33} \end{bmatrix}$$

where $R_{wh11} = \cos \theta_{bp1} \cos \theta_{2a}$
$R_{wh12} = \cos \theta_{bp1} \sin \theta_{2a} \cos \theta_{ax} - \sin \theta_{bp1} \sin \theta_{ax}$
$R_{wh13} = -\cos \theta_{bp1} \sin \theta_{2a} \sin \theta_{ax} - \sin \theta_{bp1} \cos \theta_{ax}$
$R_{wh21} = -\sin \theta_{2a}$
$R_{wh22} = \cos \theta_{2a} \cos \theta_{ax}$
$R_{wh23} = -\cos \theta_{2a} \sin \theta_{ax}$
$R_{wh31} = \sin \theta_{bp1} \cos \theta_{2a}$
$R_{wh32} = \sin \theta_{bp1} \sin \theta_{2a} \cos \theta_{ax} + \cos \theta_{bp1} \sin \theta_{ax}$
$R_{wh33} = -\sin \theta_{bp1} \sin \theta_{2a} \sin \theta_{ax} + \cos \theta_{bp1} \cos \theta_{ax}$ Similarly, the handle coordinate frame rotates joint angles $\phi$ and $(-\theta_h)$ about the z and y axes with respect to the wrist coordinate frame. The transformation matrix $R_{hwh}$ for handle coordinate frame with respect to the wrist coordinate is then $$R_{hwh} = \begin{bmatrix} R_{hwh11} & R_{hwh12} & R_{hwh13} \\ R_{hwh21} & R_{hwh22} & R_{hwh23} \\ R_{hwh31} & R_{hwh32} & R_{hwh33} \end{bmatrix}$$

where $R_{hwh11} = \cos \phi \cos \theta_h$
$R_{hwh12} = -\sin \phi$
$R_{hwh13} = -\cos \phi \sin \theta_h$
$R_{hwh21} = \sin \phi \cos \theta_h$
$R_{hwh22} = \cos \phi$
$R_{hwh23} = -\sin \phi \sin \theta_h$
$R_{hwh31} = \sin \theta_h$
$R_{hwh32} = 0$
$R_{hwh33} = \cos \theta_h$ Therefore, the transformation matrix $R_h$ for handle coordinate frame with respect to the reference coordinate is $R_h = R_{wh} R_{hwh}$

Inverse Kinematic Computation

Once the position and orientation of the surgeon interface handle are computed, the instrument tool is to be moved in such a way that the position of the tool's wrist joint in three dimensional space $X_w$, $Y_w$, $Z_w$ with respect to the insertion point are proportional to the interface handle's positions by a scaling factor $\alpha$ $(X_w - X_{w\_ref}) = \alpha X_p$ $(Y_w - Y_{w\_ref}) = \alpha Y_p$ $(Z_w - Z_{w\_ref}) = \alpha Z_p$ where $X_{w\_ref}$, $Y_{w\_ref}$, $Z_{w\_ref}$ are the initial reference positions of the wrist joint. The orientations could be scaled as well, but in the current embodiment, are kept identical to that of the interface handle.

When $X_{w\_ref} = Y_{w\_ref} = Z_{w\_ref} = 0$ the foregoing equations simplify to:
$X_w = \alpha X_p$
$Y_w = \alpha Y_p$
$Z_w = \alpha Z_p$
where $(X_w, Y_w, Z_w)$, $(X_p, Y_p, X_p)$ and $\alpha$ are the desired absolute position of the instrument, current position of the interface handle and scaling factor, respectively.

1. Position

The next task is to determine the joint angles $\omega$, $\Psi$ and the insertion length $L_s$ of the instrument, as shown in FIG. 25, necessary to achieve the desired positions of the tool's wrist joint. Given $Y_w$, the angle $\omega$ is $$\omega = \arcsin\left(\frac{Y_w}{L_{bs}}\right) \omega = \sin^{-1}(Y_w/L_{bs}) \text{ or,}$$

where $L_{bs} = L_b \sin \theta_b$.

Figure 26:
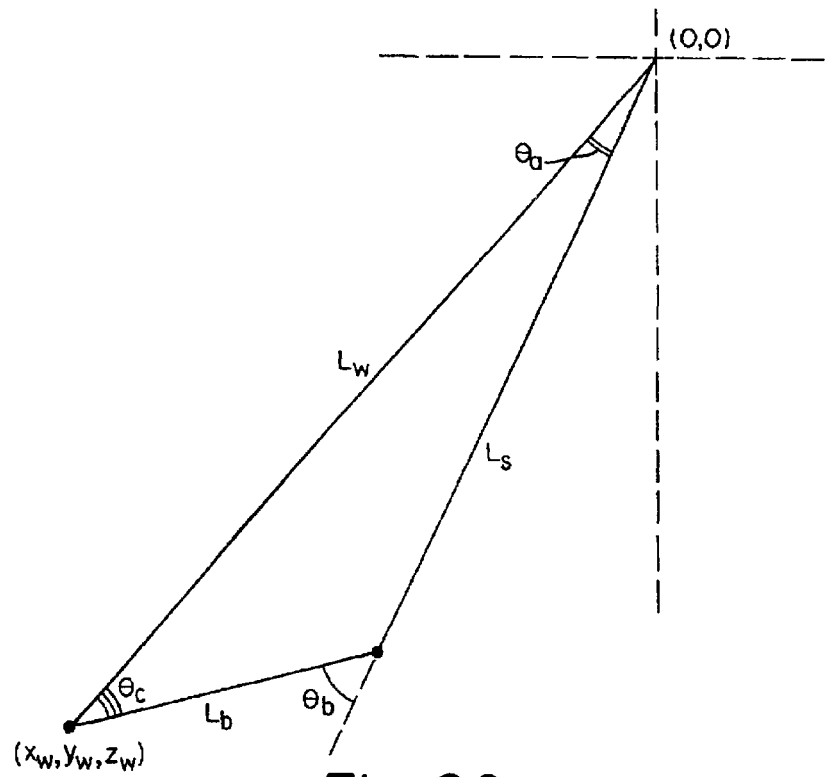

Referring to FIG. 26, the sine rule is used to determine the insertion length $L_s$ of the instrument. Given the desired position of the tool's wrist joint, the distance from the insertion point to the wrist joint, $L_{ws}$ is simply $L_w = \sqrt{X_w^2 + Y_w^2 + Z_w^2}$ Then by the sine rule, the angle $\theta_a$ is $$\theta_a = \arcsin\left(\frac{L_b}{L_w}\sin\theta_b\right), \text{ and } L_s = L_w\left(\frac{\sin\theta_c}{\sin\theta_b}\right) \text{ where } \theta_c = \theta_b - \theta_a$$

Figure 27:
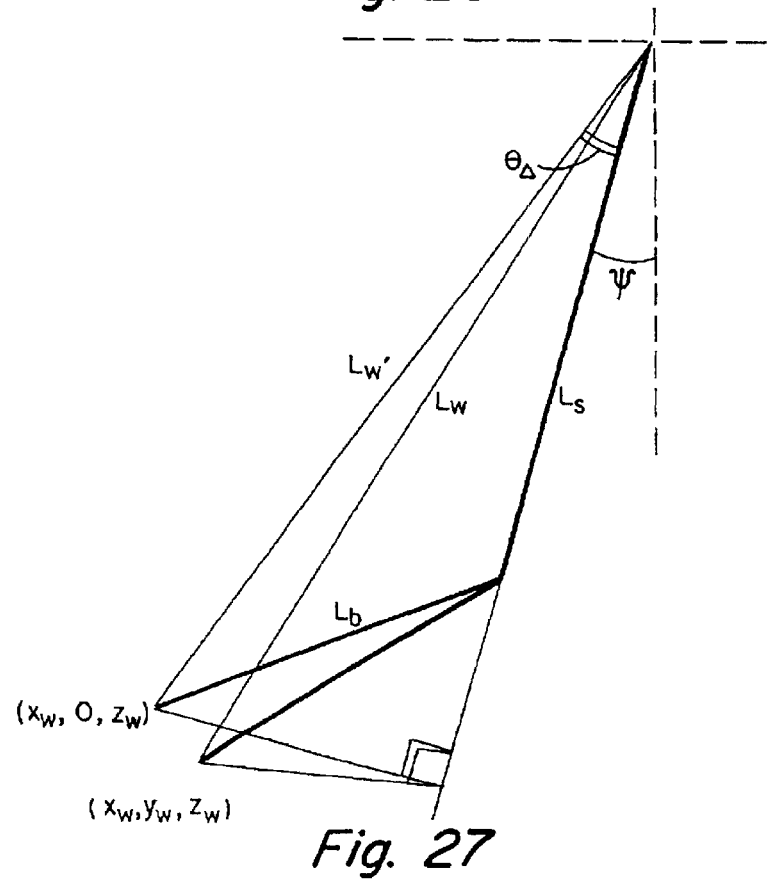

Having determined $\omega$ and $L_s$, the last joint angle $\Psi$ can be found from the projection of the instrument on the x-z plane as shown in FIG. 27.

$$\theta_\Delta = \arccos\left(\frac{L_s + L_b\cos\theta_b}{L'_w}\right),$$

$$\theta_{L'_w} = \arcsin\left(\frac{X_{wo}}{L'_w}\right),$$

$$L'_w = \sqrt{X_w^2 + Z_w^2}$$

and $X_{wo}$ is the x-axis wrist position in reference coordinate frame.

2. Orientation

The last step in kinematic computation for controlling the instrument is determining the appropriate joint angles of the tool such that its orientation is identical to that of the surgeon's interface handle. In other words, the transformation matrix of the tool must be identical to the transformation matrix of the interface handle, $R_h$.

Figure 28:
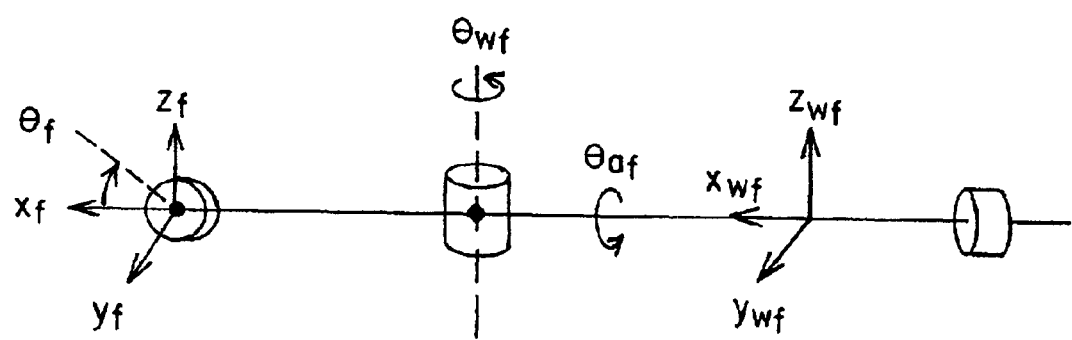

The orientation of the tool is determined by pitch ($\theta_f$), yaw ($\theta_{wf}$) and roll ($\theta_{af}$) joint angles as well as the joint angles $\omega$ and $\Psi$, as shown in FIG. 28. First, the starting coordinate is rotated ($\theta_b$, $-\pi/2$) about the y-axis to be aligned with the reference coordinate, represented by the transformation matrix $R_o$ $$R_o = \begin{bmatrix} \sin\theta_b & 0 & (-\cos\theta_b) \\ 0 & 1 & 0 \\ \cos\theta_b & 0 & \sin\theta_b \end{bmatrix}$$

The wrist joint coordinate is then rotated about the reference coordinate by angles ($-\Psi$) about the y-axis and $\omega$ about the z-axis, resulting in the transformation matrix $R_{w'f}$ $$R_{w'f} = \begin{bmatrix} \cos\Psi\cos\omega & (-\cos\Psi\sin\omega) & (-\sin\Psi) \\ \sin\omega & \cos\omega & 0 \\ \sin\Psi\cos\omega & (-\sin\Psi\sin\omega) & \cos\Psi \end{bmatrix}$$

followed by rotation of ($\pi/2-\theta_b$) about the y-axis, represented by $R_{wfw'f}$ $$R_{wfw'f} = \begin{bmatrix} \sin\theta_b & 0 & \cos\theta_b \\ 0 & 1 & 0 \\ -\cos\theta_b & 0 & \sin\theta_b \end{bmatrix} \text{ which is equal to } R_o^T.$$

Finally, the tool rolls ($-\theta_{af}$) about the x-axis, yaws $\theta_{wf}$ about the z-axis and pitches ($-\theta_f$) about the y-axis with respect to the wrist coordinate, are calculated resulting in transformation matrix $R_{fwf}$ $$R_{fwf} = \begin{bmatrix} R_{fwf11} & R_{fwf12} & R_{fwf13} \\ R_{fwf21} & R_{fwf22} & R_{fwf23} \\ R_{fwf31} & R_{fwf32} & R_{fwf33} \end{bmatrix}$$

where $R_{fwf11}=\cos\theta_{wf}\cos\theta_f$
$R_{fwf12}=-\sin\theta_{wf}$
$R_{fwf13}=-\cos\theta_{wf}\sin\theta_f$
$R_{fwf21}=\cos\theta_{af}\sin\theta_{wf}\cos\theta_f+\sin\theta_{af}\sin\theta_f$
$R_{fwf22}=\cos\theta_{af}\cos\theta_{wf}$
$R_{fwf23}=-\cos\theta_{af}\sin\theta_{wf}\sin\theta_f+\sin\theta_{af}\cos\theta_f$
$R_{fwf31}=-\sin\theta_{af}\sin\theta_{wf}\cos\theta_f+\cos\theta_{af}\sin\theta_f$
$R_{fwf32}=-\sin\theta_{af}\cos\theta_{wf}$
$R_{fwf33}=\sin\theta_{af}\sin\theta_{wf}\sin\theta_f+\cos\theta_{af}\cos\theta_f$ Therefore the transformation matrix of the tool $R_f$ with respect to the original coordinate is
$R_f = R_o R_{wf} R_o^T R_{fwf}$
Since $R_f$ is identical to $R_h$ of the interface handle, $R_{fwf}$ can be defined by
$R_{fwf} = R_o R_{wf}^T R_o^T R_h = R_c$ $$R_{fwf} = R_o R_{wf}^T R_o^T R_h = R_c = \begin{bmatrix} R_{c11} & R_{c12} & R_{c13} \\ R_{c21} & R_{c22} & R_{c23} \\ R_{c31} & R_{c32} & R_{c33} \end{bmatrix}$$

where the matrix $R_c$ can be fully computed with known values. Using the computed values of $R_c$ and comparing to the elements of $R_{fwf}$, we can finally determine the necessary joint angles of the tool.

$$\theta_{wf} = \arcsin(-R_{c12}),$$

$$\theta_f = \arccos\left(\frac{R_{c11}}{\cos\theta_{wf}}\right) = \arcsin\left(\frac{-R_{c13}}{\cos\theta_{wf}}\right)$$

$$\theta_{af} = \arccos\left(\frac{R_{c22}}{\cos\theta_{wf}}\right) = \arcsin\left(\frac{-R_{c32}}{\cos\theta_{wf}}\right)$$

The actuators, which are motors in the current embodiment, are then instructed to move to positions such that the determined joint angles and insertion length are achieved.

Now reference is made to the following algorithm that is used in association with the system of the present invention. First are presented certain definitions.

| Variable Definitions: (RH - Right Hand, LH - Left Hand) | |
|---|---|
| s_Ls_RH | Linear slider joint for RH slave |
| s_Xi_RH | Lateral motion joint for RH slave (big disk in front of slider) |
| s_Omega_RH | Up/down motion joint for RH slave (rotates curved tube) |
| s_Axl_RH | Axial rotation joint for RH slave (rotates instrument insert along its axis) |
| s_f1_RH | Finger 1 for RH slave |
| s_f2_RH | Finger 2 for RH slave |
| s_wrist_RH | Wrist joint for RH slave |
| m_base_RH | Base rotation joint for RH master |
| m_shoulder_RH | Shoulder joint for RH master |
| m_elbow_RH | Elbow joint for RH master |
| m_Axl_RH | Axial rotation joint for RH master |
| m_f1_RH | Finger 1 for RH master |
| m_f2_RH | Finger 2 for RH master |
| m_wrist_RH | Wrist joint for RH master |
| Radian[i] | Motor axle angle for joint no. i with i being one of above joints |
| Des_Rad[i] | Desired motor axle angle for joint no. i |
| Des_Vel[i] | Desired motor axle angular velocity for joint no. i |
| Mout_f[i] | Motor command output for joint no. i |
| Thetabp1_m_RH | Angle of base rotation joint for RH master |

| Variable Definitions: (RH - Right Hand, LH - Left Hand) | |
|---|---|
| ⑩Theta2_m_RH | Angle of elbow joint for RH master |
| ⑩Theta3_m_RH | Angle of shoulder joint for RH master |
| ⑩Xw_m_RH | Position of RH master handle in X-axis |
| ⑩Yw_m_RH | Position of RH master handle in Y-axis |
| ⑩Zw_m_RH | Position of RH master handle in Z-axis |
| ⑩Xwref_m_RH | Reference position of RH master handle in X-axis |
| ⑩Ywref_m_RH | Reference position of RH master handle in Y-axis |
| ⑩Zwref_m_RH | Reference position of RH master handle in Z-axis |
| ⑩Phi_f_m_RH | Angle of wrist joint for RH master |
| ⑩Theta_f1_m_RH | Angle of finger 1 for RH master |
| ⑩Theta_f2_m_RH | Angle of finger 2 for RH master |
| ⑩ThetaAxl_m_RH | Angle of axial rotation joint for RH master |
| ⑩Theta_h_m_RH | Angle of mid line of fingers for RH master |
| ⑩Theta_f_m_RH | Angle of fingers from the mid line for RH master |
| ⑩Xw_s_RH | Position of RH slave in X-axis |
| ⑩Yw_s_RH | Position of RH slave in Y-axis |
| ⑩Zw_s_RH | Position of RH slave in Z-axis |
| ⑩Xwref_s_RH | Reference position of RH slave in X-axis |
| ⑩Ywref_s_RH | Reference position of RH slave in Y-axis |
| ⑩Zwref_s_RH | Reference position of RH slave in Z-axis |
| ⑩alpha | Master-to-slave motion scaling factor |
| ⑩Xw_s_b1_RH | Motion boundary 1 of RH slave in X-axis |
| ⑩Xw_s_b2_RH | Motion boundary 2 of RH slave in X-axis |
| ⑩Yw_s_b1_RH | Motion boundary 1 of RH slave in Y-axis |
| ⑩Yw_s_b2_RH | Motion boundary 2 of RH slave in Y-axis |

Note the motion boundaries of the slave are used to define the virtual boundaries for the master system, and do not directly impose boundaries on the slave system.

The following represents the steps through which the algorithm proceeds.

1. The system is started, and the position encoders are initialized to zero. This ASSUMES that the system started in predefined configuration.

```
/* Preset Encoder Position for all axis */
for(i=0; i<32; ++i)
{
    SetEncoder[i]=0;
}
/* Convert encoder count to radian */
for(i=0;i<32;i++)
{
    Radian[i] = Enc_to_Rad(Encoder[i]);
}
```

2. Bring the system to operating positions, Des_Rad[i], and hold the positions until the operator hits the keyboard, in which case the program proceeds to next step.

```
While(!kbhit())
{
    for(i=0;i<14;i++)   /* compute motorout for slave robots*/
    {
        Des_Vel[i]= 0.0;
        Err_Rad[i] = Des Rad[i] – Radian[i];
        Err_Vel[i] = Des Vel[i] – Velocity[i];
        kpcmd = Kp[i]*Err_Rad[i];
        kdcmd = (Kp[i]*Td[i])*Err_Vel[i];
        Mout_f[i] =kpcmd + kdcmd;/* Command output to motor */
    }
    for(i=14;i<28;i++)    /* compute motorout for master robot */
    {
        Des_Vel[i] = 0.0;
        Err_Rad[i] = Des_Rad[i] – Radian[i];
        Err_Vel[i] = Des_Vel[i] – Velocity[i];
        kpcmd = Kp[i]*Err_Rad[i];
        kdcmd = (Kp[i]*Td[i]) *Err_Vel[i];
        Mout_f[i] = kpcmd + kdcmd;/* Command output to motor */
    }
}
```

3. Based on the assumption that the system started at the predefined configuration, the forward kinematic computations are performed respectively for the master and the slave systems to find the initial positions/orientations of handles/tools.

/* Compute Initial Positions of Wrist for Right Hand Master */
Thetabp1o_m_RH =–Radian[m_base_RH]/PR_bp1;
Theta3o_m_RH=–Radian[m_shoulder_RH]/PR_3;
Thetabp1_m_RH =Thetabp1o_m_RH;
Theta3_m_RH=Theta3o_m_RH;
Theta2o_m_RH =Theta3o_m_RH–Radian[m_elbow_RH]/PR_2;
Theta2_m_RH=Theta2o_m_RH;
Theta2A_m_RH=(Theta2_m_RH–Theta3_m_RH);
Theta2A_eff_m_RH=Theta2A_m_RH+Theta_OS_m;
L_m_RH=(L3_m*sin(Theta3o_m_RH)+L2_eff_m*cos(Theta2A_eff_m_RH));
Xwo_m_RH=L_m_RH*cos(Thetabp1o_m_RH);
Ywo_m_RH=–(L3_m+L2_eff m*sin(Theta2A_eff_m_RH));
Zwo_m_RH=L_m_RH*sin(Thetabp1o_m_RH);
/* Set these initial positions as the reference positions. */
Xwref_m_RH=Xwo_m_RH=L2 (FIG. 23)
Ywref_m_RH=Ywo_m_RH=L3
Zwref_m_RH=Zwo_m_RH=0
/* Initial Position of the Wrist for Right Hand Slave based on predefined configurations */
Ls_RH=Ls;
Xwo_s_RH=Lbs=X ref_s_RH
Ywo_s_RH=0.0=Yref_s_RH
Zwo_s_RH=—(Ls_RH+Lbc)=Zref_s_RH
/* Compute Initial Orientations for Right Hand Handle */
Phi_f_m_RH=Radian[m_wrist_H];
Theta_f1_m_RH=Radian[m_f1_RH];
Theta_f2_m_RH=–Radian[m_f2_RH]–Theta_f1_m_RH;
ThetaAx1_m_RH=Radian[m_Ax1_RH];
Theta_h_m_RH=(Theta_f1_m_RH–Theta_f2_m_RH)/2.0; /* angle of midline
Theta_f_m_RH=(Theta_f1_m_RH+Theta_f2_m_RH)/2.0; /* angle of finger from mid line */
/* Repeat for Left Hand Handle and Slave Instrument */

4. Repeat the procedure of computing initial positions/orientations of handle and tool of left hand based on predefined configurations.

5. Read starting time
/* Read starting time: init_time */
QueryPerformanceCounter(&hirescount);
dCounter=(double)hirescount.LowPart+(double)hirescount.HighPart * (double)(4294967296);
QueryPerformanceFrequency(&freq);
init_time=(double)(dCounter/freq.LowPart);
prev_time=0.0;

6. Read encoder values of master/slave system, and current time

```
/* Read encoder counters */
for(i=1; i<9; ++i)
{
    Read_Encoder(i);
}
/* Convert encoder counts to radian */
for(i=0;i<32;i++)
{
    Radian[i] = Enc_to_Rad(Encoder[i]);
}
/* Get current time */
QueryPerformanceCounter(&hirescount);
dCounter = (double)hirescount.LowPart + (double)hirescount.HighPart * (double)(4294967296);
time_now = (double)(dCounter/freq.LowPart) - init_time;
delta_time3 = delta_time2;
delta_time2 = delta_time1;
delta_time1 = time_now - prev_time;
prev_time = time_now;
```

7. Compute current positions/orientations of master handle for Right Hand
/* Compute master handle's position for right hand */
Thetabp1_m_RH=-Radian[m_base_RH]/PR_bp1;
Theta3_m_RH=-Radian[m_shoulder_RH]/PR_3;
Theta2_m_RH=Theta3_m_RH-Radian[m_elbow_RH]/PR_2;
Theta2A_m_RH=(Theta2_m_RH-Theta3_m_RH);
Theta2A_eff_m_RH=Theta2A_m_RH+Theta_OS_m;
L_m_RH=(L3_m*sin_Theta3_m+L2_eff_m*cos_Theta2A_eff_m);
Xw_m_RH=L_m_RH*cos_Thetabp1_m;
Yw_m_RH=-(L3_m*cos_Theta3_m+L2_eff_m*sin_Theta2A_eff$_s$_m);
Zw_m_RH=L_m_RH*sin_Thetabp1_m;
/* Compute master handle's orientation for right hand */
Phi_f_m_RH=Radian[m_wrist_RH];
Theta_f$_1$_m_RH=Radian[m_f1_RH];
Theta_f2_m_RH=-Radian[m_f2_RH]-Theta_f1_m_RH;
ThetaAx1_m_RH=Radian[m_Ax1_RH];
Theta_h_m_RH=(Theta_f1_m_RH-Theta_f2_m_RH)/2.0; /* angle of midline */
Theta_f_m_RH=(Theta_f1_m_RH+Theta_f2_m_RH)/2.0; /* angle of fingers from mid line */
/* Perform coordinate transformation to handle's coordinate */
Rwh11=cos_Thetabp1_m*cos_Theta2A_m;
Rwh12=-sin_Thetabp1_m*sin_ThetaAx1_m+cos_Thetabp1_m*sin_Theta2A_m*cos_ThetaAx1_m;
Rwh13=-sin_Thetabp1_m*cos_ThetaAx1_m-cos_Thetabp1_m*sin_Theta2A_m*sin_ThetaAx1_m;
Rwh21=-sin_Theta2A_m;
Rwh22=cos_Theta2A_m*cos_ThetaAx1_m;
Rwh23=-cos_Theta2A_m*sin_ThetaAx1_m;
Rwh31=sin_Thetabp1_m*cos_Theta2A_m;
Rwh32=cos_Thetabp1_m*sin_ThetaAx1_m+sin_Thetabp1_m*sin_Theta2A_m*cos_ThetaAx1_m;
Rwh33=cos_Thetabp1_m*cos_ThetaAx1_m-sin_Thetabp1_m*sin_Theta2A_m*sin_ThetaAx1_m;
Rhr11=cos_Phi_f_m*cos_Theta_h_m;
Rhr12=-sin_Phi_f_m;
Rhr13=-cos_Phi_f_m*sin_Theta_h_m;
Rhr21=sin_Phi_f_m*cos_Theta_h_m;
Rhr22=cos_Phi_f_m;
Rhr23=-sin_Phi_f_m*sin_Theta_h_m;
Rhr31=sin_Theta_h_m;
Rhr32=0.0;
Rhr33=cos_Theta_h_m;
Rh11=Rwh11*Rhr11+Rwh12*Rhr21+Rwh13 *Rhr31;
Rh12=Rwh11*Rhr12+Rwh12*Rhr22+Rwh13*Rhr32;
Rh13=Rwh11*Rhr13+Rwh12*Rhr23+Rwh13*Rhr33;
Rh21=Rwh21*Rhr11+Rwh22*Rhr21+Rwh23*Rhr31;
Rh22=Rwh21*Rhr12+Rwh22*Rhr22+Rwh23*Rhr32;
Rh23=Rwh21*Rhr13+Rwh22*Rhr23+Rwh23*Rhr33;
Rh31=Rwh31*Rhr11+Rwh32*Rhr21+Rwh33*Rhr31;
Rh32=Rwh31*Rhr12+Rwh32*Rhr22+Rwh33*Rhr32;
Rh33=Rwh31*Rhr13+Rwh32*Rhr23+Rwh33*Rhr33;

8. Desired tool position is computed for right hand
/* Movement of master handle is scaled by alpha for tool position */
Xw_s_RH=alpha*(Xw_m_RH-Xwref_m_RH)+Xwref_s_RH;
Yw_s_RH=alpha*(Yw_m_RH-Ywref_m_RH)+Ywref_s_RH;
Zw_s_RH=alpha*(Zw_m_RH-Zwref_m_RH)+Zwref_s_RH;
/* The next step is to perform a coordinate transformation from the wrist coordinate (refer to FIG. 25 and coordinate Xwf, Ywf and Zwf) to a coordinate aligned with the tube arm Ls. This is basically a fixed 45° transformation (refer in FIG. 25 to $θ_b$) involving the sin and cos of $θ_b$ as expressed below. */
Xwo_s_RH=Xw_s_RH*sin_Theta_b+Zw_s_RH*cos_Theta_b;
Ywo_s_RH=Yw_s_RH;
Zwo_s_RH=-Xw_s_RH*cos_Theta_b+Zw_s_RH*sin_Theta_b;

9. Perform inverse kinematic computation for the right hand to obtain necessary joint angles of the slave system such that tool position/orientation matches that of master handle.
Omega_RH=asin(Ywo_s_RH/Lbs);
Lw=sqrt(pow(Xwo_s_RH,2)+pow(Ywo_s_RH,2)+pow(Zwo_s_RH,2));
Theta_a=asin(Lb/Lw*sin_Theta_b);
Theta_c=Theta_b-Theta_a;
Ls_RH=Lw*(sin(Theta_c)/sin_Theta_b);
Lwp=sqrt(pow(Lw,2)-pow(Ywo_s_RH,2));
Theta_Lwp=asin(Xwo_s_RH/Lwp);
Xi_RH=Theta_Lwp-Theta_delta;
sin_Omega=sin(Omega_RH);
cos_Omega=cos(Omega_RH);
sin_Xi=sin(Xi_RH);
cos_Xi=cos(Xi_RH);
Ra11=cos_Xi*cos_Omega*sin_Theta_b+sin_Xi*cos_Theta_b;
Ra12=sin_Omega*sin_Theta_b;
Ra13=sin_Xi*cos_Omega*sin_Theta_b-cos_Xi*cos_Theta_b;
Ra21=-cos_Xi*sin_Omega;
Ra22=cos_Omega;
Ra23=-sin Xi*sin_Omega;
Ra31=cos_Xi*cos_Omega*cos_Theta_b-sin_Xi*sin_Theta_b;
Ra32=sin_Omega*cos_Theta_b;
Ra33=sin_Xi*cos_Omega*cos_Theta_b+cos_Xi*sin_Theta_b;
Rb11=Ra11*sin_Theta_b-Ra13*cos_Theta_b;
Rb12=Ra12;
Rb13=Ra11*cos_Theta_b+Ra13*sin_Theta_b;
Rb21=Ra21*sin_Theta_b-Ra23*cos_Theta_b;

```
Rb22=Ra22;
Rb23=Ra21*cos_Theta_b+Ra23*sin_Theta_b;
Rb31=Ra31*sin_Theta_b-Ra33*cos_Theta_b;
Rb32=Ra32;
Rb33=Ra31*cos_Theta_b+Ra33*sin_Theta_b;
Rc11=Rb11*Rh11+Rb12*Rh21+Rb13*Rh31;
Rc12=Rb11*Rh12+Rb12*Rh22+Rb13*Rh32;
Rc13=Rb11*Rh13+Rb12*Rh23+Rb13*Rh33;
Rc21=Rb21*Rh11+Rb22*Rh21+Rb23*Rh31;
Rc22=Rb21*Rh12+Rb22*Rh22+Rb23*Rh32;
Rc23=Rb21*Rh13+Rb22*Rh23+Rb23*Rh33;
Rc31=Rb31*Rh11+Rb32*Rh21+Rb33*Rh31;
Rc32=Rb31*Rh12+Rb32*Rh22+Rb33*Rh32;
Rc33=Rb31*Rh13+Rb32*Rh23+Rb33*Rh33;
sin_Theta_wf_s=-Rc12;
Theta_wf_s_RH=asin(sin_Theta_wf_s);
cos_Theta_wf_s=cos(Theta_wf_s_RH);
/* Compute Theta_f_s_RH */
var1=Rc11/cos_Theta_wf_s;
var2=-Rc13/cos_Theta_wf_s;
Theta_f_s_RH=asin(var2) or acos(var1) depending or region;
/* Compute ThetaAx1_s_RH */
var1=Rc22/cos_Theta_wf_s;
var2=-Rc32/cos_Theta_wf_s;
ThetaAx1_s_RH=asin(var2) or acos(var1) depending or region;
10. Repeat steps 7-9 for left hand system
11. Determine motor axle angles necessary to achieve desired positions/orientations of the slave systems, and command the motors to the determined positions.
```

```
              Des_Rad[s_Ls_RH] = 63.04*(Ls_RH-Ls_init_RH - 0.75*(Xi_RH-Xi_init_RH));
              Des_Rad[s_Xi_RH] = -126.08*(Xi_RH-Xi_init_RH);
              Des_Rad[s_Omega_RH] = -23.64*(Omega_RH-Omega_init_RH);
              Des_Rad[s_Axi_RH] = -23.64*1.3333*(ThetaAxl_s_RH + Omega_RH-
Omega_init_RH);
              Des_Rad[s_wrist_RH] = 18.9*Theta_wf_s_RH;
              Des_Rad[s_f1_RH] = 18.9*(Theta_f_s_RH + Theta_f_m_RH);
              Des_Rad[s_f2_RH] = 18.9*(-Theta_f_s_RH + Theta_f_m_RH);
              Des_Rad[s_Ls_LH] = -63.04*(Ls_LH-Ls_init_LH - 0.75*(Xi_LH-Xi_init_LH));
              Des_Rad[s_Xi_LH] = 126.08*(Xi_LH-Xi_init_LH);
              Des_Rad[s_Omega_LH] = -23.64*(Omega_LH-Omega_init_LH);
              Des_Rad[s_Ax1_LH] = -23.64*1.3333*(ThetaAxl_s_LH + Omega_LH-
Omega_init_LH);
              Des_Rad[s_wrist_LH] = 18.9*Theta_wf_s_LH;
              Des_Rad[s_f1_LH] = -18.9*(-Theta_f_s_LH - Theta_f_m_LH);
              Des_Rad[s_f2_LH] = -18.9*(Theta_f_s_LH - Theta_f_m_LH);
        /* Compute motor output for slave systems */
        for(i=0;i<14;i++)
        {
              Des_Vel[i] = 0.0;
              Err_Rad[i] = Des_Rad[i] - Radian[i];
              Err_Vel[i] = Des_Vel[i] - Velocity[i];
              kpcmd = Kp[i]*Err_Rad[i];
              kdcmd = (Kp[i]*Td[i])*Err_Vel[i];
              Mout_f[i] = kpcmd + kdcmd;
        }
        /* Virtual boundaries for master handles */
        if(Xwo_s_RH>=Xw_s_b1_RH)
        {
              Fx_RH = 3.0*k_master*(Xwo_s_RH-Xw_s_b1_RH);
              Mout_f[m_base_RH] = Fx_RH*cos(0.7854-(Radian[m_base_RH]/14.8));
              Mout_f[m_shoulder_RH] = Fx_RH*sin(0.7854-
(Radian[m_base_RH]/14.8))-              1.0*Radian[m_shoulder RH];
        }
        else if (Xwo_s_RH<=Xw_sb2_RH)
        {
              Fx_RH = k_master*(Xwo_s_RH-Xw_s_b2_RH);
              Mout_f[m_base_RH] = Fx_RH*cos(0.7854-(Radian[m_base_RH]/14.8));
              Mout_f[m_shoulder_RH] = Fx_RH*sin(0.7854-
(Radian[m_base_RH]/14.8))-              1.0*Radian[m_shoulder_RH];
        }
        else
        {
              Mout_f[m_base_RH]=0.0;
              Mout_f[m_shoulder_RH]=-1.0*Radian[m_shoulder_RH];
        }
        if(Ywo_s_RH>=Yw_s_b2_RH)
        {
              Mout_f[m_elbow_RH] = -k_master*(Ywo_s_RH-Yw_s_b2_RH);
        }
        else if (Ywo_s_RH<=Yw_s_b1_RH)
        {
              Mout_f[m_elbow_RH] =-k_master*(Ywo_s_RH-Yw_s_b1_RH);
        }
        else Mout_f[m_elbow_RH]=0.0;
        /* Repeat for left master handle */
```

12. Go back to step 6 and repeat.

Previously there has been described an algorithm for providing controlled operation between the master and slave units. The following description relates this operation to the system of FIGS. 1–2.

The controller 9 receives input signals from the input device 3 that represent the relative positions of the different portions of the input device. These relative positions are then used to drive the instrument 14 to a corresponding set of relative positions. For example, the input device includes a base 50 (FIG. 2A) to which a first link 90 is rotatably connected. A second link 96 is rotatably connected to the first link at an elbow joint 94. Connected to the second link 96 opposite the elbow joint 94 is a wrist joint 98A and two fingers. A surgeon may attach a thumb and forefinger to the two fingers and move the input device to drive the instrument 14.

As the surgeon operates the input device, rotational position of the base (Thetabp1_m_RH), the rotational position of the first link relative to the base (Theta3_m_RH), the rotational position of the second link relative to the first link (Theta2_m_RH), the angle of the wrist joint relative to the second link (PHI_f_m_RH, i.e., the angle the wrist joint is rotated about an axis perpendicular to the length of the second link), the rotary angle of the wrist joint relative to the second link (ThetaAx1_m_RH, i.e., the angle the wrist joint is rotate about an axis parallel to the length of the second link), and the angles of the fingers (Theta_f1_m_RH and Theta_f2_m_RH) are provided to the controller.

When the surgical instrument is first started, the controller initializes all of the position encoders in the instrument 14 and the input device 3, assuming that the system has been started in a desired initial configuration. See Sections 1–3 of the algorithm. The initial position of the input device, e.g., Xwo_m_RH, Ywo_m_RH, and Zwo_m_RH, is then used to establish a reference position for the input device, Xwref_m_RH, Ywref_m_RH, and Zwref_m_RH. See Section 3 of the algorithm. Initial positions are also established for the instrument 14 based on the dimensions of the instrument 14. See Section 3 of the algorithm.

With reference to Section 3 of the algorithm, it is noted that there is an assignment of the initial position of the wrist for the slave, and that this is not a forward kinematics calculation based upon joint angles, but rather is a number based upon the predefined configuration of the slave unit. The coordinate of the slave relates to fixed physical dimensions of the instrument and instrument holder.

As the surgeon moves the input device 3, the encoder values for the input device are read and used to compute the current absolute position of the input device, i.e., Xw_m_RH Yw_m_RH and Zw_m_RH. See Sections 6 and 7 of the algorithm. The controller then determines the desired position of the tool 18 (Xw_s_RH, Yw_s_RH, and Zw_s_RH) base on the current position of the input device (Xw_m_RH Yw_m_RH, and Zw_m_RH), the reference position for the input device (Xwref_m_RH, Ywref_m_RH, and Zwref_m_RH) and the reference position for the instrument 14 (Xwref_s_RH, Ywref_s_RH, and Zwref_s_RH). See Section the algorithm. The desired position of the tool 18 (Xw_s_RH, Yw_s_RH, and Zw_s_RH) is then transformed by a 45° coordinate transformation giving the desired position (Xwo_s_RH, Ywo_s_RH, Zwo_s_RH) which is used to determine joint angles and drive motor angles for the instrument 14 orientation to match that of the input device. See Sections 8–11 of the algorithm. Thus, movement of the surgical instrument 14 is determined based on the current absolute position of the input device, as well as the initial positions of the input device and the instrument at the time of system start-up.

E. Select Features of Described Embodiment

The control in accordance with the present embodiment, as exemplified by the foregoing description and algorithm, provides an improvement in structure and operation while operating in a relatively simple manner. For example, the control employs a technique whereby the absolute position of the surgeon input device is translated into control signals to move the instrument to a corresponding absolute position. This technique is possible at least in part because of the particular construction of the instrument and controllable instrument holder, which essentially replace the cumbersome prior art multi-arm structures including one or more passive joints. Here there is initialized an all active joint construction, including primarily only a single instrument holder having a well-defined configuration with respect to the inserted instrument.

Some prior-art systems rely upon passive joints to initially position the distal tip of the surgical instrument. Because the positions of the passive joints are initially unknown, the position of the distal tip of the surgical instrument with respect to the robot (instrument holder) is also unknown. Therefore, these systems require an initial calculation procedure. This involves the reading of joint angles and the computation of the forward kinematics of all elements constituting the slave. This step is necessary because the joint positions of the slave are essentially unknown at the beginning of the procedure.

On the other hand, in accordance with the present invention it is not necessary to read an initial position of joint angles in order to determine an initial position of the distal tip of the surgical instrument. The system of the present invention, which preferably employs no passive joints, has the initial position of the distal tip of the surgical instrument known with respect to the base of the instrument. The instrument is constructed with known dimensions, such as between base pivot 225 and the wrist (303 at axis 306 in FIG. 2D) of the tool 18. Further, the instrument is initially inserted by the surgeon in a known configuration, such as illustrated in FIGS. 9 and 10, where the dimensions and orientations of the instrument insert and adaptor guide tube are known with respect to the base (pivot 225). Therefore, an initial position of the surgical instrument distal tip need not be calculated before the system is used.

The system of the present embodiment is fixed to the end of a static mount (bracket 25 on post 19) which is manually maneuvered over the patient, such as illustrated in FIG. 1. Since the initial position of the surgical instrument tip (tool 18) with respect to the base (pivot 225) of the articulate mechanism is invariant, the joint positions are neither read nor is the forward kinematics computed during the initial setup. Thus, the initial position of the surgical instrument tip is neither computed nor calculated. In addition, because the base of the system in accordance with the present embodiment is not necessarily fixed directly to the surgical table, but rather movable during a surgical procedure, the initial position of the surgical instrument in a world coordinate system is not knowable.

Another advantage of the present system is that the instrument does not use the incision in the patient to define a pivot point of the instrument. Rather, the pivot point of the instrument is defined by the kinematics of the mechanism, independent of the patient incision, the patient himself, or the procedure. Actually, the pivot point in the present system is defined even before the instrument enters the patient, because it is a pivot point of the instrument itself. This arrangement limits trauma to the patient in an area around the incision.

From an illustrative standpoint, the base of the instrument may be considered as pivot 225 (FIG. 8), and the wrist may be the pivot location 604 (axis) depicted in FIG. 16B (or axis 306 in FIG. 2D). The guide tube 17 has known dimensions and because there are no other joints (active or passive) between the pivot 225 and wrist joint, all of the intervening dimensions are known. Also, the instrument when placed in position has a predefined configuration such as that illustrated in FIGS. 1, 9 and 10 with the guide tube flat is one plane.

The guide tube 17 may also have an alignment mark therealong essentially in line with the pivot 225, as shown in FIG. 9. This marks the location where the guide tube 17 is at the patient incision point. The result is minimal trauma to the patient occasioned by any pivoting action about pivot 225.

Another advantage is the decoupling nature of the present system. This decoupling enables the slave unit to be readily portable. Here the instrument, drive unit and controller are decouplable. A sterilized adaptor 15 is inserted into a patient, then coupled to a non-sterile drive unit 8 (outside the sterile field). Instrument inserts 16 are then removably attached to the surgical adaptor to perform the surgical procedure. The system of the present embodiment separates the drive unit 8 from the instruments 16. In this way, the instruments can be maintained as sterile, but the drive unit need not be sterilized. Furthermore, at the time of insertion, the adaptor 15 is preferably decoupled from the drive unit 8 so it can be readily manually maneuvered to achieve the proper position of the instrument relative to the patient and the patient's incision.

In accordance with the present embodiment, the instrument inserts 16 are not connected to the controller 9 by way of any input/output port configuration. Rather, the present system employs an exclusively mechanical arrangement that is effected remotely and includes mechanical cables and flexible conduits coupling to a remote motor drive unit 8. This provides the advantage that the instrument is purely mechanical and does not need to be contained within a sterile barrier. The instrument may be autoclaved, gas sterilized or disposed in total or in part.

The present system also provides an instrument that is far less complex than prior art robotic system. The instrument is far smaller than that of a typical prior art robotic system, because the actuators (motors) are not housed in the articulate structure in the present system. Because the actuators are remote, they may be placed under the operating table or in another convenient location and out of the sterile field. Because the drive unit is fixed and stationary, the motors may be of arbitrary size and configuration, without effecting the articulated mechanics. Finally, the design allows multiple, specialized instruments to be coupled to the remote motors. This allows one to design an instrument for particular surgical disciplines including, but not limited to, such disciplines as cardiac, spinal, thoracic, abdominal, and arthroscopic.

A further important aspect is the ability to make the instrument disposable. The disposable element is preferably the instrument insert 16 such as illustrated in FIG. 15A. This disposable unit may be considered as comprising a disposable, mechanically drivable mechanism such as the coupler 300 interconnected to a disposable tool 18 through a disposable elongated tube such as the stem section 301, 302 of the instrument insert. This disposable implement is mounted so that the mechanically drivable mechanism may be connectable to and drivable from a drive mechanism. In the illustrated embodiment the drive mechanism may include the coupler 230 and the associated drive motors. The disposable elongate tube 301, 302 is inserted into an incision or orifice of a patient along a selected length of the disposable elongated tube.

The aforementioned disposable implement is purely mechanical and can be constructed relatively inexpensively, thus lending itself readily to being disposable. Another factor that lends itself to disposability is the simplicity of the instrument distal end tool (and wrist) construction. Prior tool constructions, whether graspers or other types, are relatively complex in that they usually have multiple pulleys at the wrist location for operation of different degrees-of-freedom there, making the structure quite intricate and relatively expensive to manufacture. On the other hand, in accordance with the present invention, no pulleys are required and the mechanism in the location of the wrist and tool is simple in construction and can be manufactured at far less expense, thus readily lending itself to disposability. One of the aspects of the invention that has enabled elimination of the pulleys, or the like, is the decoupling of tool action relative to wrist action by passing the tool actuation cables essentially through the center axis (604 in FIGS. 16A and 16B) of the wrist joint. This construction allows proper wrist action without any significant action being conveyed to the tool cables, and furthermore allows for a very simple and inexpensive construction at the distal end of the implement.

Another aspect is the relative simplicity of the system, both in its construction and use. This provides an instrument system that is far less complex than prior robotic systems. Furthermore, by enabling a decoupling of the slave unit at the motor array, there is provided a readily portable and readily manually insertable slave unit that can be handled quite effectively by the surgeon or assistant when the slave unit is to be engaged through a patient incision or orifice. This enables the slave unit to be positioned through the incision or orifice so as to dispose the distal end at a target or operative site. A support is then preferably provided so as to hold a base of the slave unit fixed in position relative to the patient at least during a procedure that is to be carried out. This initial positioning of the slave unit with a predefined configuration immediately establishes an initial reference position for the instrument from which control occurs via a controller and user interface.

This portable nature of the slave unit comes about by virtue of providing a relatively simple surgical instrument insert in combination with an adaptor for the insert that is of relatively small configuration, particularly compared with prior large articulated robotic arm(s) structures. Because the slave unit is purely mechanical, and is decouplable from the drive unit, the slave unit can be readily positioned by the operator. Once in position, the unit is then secured to the support and the mechanical cables are coupled with the drive unit. This makes the slave unit both portable and easy to position in place for use.

Another advantage of the system is the ability to position the holder or adaptor for the instrument with its distal end at the operative site and maintained at the operative site even during instrument exchange. By way of example, and with reference to FIG. 2B, the instrument holder is represented by the guide tube 17 extending to the operative site OS. When instruments are to be exchanged, the distal end of the guide tube 17 essentially remains in place and the appropriate instruments are simply inserted and/or withdrawn depending on the particular procedure that is being carried out.

Accordingly, one of the advantages is the ease of exchanging instruments. In a particular operation procedure, there may be a multitude of instrument exchanges and the present system is readily adapted for quick and easy instrument exchange. Because the holder or adaptor is maintained in position, the surgeon does not have to be as careful each and every time that he reintroduces an instrument into the patient. In previous systems, the instrument is only supported through a cannula at the area of the incision and when an instrument exchange is to occur, these systems require removal of the entire assembly. This means that each time a new instrument is introduced, great care is required to reposition the distal end of the instrument so as to avoid internal tissue or organ damage. On the other hand, in accordance with the present invention, because the holder or adaptor is maintained in position at the operative site, even during instrument exchange, the surgeon does not have to be as careful as the insert simply slides through the rigid tube adaptor. This also essentially eliminates any chance of tissue or organ damage during this instrument exchange.

Having now described a limited number of embodiments of the present invention, it should be apparent to those skilled in the art that numerous other embodiments and modifications thereof are contemplated as falling within the scope of the present invention.

What is claimed is:

1. A method of controlling a surgical instrument that is inserted in a patient for facilitating a surgical procedure and controlled remotely from an input device manipulated by a surgeon at a user interface, said method comprising the steps of:
   initializing the position of the surgical instrument without calculating its initial position, and the position of the input device under electronic control;
   said initializing including establishing an initial reference position for the input device and an initial reference position for the surgical instrument calculating the current position of the input device as it is manipulated by the surgeon;
   determining the desired position of the surgical instrument based upon;
     the current position of the input device,
     the initial reference position of the input device, and
     the initial reference position of the surgical instrument, and
   moving the surgical instrument to the desired position so that the position of the surgical instrument corresponds to that of the input device.

2. A method as set forth in claim 1 wherein the input device has position sensors, and the step of initializing includes these position sensors.

3. A method set forth in claim 2 wherein the initializing is to zero.

4. A method as set forth in claim 1 including computing an initial reference orientation for the input device.

5. A method as set forth in claim 4 including computing a desired orientation for the surgical instrument.

6. A method as set forth in claim 5 including computing a desired position for the surgical instrument.

7. A method as set forth in claim 1 wherein said initializing step includes performing a forward kinematic computation from the input device.

8. A method as set forth in claim 2 including reading position sensor values and current time.

9. A method as set forth in claim 8 wherein the calculating step includes calculating both the position and orientation of the input device.

10. A method as set forth in claim 1 including calculating the current orientation of the input device.

11. A method as set forth in claim 1 wherein said step of determining includes performing an inverse kinematic computation.

12. A method as set forth in claim 1 wherein said determining step includes a transformation into an earth coordinate system.

13. A method as set forth in claim 12 wherein from said transformation there are determined joint angles and drive motor angles for the surgical instrument orientation.

14. A method of controlling a tool of a surgical instrument that is inserted in a patient for carrying out a surgical procedure and is controlled remotely by way of an electronic controller from an input device at a user interface, said method comprising the steps of:
   setting the input device at an initial reference configuration and under electronic controller control;
   setting the surgical instrument in the patient at an initial predefined reference configuration without electronic controller control;
   calculating the current absolute position of the input device;
   determining the desired location of the tool by a kinematic computation that accounts for at least the initial reference configuration of the input device and the current absolute position of the input device; and
   moving the surgical instrument to the desired position so that the location of the tool corresponds to that of the input device.

15. A method as set forth in claim 14 wherein said step of determining is also based upon the initial reference configuration of the tool.

16. A method as set forth in claim 14 wherein the input device has position sensors, and the step of setting includes initializing these position sensors.

17. A method as set forth in claim 14 including computing an initial reference orientation for the input device.

18. A method as set forth in claim 14 including computing a desired orientation for the surgical instrument.

19. A method as set forth in claim 14 wherein said calculating step includes performing a forward kinematic computation from the input device.

20. A method as set forth in claim 14 including calculating the current orientation of the input device.

21. A method as set forth in claim 14 wherein said step of determining includes performing an inverse kinematic computation.

22. A method as set forth in claim 14 wherein said determining step includes a transformation into an earth coordinate system.

23. A method as set forth in claim 22 wherein from said transformation there are determined joint angles and drive motor angles for the surgical instrument orientation.

24. A method of controlling a medical implement remotely from an input device that is controlled by an operator, said method comprising the steps of:
   positioning the medical implement at an initial start position at an operative site for the purpose of facilitating a medical procedure;
   establishing a fixed position reference coordinate representative of the initial start position of said medical implement based upon a base point of the implement and an active point of the implement being in an initial known relative dimensional configuration,
   positioning the input device at an initial start position;
   establishing a fixed position reference coordinate;
   calculating the current position of the input device as it is controlled;
   determining the desired position of the medical implement based upon;

the current position of the input device, the fixed position reference coordinate of the input device, and the fixed position reference coordinate of the medical implement, and moving the medical implement to the desired position so that the position of the medical implement corresponds to that of the input device.

25. A method as set forth in claim 24 wherein, in said step of positioning the medical implement, the medical implement comprises a surgical instrument.

26. A method as set forth in claim 25 wherein, in said step of positioning the medical implement, the medical implement comprises a catheter.

27. A method as set forth in claim 24 wherein said step of positioning the medical implement includes physically placing the distal end of the medical implement at the operative site.

28. A method as set forth in claim 27 wherein said medical implement is placed without pre-computation of a coordinate position at which it is placed.

29. A method as set forth in claim 28 wherein said step of positioning the medical implement is only controlled by manual placement without any electric pre-computation of a predetermined coordinate position to control the actual placement of the medical implement.

30. A method as set forth in claim 24, wherein, in said step of positioning the medical implement, the medical implement comprises a surgical instrument having a tool and a wrist, said established reference coordinate corresponding to an initial position of a location on said wrist.

31. A method as set forth in claim 24 further including providing an electronic controller for controlling said medical implement and wherein the step of positioning the medical implement includes manually placing the medical implement without computation by said controller of an initial coordinate position.

32. A method as set forth in claim 24 further including providing an electronic controller for controlling said medical implement and wherein the step of positioning the input device includes initially moving the input device under controller control so as to establish the reference coordinate position of the input device.

33. A method as set forth in claim 25 including storing in the controller the reference coordinate position of the input device.

34. A method as set forth in claim 24 wherein said step of establishing includes performing a forward kinematic computation.

35. A method as set forth in claim 34 wherein said calculating step includes calculating both the position and the orientation of the input device.

36. A method as set forth in claim 35 wherein said step of determining includes performing an inverse kinematic computation.

37. The method as set forth in claim 24 wherein said step of establishing a fixed position reference coordinate representative of the initial start position of said medical implement includes establishing said reference coordinate in relation to the patients body.

38. The method as set forth in claim 37 wherein the reference coordinate of the implement is at a predetermined location of the patient.

39. The method as set forth in claim 38 wherein the predetermined location is at an incision.

40. The method as set forth in claim 38 wherein the reference coordinate of the implement corresponds to an internal site of the patient.

41. The method as set forth in claim 40 wherein the reference coordinate of the implement corresponds to a site external of the patient.

42. The method as set forth in claim 24 wherein the step of establishing a fixed position reference coordinate representative of the initial start position of said medical implement includes aligning an axis of the base point of the medical implement with an incision in the patient.

43. The method as set forth in claim 24 wherein the step of determining includes performing a coordinate transformation from the base point to the active point of the implement.

44. The method as set forth in claim 43 wherein the coordinate transform is a fixed transform less than 90 degrees.

45. The method as set forth in claim 44 wherein the fixed transform is on the order of 45 degrees.

46. The method as set forth in claim 45 wherein the fixed transform on the order of 45 degrees corresponds to the curvature of the guide tube.

47. A method of controlling a surgical instrument remotely from an input device and by way of an electronic controller, said method comprising the steps of:

inserting the surgical instrument through an incision in the patient so as to dispose the distal end of the instrument at an initial start position;

establishing a fixed position reference coordinate system corresponding to a fixed predefined configuration of the surgical instrument at the initial start position of said surgical instrument;

positioning the input device at an initial start position;

establishing a fixed position reference coordinate system representative of the initial start position of said input device;

calculating the current absolute position of the input device as it is controlled;

determining the desired position of the surgical instrument based upon the current absolute position of the input device, and the fixed position reference coordinate system for the respective surgical instrument and input device; and moving the surgical instrument to the desired position so that the position of the surgical instrument corresponds to that of the input device.

48. A method as set forth in claim 47 wherein said step of positioning the input device includes initializing the location of the input device wider control of the controller.

49. A method as set forth in claim 48 wherein said surgical instrument is initially positioned without control from said controller.

50. A method as set forth in claim 47 wherein the initial start position is determined only by manual insertion.

51. A method as set forth in claim 50 wherein the step of positioning the input device comprises initially moving the input device under controller control so as to establish the reference coordinate position of the input device.

52. A method as set forth in claim 51 including storing in the controller the reference coordinate position of the input device.

53. A method as set forth in claim 47 wherein said step of calculating includes performing a forward kinematic computation.

54. A method as set forth in claim 53 wherein said calculating step includes calculating both the position and the orientation of the input device.

55. A method as set forth in claim 54 wherein said step determining includes performing an inverse kinematic computation.

56. A method of controlling a medical implement remotely from an input device and by way of an electronic controller, said method comprising the steps of:
- inserting the medical implement through an incision in a patient so as to dispose the medical implement in a pre-select initial configuration;
- assigning a fixed initial reference coordinate to a work element of the medical implement based upon a known dimension between said work element and a base of the medical implement and said preselected initial configuration;
- positioning the input device at an initial start position;
- establishing a fixed initial reference coordinate representative of the initial start position of die input device;
- calculating the current position of the input device as it is controlled;
- determining the desired position of the medical implement based upon at least the current position of the input device; and
- moving the medical implement so that the position thereof corresponds to that of the input device.

57. A method as set forth in claim 56 wherein said step of inserting the medical implement includes inserting a surgical instrument.

58. A method as set forth in claim 56 wherein said step of inserting the medical implement includes inserting a catheter.

59. A method as set forth in claim 56 wherein said step of inserting the medical implement includes inserting a distal end of the medical implement through the incision so as to be disposed at a target site.

60. A method as set forth in claim 56 wherein said step of inserting the medical implement includes placing the medical implement without pre-computation of a coordinate position at which it is placed.

61. A method as set forth in claim 56 wherein said step of assigning includes placing the medical implement without pre-computation to determine a coordinate position.

62. A method as set forth in claim 56 wherein said step of establishing a fixed initial reference coordinate for the input device includes executing a forward kinematic computation to determine the reference coordinate.

63. A method as set forth in claim 62 wherein said step of executing a forward kinematic computation includes determining both the position and orientation of the input device.

64. A method as set forth in claim 62 wherein said step of executing a forward kinematic computation includes determining a position by a geometric calculation.

65. A method as set forth in claim 64 including determining an orientation by a transformation matrix.

66. A method as set forth in claim 56 wherein said step of determining includes performing an inverse kinematic computation.

67. A method as set forth in claim 66 including determining joint angles and insertion length of the instrument.

68. A method as set forth in claim 67 including determining the instrument orientation.

* * * * *